US007517672B2

(12) United States Patent
Snutch et al.

(10) Patent No.: US 7,517,672 B2
(45) Date of Patent: Apr. 14, 2009

(54) NUCLEIC ACIDS ENCODING MAMMALIAN T-TYPE CALCIUM CHANNELS

(75) Inventors: Terrance P. Snutch, Vancouver (CA); David L. Baillie, Vancouver (CA)

(73) Assignee: Neuromed Pharmaceuticals Ltd., Vancouver, BC (CA)

( * ) Notice: Subject to any disclaimer, the term of this patent is extended or adjusted under 35 U.S.C. 154(b) by 116 days.

(21) Appl. No.: 11/649,452

(22) Filed: Jan. 3, 2007

(65) Prior Publication Data

US 2007/0178553 A1 Aug. 2, 2007

Related U.S. Application Data

(60) Division of application No. 09/611,257, filed on Jul. 6, 2000, now Pat. No. 7,157,243, which is a continuation-in-part of application No. 09/346,794, filed on Jul. 2, 1999, now Pat. No. 7,297,504.

(51) Int. Cl.
*C12N 15/12* (2006.01)
*C12N 15/63* (2006.01)
*C12N 15/85* (2006.01)

(52) U.S. Cl. ................... 435/69.1; 435/320.1; 435/325; 435/252.3; 536/23.5

(58) Field of Classification Search ....................... None
See application file for complete search history.

(56) References Cited

U.S. PATENT DOCUMENTS

| | | | | |
|---|---|---|---|---|
| 5,386,025 | A | 1/1995 | Jay et al. | |
| 5,401,629 | A | 3/1995 | Harpold et al. | |
| 5,429,921 | A | 7/1995 | Harpold et al. | |
| 5,688,938 | A | 11/1997 | Brown et al. | |
| 5,804,436 | A | 9/1998 | Okun et al. | |
| 5,837,479 | A | 11/1998 | Young et al. | |
| 6,309,858 | B1 | 10/2001 | Dietrich et al. | |
| 6,358,706 | B1 | 3/2002 | Dubin et al. | |
| 6,528,630 | B1 | 3/2003 | Williams et al. | |
| 7,297,504 | B1 * | 11/2007 | Snutch et al. | 435/7.21 |
| 2003/0125269 | A1 | 7/2003 | LI | |

FOREIGN PATENT DOCUMENTS

| | | |
|---|---|---|
| EP | 0 507 170 | 10/1992 |
| WO | WO-95/04144 | 2/1995 |
| WO | WO-96/39512 | 12/1996 |
| WO | WO-98/38301 | 9/1998 |
| WO | WO-99/28342 | 6/1999 |
| WO | WO-99/29847 | 6/1999 |
| WO | WO-00/70044 | 11/2000 |
| WO | WO-01/19845 | 3/2001 |

OTHER PUBLICATIONS

Broun et al., Science (1998) 282:1315-1317.

Database DDBJ/EMBL/GenBank [online], Accession No. F07776, <http://www.ncbi.nlm.nih.gov/entrez/viewer.fcgi?db=nucest &id=677276>.

Office Action for Canadian Application No. 2,281,984, date mailed on Sep. 4, 2007, 6 pages.

Office Action for Japanese Application No. 537117/98, date mailed on Jul. 24, 2007, 6 pages.

Seffernick et al., J. Bacteriology (2001) 183(8):2405-2410.

Skolnick and Fetrow, Tibtech (2000) 18:34-39.

Tips (1997) 18:37-42, Ertel et al.

Bork et al., Current Opinion in Structural Biology (1998) 8:331-332.

Bork et al., Nature Genetics (1998) 18:313-318.

Brizzard et al., Current Protocols in Neuroscience (1997) pp. 5.8.1-5.8.10.

Coulter et al., Annals of Neurology (1989) 25:582-593.

Cribbs et al., Circulation Research (1998) 83:103-109.

Ertel and Ertel, Tips (1997) 18:37-42.

Hille, Ionic Channels of Excitable Membranes, 2nd ed., (1992) Sunderland, MA: Sinauer Associates.

Karp et al., Bioinformatics (1988) 14(9):753-754.

Lee et al., J. Neurosci. (1999) 19(6):1912-1921.

McRory et al., Journal of Biological Chemistry (2001) 276(6):3999-4011.

McRory et al., Society for Neuroscience Abstracts (1999) 25(1-2):197.

Perez-Reyes et al., Nature (1998) 391:896-900.

Promega catalog pSP72 vector.

Pubmed search results for "t-type calcium channel Parkinson's" and "t-type calcium channel schizophrenia" accessed Sep. 27, 2005.

Stratagene catalog, 1991. p. 66.

Trofatter et al., Genome Res. (1995) 5(3):214-224.

Williams et al., J. Neurochem. (1999) 72(2):791-799.

Williams et al., Neuron (1992) 8:71-84.

Yunker, Journal of Bioenergetics and Bioengineering (2003) 35:577-598.

U.S. Appl. No. 60/117,339, filed Jan. 27, 1999.

U.S. Appl. No. 08/985,809, filed Dec. 5, 1997.

Partial European Search Report for EP 06 11 5615, mailed on Feb. 27, 2007, 4 pages.

Mittman et al., Neuroscience Letters (1999) 274(3):143-146.

* cited by examiner

*Primary Examiner*—Daniel E. Kolker
(74) *Attorney, Agent, or Firm*—Morrison & Foerster LLP

(57) ABSTRACT

Sequences and partial sequences for three types of mammalian (human and rat sequences identified) T-type calcium channel subunits which we have labeled as the $\alpha_{1G}$, $\alpha_{1H}$ and $\alpha_{1I}$ subunits are provided. Knowledge of the sequence of these calcium channel permits the localization and recovery of the complete sequence from human cells, and the development of cell lines which express the novel calcium channels of the invention. These cells may be used for identifying compounds capable of acting as agonists or antagonists to the calcium channels.

10 Claims, 18 Drawing Sheets

α1G cDNA Construct

α1G cDNA Clones

Human α₁G T-Type Calcium Channel cDNA (SEQ ID NO:36)

```
  1 aagcttgctgcccctctccgatcgcccggggcccggctgccagagg ATG GAC GAG GAG GAT GGA          71
                                        (SEQ ID NO:37)  M   D   E   E   D   G        1

 72 GCG GGC GCC GAG GAG TCG GGA CAG CCC CGG AGC TTC ATG CGG CTC AAC GAC CTG TCG GGG 131
  7  A   G   A   E   E   S   G   Q   P   R   S   F   M   R   L   N   D   L   S   G   27

132 GCC GGG GGC CGG CCG GGG CCC TCA GCA GAA AAG GAC GTG GCC AGC CCG GAC TCC GAG     191
 28  A   G   G   R   P   G   P   S   A   E   K   D   V   A   S   P   D   S   E      47

192 GCG GAG GGG CTG CCG TAC CCG GCG CTG GCC CCG GTT GTC TTC TTC TAC TTG AGC CAG GAC 251
 48  A   E   G   L   P   Y   P   A   L   A   P   V   V   F   F   Y   L   S   Q   D   67

252 AGC CGC CCG CGG AGC TGG TGT CTC CGC ACG GTC TGT AAC CCC TGG TTT GAG CGC ATC AGC 311
 68  S   R   P   R   S   W   C   L   R   T   V   C   N   P   W   F   E   R   I   S   87

312 ATG TTG GTC ATC CTT CTC AAC TGC GTG ACC CTG GGC ATG TTC CGG CCA TGC GAG GAC ATC 371
 88  M   L   V   I   L   L   N   C   V   T   L   G   M   F   R   P   C   E   D   I  107

372 GCC TGT GAC TCC CAG CGC TGC CGG ATC CTG CAG GCC TTT GAT GAC TTC ATC TTT GCC TTC 431
108  A   C   D   S   Q   R   C   R   I   L   Q   A   F   D   D   F   I   F   A   F  127

432 TTT GCC GTG GAG ATG GTG GTG AAG ATG GTG GCC TTG GGC ATC TTT GGG AAA AAG TGT TAC 491
128  F   A   V   E   M   V   V   K   M   V   A   L   G   I   F   G   K   K   C   Y  147

492 CTG GGA GAC ACT TGG AAC CGG CTT GAC TTT TTC ATC GTC ATC GCA GGG ATG CTG GAG TAC 551
148  L   G   D   T   W   N   R   L   D   F   F   I   V   I   A   G   M   L   E   Y  167

552 TCG CTG GAC CTG CAG AAC GTC AGC TTC TCA GCT GTC AGG ACA GTC CGT GTG CTG CGA CCG 611
168  S   L   D   L   Q   N   V   S   F   S   A   V   R   T   V   R   V   L   R   P  187
```

FIG. 6A

```
612  CTC AGG GCC ATT AAC CGG GTG CCC AGC ATG CGC ATC CTT GTC ACG TTG CTG CTG GAT ACG  671
188  L   R   A   I   N   R   V   P   S   M   R   I   L   V   T   L   L   L   D   T    207
672  CTG CCC ATG CTG GGC AAC GTC CTG CTG CTC TGC TTC TTC GTC TTC TTC ATC TTC GGC ATC  731
208  L   P   M   L   G   N   V   L   L   L   C   F   F   V   F   F   I   F   G   I    227
732  GTC GGC GTC CAG CTG TGG GCA GGG CTG CTT CGG AAC CGA TGC TTC CTA CCT GAG AAT TTC  791
228  V   G   V   Q   L   W   A   G   L   L   R   N   R   C   F   L   P   E   N   F    247
792  AGC CTC CCC CTG AGC GTG GAC CTG GAG CGC TAT TAC CAG ACA GAG AAC GAG GAT GAG AGC  851
248  S   L   P   L   S   V   D   L   E   R   Y   Y   Q   T   E   N   E   D   E   S    267
852  CCC TTC ATC TGC TCC CAG CCA CGC GAG AAC GGC ATG CGG TCC TGC AGA AGC GTG CCC ACG  911
268  P   F   I   C   S   Q   P   R   E   N   G   M   R   S   C   R   S   V   P   T    287
912  CTG CGC GGG GAC GGG GGC GGT GGC CCA CCT TGC GGT CTG GAC TAT GAG GCC TAC AAC AGC  971
288  L   R   G   D   G   G   G   G   P   P   C   G   L   D   Y   E   A   Y   N   S    307
972  TCC AGC AAC ACC ACC TGT GTC AAC TGG AAC CAG TAC TAC ACC AAC TGC TCA GCG GGG GAG  1031
308  S   S   N   T   T   C   V   N   W   N   Q   Y   Y   T   N   C   S   A   G   E    327
1032 CAC AAC CCC TTC AAG GGC GCC ATC AAC TTT GAC AAC ATT GGC TAT GCC TGG ATC GCC ATC  1091
328  H   N   P   F   K   G   A   I   N   F   D   N   I   G   Y   A   W   I   A   I    347
1092 TTC CAG GTC ATC ACG CTG GAG GGC TGG GTC GAC ATC ATG TAC TTT GTG ATG GAT GCT CAT  1151
348  F   Q   V   I   T   L   E   G   W   V   D   I   M   Y   F   V   M   D   A   H    367
1152 TCC TTC TAC AAT TTC ATC TAC TTC ATC CTC CTC ATC ATC GTG GGC TCC TTC TTC ATG ATC  1211
368  S   F   Y   N   F   I   Y   F   I   L   L   I   I   V   G   S   F   F   M   I    387
```

FIG. 6B

```
1212 AAC CTG TGC CTG GTG GTG ATT GCC ACG CAG TTC TCA GAG ACC AAG CAG CGG GAA AGC CAG 1271
 388 N   L   C   L   V   V   I   A   T   Q   F   S   E   T   K   Q   R   E   S   Q   407
1272 CTG ATG CGG GAG CAG CGT GTG CGG TTC CTG TCC AAC GCC AGC ACC CTG GCT AGC TTC TCT 1331
 408 L   M   R   E   Q   R   V   R   F   L   S   N   A   S   T   L   A   S   F   S   427
1332 GAG CCC GGC AGC TGC TAT GAG GAG CTG CTC AAG TAC CTG GTG TAC ATC CTT CGT AAG GCA 1391
 428 E   P   G   S   C   Y   E   E   L   L   K   Y   L   V   Y   I   L   R   K   A   447
1392 GCC CGC AGG CTG GCT CAG GTC TCT CGG GCA GCA GGT GTG CGG GTT GGG CGT CTC AGC AGC 1451
 448 A   R   R   L   A   Q   V   S   R   A   A   G   V   R   V   G   L   L   S   S   467
1452 CCA GCA CCC CTC GGG GGC CAG GAG ACC CAG CCC AGC AGC AGC TGC TCT CGC TCC CAC CGC 1511
 468 P   A   P   L   G   G   Q   E   T   Q   P   S   S   S   C   S   R   S   H   R   487
1512 CGC CTA TCC GTC CAC CAC CTG GTG CAC CAC CAC CAC CAC CAT CAC CAC CAC TAC CAC CTG 1571
 488 R   L   S   V   H   H   L   V   H   H   H   H   H   H   H   H   H   Y   H   L   507
1572 GGC AAT GGG ACG CTC AGG GCC CCC CGG GCC AGC CCG GAG ATC CAG GAC AGG GAT GCC AAT 1631
 508 G   N   G   T   L   R   A   P   R   A   S   P   E   I   Q   D   R   D   A   N   527
1632 GGG TCC CGC AGG CTC ATG CTG CCA CCA CCC TCG ACG CCT GCC CTC TCC GGG GCC CCC CCT 1691
 528 G   S   R   R   L   M   L   P   P   P   S   T   P   A   L   S   G   A   P   P   547
1692 GGT GGC GCA GAG TCT GTG CAC AGC TTC TAC CAT GCC GAC TGC CAC TTA GAG CCA GTC CGC 1751
 548 G   G   A   E   S   V   H   S   F   Y   H   A   D   C   H   L   E   P   V   R   567
1752 TGC CAG GCG CCC CCT CCC AGG TCC CCA TCT GAG GCA TCC GGC AGG ACT GTG GGC AGC GGG 1811
 568 C   Q   A   P   P   P   R   S   P   S   E   A   S   G   R   T   V   G   S   G   587
```

FIG. 6C

1812 AAG GTG TAT CCC ACC GTG CAC ACC AGC CCT CCA CCG GAG ACG CTG AAG GAG AAG GCA CTA 1871
588 K V Y P T V H T S P P P E T L K E K A L 607
1872 GTA GAG GTG GCT GCC AGC TCT GGG CCC CCA ACC CTC ACC AGC CTC AAC ATC CCA CCC GGG 1931
608 V E V A A S S G P P T L T S L N I P P G 627
1932 CCC TAC AGC TCC ATG CAC AAG CTG CTG GAG ACA CAG AGT ACA GGT GCC TGC CAA AGC TCT 1991
628 P Y S S M H K L L E T Q S T G A C Q S S 647
1992 TGC AAG ATC TCC AGC CCT TGC TTG AAA GCA GAC AGT GGA GCC TGT GGT CCA GAC AGC TGC 2051
648 C K I S S P C L K A D S G A C G P D S C 667
2052 CCC TAC TGT GCC CGG GCC GGG GCA GGG GAG GTG GAG CTC GCC GAC CGT GAA ATG CCT GAC 2111
668 P Y C A R A G A G E V E L A D R E M P D 687
2112 TCA GAC AGC GAG GCA GTT TAT GAG TTC ACA CAG GAT GCC CAG CAC AGC GAC CTC CGG GAC 2171
688 S D S E A V Y E F T Q D A Q H S D L R D 707
2172 CCC CAC AGC CGG CGG CAA CGG AGC CTG GGC CCA GAT GCA GAG CCC AGC TCT GTG CTG GCC 2231
708 P H S R R Q R S L G P D A E P S S V L A 727
2232 TTC TGG AGG CTA ATC TGT GAC ACC TTC CGA AAG ATT GTG GAC AGC AAG TAC TTT GGC CGG 2291
728 F W R L I C D T F R K I V D S K Y F G R 747
2292 GGA ATC ATG ATC GCC ATC CTG GTC AAC ACA CTC AGC ATG GGC ATC GAA TAC CAC GAG CAG 2351
748 G I M I A I L V N T L S M G I E Y H E Q 767
2352 CCC GAG GAG CTT ACC AAC GCC CTA GAA ATC AGC AAC ATC GTC TTC ACC AGC CTC TTT GCC 2411
768 P E E L T N A L E I S N I V F T S L F A 787

FIG. 6D

```
2412 CTG GAG ATG CTG CTG AAG CTG CTT GTG TAT GGT CCC TTT GGC TAC ATC AAG AAT CCC TAC 2471
 788 L   E   M   L   L   K   L   L   V   Y   G   P   F   G   Y   I   K   N   P   Y   807
2472 AAC ATC TTC GAT GGT GTC ATT GTG GTC ATC AGC GTG TGG GAG ATC GTG GGC CAG CAG GGG 2531
 808 N   I   F   D   G   V   I   V   V   I   S   V   W   E   I   V   G   Q   Q   G   827
2532 GGC GGC CTG TCG GTG CTG CGG ACC TTC CGC CTG ATG CGT GTG CTG AAG CTG GTG CGC TTC 2591
 828 G   G   L   S   V   L   R   T   F   R   L   M   R   V   L   K   L   V   R   F   847
2592 CTG CCG GCG CTG CAG CGG CAG CTG GTG GTG CTC ATG AAG ACC ATG GAC AAC GTG GCC ACC 2651
 848 L   P   A   L   Q   R   Q   L   V   V   L   M   K   T   M   D   N   V   A   T   867
2652 TTC TGC ATG CTG CTT ATG CTC TTC ATC TTC ATC TTC AGC ATC CTG GGC ATG CAT CTC TTC 2711
 868 F   C   M   L   L   M   L   F   I   F   I   F   S   I   L   G   M   H   L   F   887
2712 GGC TGC AAG TTT GCC TCT GAG CGG GAT GGG GAC ACC CTG CCA GAC CGG AAG AAT TTT GAC 2771
 888 G   C   K   F   A   S   E   R   D   G   D   T   L   P   D   R   K   N   F   D   907
2772 TCC TTG CTC TGG GCC ATC GTC ACT GTC TTT CAG ATC CTG ACC CAG GAG GAC TGG AAC AAA 2831
 908 S   L   L   W   A   I   V   T   V   F   Q   I   L   T   Q   E   D   W   N   K   927
2832 GTC CTC TAC AAT GGT ATG GCC TCC ACG TCG TCC TGG GCG GCC CTT TAT TTC ATT GCC CTC 2891
 928 V   L   Y   N   G   M   A   S   T   S   S   W   A   A   L   Y   F   I   A   L   947
2892 ATG ACC TTC GGC AAC TAC GTG CTC TTC AAT TTG CTG GTC GCC ATT CTG GTG GAG GGC TTC 2951
 948 M   T   F   G   N   Y   V   L   F   N   L   L   V   A   I   L   V   E   G   F   967
2952 CAG GCG GAG GAA ATC AGC AAA CGG GAA GAT GCG AGT GGA CAG TTA AGC TGT ATT CAG CTG 3011
 968 Q   A   E   E   I   S   K   R   E   D   A   S   G   Q   L   S   C   I   Q   L   987
```

FIG. 6E

```
3012 CCT GTC GAC TCC CAG GGG GGA GAT GCC AAC AAG TCC GAA TCA GAG CCC GAT TTC TTC TCA 3071
 988 P   V   D   S   Q   G   G   D   A   N   K   S   E   S   E   P   D   F   F   S   1007
3072 CCC AGC CTG GAT GGT GAT GGG GAC AGG AAG AAG TGC TTG GCC TTG GTG TCC CTG GGA GAG 3131
1008 P   S   L   D   G   D   G   D   R   K   K   C   L   A   L   V   S   L   G   E   1027
3132 CAC CCG GAG CTG CGG AAG AGC CTG CTG CCG CCT CTC ATC ATC CAC ACG GCC GCC ACA CCC 3191
1028 H   P   E   L   R   K   S   L   L   P   P   L   I   I   H   T   A   A   T   P   1047
3192 ATG TCG CTG CCC AAG AGC ACC AGC ACG GGC CTG GGC GAG GCG CTG GGC CCT GCG TCG CGC 3251
1048 M   S   L   P   K   S   T   S   T   G   L   G   E   A   L   G   P   A   S   R   1067
3252 CGC ACC AGC AGC AGC GGG TCG GCA GAG CCT GGG GCG GCC CAC GAG ATG AAG TCA CCG CCC 3311
1068 R   T   S   S   S   G   S   A   E   P   G   A   A   H   E   M   K   S   P   P   1087
3312 AGC GCC CGC AGC TCT CCG CAC AGC CCC TGG AGC GCT GCA AGC AGC TGG ACC AGC AGG CGC 3371
1088 S   A   R   S   S   P   H   S   P   W   S   A   A   S   S   W   T   S   R   R   1107
3372 TCC AGC CGG AAC AGC CTC GGC CGT GCA CCC AGC CTG AAG CGG AGA AGC CCA AGT GGA GAG 3431
1108 S   S   R   N   S   L   G   R   A   P   S   L   K   R   R   S   P   S   G   E   1127
3432 CGG CGG TCC CTG TTG TCG GGA GAA GGC CAG GAG AGC CAG GAT GAA GAG GAG AGC TCA GAA 3491
1128 R   R   S   L   L   S   G   E   G   Q   E   S   Q   D   E   E   E   S   S   E   1147
3492 GAG GAG CGG GCC AGC CCT GCG GGC AGT GAC CAT CGC CAC AGG GGG TCC CTG GAG CGG GAG 3551
1148 E   E   R   A   S   P   A   G   S   D   H   R   H   R   G   S   L   E   R   E   1167
3552 GCC AAG AGT TCC TTT GAC CTG CCA GAC ACA CTG CAG CTG CCA GGG CTG CAT CGC ACT GCC 3611
1168 A   K   S   S   F   D   L   P   D   T   L   Q   V   P   G   L   H   R   T   A   1187
```

FIG. 6F

```
3612 AGT GGC CGA GGG TCT GCT TCT GAG CAC CAG GAC TGC AAT CGC AAG TCG GCT TCA GGG CGC 3671
1188 S   G   R   G   S   A   S   E   H   Q   D   C   N   G   K   S   A   S   G   R   1207
3672 CTG GCC CGG GCC CTG CGG CCT GAT GAC CCC CCA CTG GAT GGG GAT GAC GCC GAT GAC GAG 3731
1208 L   A   R   A   L   R   P   D   D   P   P   L   D   G   D   D   A   D   D   E   1227
3732 GGC AAC CTG AGC AAA GGG GAA CGG GTC CGC GCG TGG ATC CGA GCC CGA CTC CCT GCC TGC 3791
1228 G   N   L   S   K   G   E   R   V   R   A   W   I   R   A   R   L   P   A   C   1247
3792 TAC CTC GAG CGA GAC TCC TGG TCA CCC TAC ATC TTC CCT CCT CAG TCC AGG TTC CGC CTC 3851
1248 Y   L   E   R   D   S   W   S   A   Y   I   F   P   P   Q   S   R   F   R   L   1267
3852 CTG TGT CAC CGG ATC ATC ACC CAC AAG ATG TTC GAC CAG GTG GTC CTT GTC ATC ATC TTC 3911
1268 L   C   H   R   I   I   T   H   K   M   F   D   H   V   V   L   V   I   I   F   1287
3912 CTT AAC TGC ATC ACC ATC GCC ATG GAG CGC CCC AAA ATT GAC CCC CAC AGC GCT GAA CGC 3971
1288 L   N   C   I   T   I   A   M   E   R   P   K   I   D   P   H   S   A   E   R   1307
3972 ATC TTC CTG ACC CTC TCC AAT TAC ATC TTC ACC GCA GTC TTT CTG GCT GAA ATG ACA GTG 4031
1308 I   F   L   T   L   S   N   Y   I   F   T   A   V   F   L   A   E   M   T   V   1327
4032 AAG GTG GTG GCA CTG GGC TGG TGC TTC GGG GAG CAG GCG TAC CTG CGG AGC AGT TGG AAC 4091
1328 K   V   V   A   L   G   W   C   F   G   E   Q   A   Y   L   R   S   S   W   N   1347
4092 GTG CTG GAC GGG CTG TTG GTG CTC ATC TCC GTC ATC GAC ATT CTG GTG TCC ATG GTC TCT 4151
1348 V   L   D   G   L   L   V   L   I   S   V   I   D   I   L   V   S   M   V   S   1367
4152 GAC AGC GGC ACC AAG ATC CTG GGC ATG CTG AGG GTG CTG CGG CTG CTG CGG ACC CTG CGC 4211
1368 D   S   G   T   K   I   L   G   M   L   R   V   L   R   L   L   R   T   L   R   1387
```

FIG. 6G

```
4212 CCG CTC AGG GTG ATC AGC CGG GCG CAG GGG CTG AAG CTG GTG GTG GAG ACG CTG ATG TCC 4271
1388 P   L   R   V   I   S   R   A   Q   G   L   K   L   V   V   E   T   L   M   S   1407
4272 TCA CTG AAA CCC ATC GGC AAC ATT GTA GTC ATC TGC TGT GCC TTC TTC ATC ATT TTC GGC 4331
1408 S   L   K   P   I   G   N   I   V   V   I   C   C   A   F   F   I   I   F   G   1427
4332 ATC TTG GGG GTG CAG CTC TTC AAA GGG AAG TTT TTC GTG TGC CAG GGC GAG GAT ACC AGG 4391
1428 I   L   G   V   Q   L   F   K   G   K   F   F   V   C   Q   G   E   D   T   R   1447
4392 AAC ATC ACC AAT AAA TCG GAC TGT GCC GAG GCC AGT TAC CGG TGG GTC CGG CAC AAG TAC 4451
1448 N   I   T   N   K   S   D   C   A   E   A   S   Y   R   W   V   R   M   K   Y   1467
4452 AAC TTT GAC AAC CTT GGC CAG GCC CTG ATG TCC CTG TTC GTT TTG GCC TCC AAG GAT GGT 4511
1468 N   F   D   N   L   G   Q   A   L   M   S   L   F   V   L   A   S   K   D   G   1487
4512 TGG GTG GAC ATC ATG TAC GAT GGG CTG GAT GCT GTG GGC GTG GAC CAG CAG CCC ATC ATG 4571
1488 W   V   D   I   M   Y   D   G   L   D   A   V   G   V   D   Q   Q   P   I   M   1507
4572 AAC CAC AAC CCC TGG ATG CTG CTG TAC TTC ATC TCG TTC CTG CTC ATT GTG GCC TTC TTT 4631
1508 N   H   N   P   N   W   L   L   Y   F   I   S   F   L   L   I   V   A   F   F   1527
4632 GTC CTG AAC ATG TTT GTG GGT GTG GTG GTG GAG AAC TTC CAC AAG TGT AGG CAG CAC CAG 4691
1528 V   L   N   M   F   V   G   V   V   V   E   N   F   H   K   C   R   Q   H   Q   1547
4692 GAG GAA GAG GAG GCC CGG CGG CGG GAG GAG AAG CGC CTA CGA AGA CTG GAG AAA AAG AGA 4751
1548 E   E   E   E   A   R   R   R   E   E   K   R   L   R   R   L   E   K   K   R   1567
4752 AGG AAA GCC CAG TGC AAA CCT TAC TAC TCC GAC TAC TCC CGC TTC CGG CTC CTC GTC CAC 4811
1568 R   K   A   Q   C   K   P   Y   Y   S   D   Y   S   R   F   R   L   L   V   H   1587
```

FIG. 6H

```
4812 CAC TTG TGC ACC AGC CAC TAC CTG GAC CTC TTC ATC ACA GGT GTC ATC GGG CTG AAC GTG 4871
1588 H   L   C   T   S   H   Y   L   D   L   F   I   T   G   V   I   G   L   N   V   1607
4872 GTC ACC ATG GCC ATG GAG CAC TAC CAG CAG CCC CAG ATT CTG GAT GAG GCT CTG AAG ATC 4931
1608 V   T   M   A   M   E   H   Y   Q   Q   P   Q   I   L   D   E   A   L   K   I   1627
4932 TGC AAC TAC ATC TTC ACT GTC ATC TTT GTC TTG GAG TCA GTT TTC AAA CTT GTG GCC TTT 4991
1628 C   N   Y   I   F   T   V   I   F   V   L   E   S   V   F   K   L   V   A   F   1647
4992 GGT TTC CGT CGG TTC TTC CAG GAC AGG TGG AAC CAG CTG GAC CTG GCC ATT GTG CTG CTG 5051
1648 G   F   R   R   F   F   Q   D   R   W   N   Q   L   D   L   A   I   V   L   L   1667
5052 TCC ATC ATG GGC ATC ACG CTG GAG GAA ATC GAG GTC AAC GCC TCG CTG CCC ATC AAC CCC 5111
1668 S   I   M   G   I   T   L   E   E   I   E   V   N   A   S   L   P   I   N   P   1687
5112 ACC ATC ATC CGC ATC ATG AGG GTG CTG CGC ATT GCC CGA GTG CTG AAG CTG CTG AAG ATG 5171
1688 T   I   I   R   I   M   R   V   L   R   I   A   R   V   L   K   L   L   K   M   1707
5172 GCT GTG GGC ATG CGG GCG CTG CTG GAC ACG GTG ATG CAG GCC CTG CCC CAG GTG GGG AAC 5231
1708 A   V   G   M   R   A   L   L   D   T   V   M   Q   A   L   P   Q   V   G   N   1727
5232 CTG GGA CTT CTC TTC ATG TTG TTG TTT TTC ATC TTT GCA GCT CTG GGC GTG GAG CTC TTT 5291
1728 L   G   L   L   F   M   L   L   F   F   I   F   A   A   L   G   V   E   L   F   1747
5292 GGA GAC CTG GAG TGT GAC GAG ACA CAC CCC TGT GAG GGC CTG GGC CGT CAT GCC ACC TTT 5351
1748 G   D   L   E   C   D   E   T   H   P   C   E   G   L   G   R   H   A   T   F   1767
5352 CGG AAC TTT GGC ATG GCC TTC CTA ACC CTC TTC CGA GTC TCC ACA GGT GAC AAT TGG AAT 5411
1768 R   N   F   G   M   A   F   L   T   L   F   R   V   S   T   G   D   N   W   N   1787
```

FIG. 6I

```
5412 GGC ATT ATG AAG GAC ACC CTC CGG GAC TGT GAC CAG GAG TCC ACC TGC TAC AAC ACG GTC 5471
1788 G   I   M   K   D   T   L   R   D   C   D   Q   E   S   T   C   Y   F   T   V   1807
5472 ATC TCG CCT ATC TAC TTT GTG TCC TTC GTG CTG ACG GCC CAG TTC GTG CTA GTC AAC GTG 5531
1808 I   S   P   I   Y   F   V   S   F   V   L   T   A   Q   F   V   L   V   N   V   1827
5532 GTG ATC GCC GTG CTG ATG AAG CAC CTG GAG GAG AGC AAC AAG GAG GCC AAG GAG GAG GCC 5591
1828 V   I   A   V   L   M   K   H   L   E   E   S   N   K   E   A   K   E   E   A   1847
5592 GAG CTA GAG GCT GAG CTG GAG CTG GAG ATG AAG ACC CTC AGC CCC CAG CCC CAC TCG CCA 5651
1848 E   L   E   A   E   L   E   L   E   M   K   T   L   S   P   Q   P   H   S   P   1867
5652 CTG GGC AGC CCC TTC CTC TGG CCT GGG GTC GAG GGC CCC GAC AGC CCC GAC AGC CCC AAG 5711
1868 L   G   S   P   F   L   W   P   G   V   E   G   P   D   S   P   D   S   P   K   1887
5712 CCT GGG GCT CTG CAC CCA GCG GCC CAC GCG AGA TCA GCC TCC CAC TTT TCC CTG GAG CAC 5771
1888 P   G   A   L   H   P   A   A   H   A   R   S   A   S   H   F   S   L   E   H   1907
5772 CCC ACG ATG CAG CCC CAC CCC ACG GAG CTG CCA GGA CCA GAC TTA CTG ACT GTG CGG AAG 5831
1908 P   T   M   Q   P   H   P   T   E   L   P   G   P   D   L   L   T   V   R   K   1927
5832 TCT GGG GTC AGC CGA ACG CAC TCT CTG CCC AAT GAC AGC TAC ATG TGT CGG CAT GGG AGC 5891
1928 S   G   V   S   R   T   H   S   L   P   N   D   S   Y   M   C   R   H   G   S   1947
5892 ACT GCC GAG GGG CCC CTG GGA CAC AGG GGC TGG GGG CTC CCC AAA GCT CAG TCA GGC TCC 5951
1948 T   A   E   G   P   L   G   H   R   G   W   G   L   P   K   A   Q   S   G   S   1967
5952 GTC TTG TCC GTT CAC TCC CAG CCA GCA GAT ACC AGC TAC ATC CTG CAG CTT CCC AAA GAT 6011
1968 V   L   S   V   H   S   Q   P   A   D   T   S   Y   I   L   Q   L   P   K   D   1987
```

FIG. 6J

```
6012 GCA CCT CAT CTG CTC CAG CCC CAC AGC GCC CCA ACC TGG GGC ACC ATC CCC AAA CTG CCC 6071
1988 A   P   H   L   L   Q   P   H   S   A   P   T   W   G   T   I   P   K   L   P   2007
6072 CCA CCA GGA CGC TCC CCT TTG GCT CAG AGG CCA CTC AGG CGC CAG GCA GCA ATA AGG ACT 6131
2008 P   P   G   R   S   P   L   A   Q   R   P   L   R   R   Q   A   A   I   R   T   2027
6132 GAC TCC TTG GAC GTT CAG GGT CTG GGC AGC CGG GAA GAC CTG CTG GCA GAG GTG AGT GGG 6191
2028 D   S   L   D   V   Q   G   L   G   S   R   E   D   L   L   A   E   V   S   G   2047
6192 CCC TCC CCG CCC CTG GCC CGG GCC TAC TCT TTC TGG GGC CAG TCA AGT ACC CAG GCA CAG 6251
2048 P   S   P   P   L   A   R   A   Y   S   F   W   G   Q   S   S   T   Q   A   Q   2067
6252 CAG CAC TCC CGC AGC CAC AGC AAG ATC TCC AAG CAC ATG ACC CCG CCA GCC CCT TGC CCA 6311
2068 Q   H   S   R   S   H   S   K   I   S   K   H   M   T   P   P   A   P   C   P   2087
6312 GGC CCA GAA CCC AAC TGG GGC AAG GGC CCT CCA GAG ACC AGA AGC AGC TTA GAG TTG GAC 6371
2088 G   P   E   P   N   W   G   K   G   P   P   E   T   R   S   S   L   E   L   D   2107
6372 ACG GAG CTG AGC TGG ATT TCA GGA GAC CTC CTG CCC CCT GGC GGC CAG GAG GAG CCC CCA 6431
2108 T   E   L   S   W   I   S   G   D   L   L   P   P   G   G   Q   E   E   P   P   2127
6432 TCC CCA CGG GAC CTG AAG AAG TGC TAC AGC GTG GAG GCC CAG AGC TGC CAG CGC CGG CCT 6491
2128 S   P   R   D   L   K   K   C   Y   S   V   E   A   Q   S   C   Q   R   R   P   2147
6492 ACG TCC TGG CTG GAT GAG CAG AGG AGA CAC TCT ATC GCC GTC AGC TGC CTG GAC AGC GGC 6551
2148 T   S   W   L   D   E   Q   R   R   H   S   I   A   V   S   C   L   D   S   G   2167
6552 TCC CAA CCC CAC CTG GGC ACA GAC CCC TCT AAC CTT GGG GGC CAG CCT CTT GGG GGG CCT 6611
2168 S   Q   P   H   L   G   T   D   P   S   N   L   G   G   Q   P   L   G   G   P   2187
```

FIG. 6K

```
6612 GGG AGC CGG CCC AAG AAA AAA CTC AGC CCG CCT AGT ATC ACC ATA GAC CCC CCC GAG AGC  6671
2188 G   S   R   P   K   K   K   L   S   P   P   S   I   T   I   D   P   P   E   S    2207
6672 CAA GGT CCT CGG ACC CCG CCC AGC CCT GGT ATC TGC CTC CGG AGG AGG GCT CCG TCC AGC  6731
2208 Q   G   P   R   T   P   P   S   P   G   I   C   L   R   R   R   A   P   S   S    2227
6732 GAC TCC AAG GAT CCC TTG GCC TCT GGC CCC CCT GAC AGC ATG GCT GCC TCG CCC TCC CCA  6791
2228 D   S   K   D   P   L   A   S   G   P   P   D   S   M   A   A   S   P   S   P    2247
6792 AAG AAA GAT GTG CTG AGT CTC TCC GGT TTA TCC TCT GAC CCA GCA GAC CTG GAC CCC TGA  6851
2248 K   K   D   V   L   S   L   S   G   L   S   S   D   P   A   D   L   D   P   -    2267
6852 gtcctgccccactttcccactcacctttctccactgggtgc                                         6892
```

FIG. 6L

COMPARISON OF P-REGIONS

| I | | | II | | | III | | | IV | | | (SEQ ID NOS:38-43) |
|---|---|---|---|---|---|---|---|---|---|---|---|---|
| LAASE | E | GWVYV | QIITQ | E | GWTDF | ETLSF | K | GWNVI | RCLTG | E | DWNDI | *NIC-1 (C11D2.6)* |
| LAASQ | E | GWVYV | QIITQ | E | GWTDV | ETLSY | K | GWNVV | RSVTG | E | DWNDI | *NIC-2 (C27F2.3)* |
| EASSQ | E | GWVFL | QILTQ | E | GWVDV | EVLSL | K | GWVEV | RIVTG | E | DWNKI | *Rat -NIC* |
| QCITM | E | GWTDV | QILTG | E | DWNSV | TVSTF | E | GWPEL | RCATG | E | AWQDI | *L-Type Ca Channel* |
| QVITL | E | GWVDI | QILTQ | E | DWNKV | VLASK | D | GWVDI | RVSTG | D | NWNGI | *T-Type Ca Channel* |
| RLMTQ | D | FWENL | RVLCG | E | WIETM | QVATF | K | GWMDI | QITTS | A | GWDGL | *Na Channels* |

*FIG. 8*

NUCLEIC ACIDS ENCODING MAMMALIAN T-TYPE CALCIUM CHANNELS

CROSS-REFERENCE TO RELATED APPLICATIONS

This application is a divisional of application Ser. No. 09/611,257 filed 6 Jul. 2000 now U.S. Pat. No. 7,157,243, which is a continuation-in-part of application Ser. No. 09/346,794 filed 2 Jul. 1999 now U.S. Pat. No. 7,297,504. The disclosures of these applications are incorporated by reference herein.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing in identified on the electronically filed text file as follows:

| File Name | Date of Creation | Size (bytes) |
|---|---|---|
| 381092000710seqlist.txt | Apr. 9, 2007 | 159,945 bytes |

TECHNICAL FIELD

The invention relates to T-type calcium channel encoding sequences, expression of these sequences, and methods to screen for compounds which antagonize calcium channel activity. The invention is also related to molecular tools derived from knowledge of the molecular structure of T-type calcium channels.

BACKGROUND OF THE INVENTION

The rapid entry of calcium into cells is mediated by a class of proteins called voltage-gated calcium channels. Calcium channels are a heterogeneous class of molecules that respond to depolarization by opening a calcium-selective pore through the plasma membrane. The entry of calcium into cells mediates a wide variety of cellular and physiological responses including excitation-contraction coupling, hormone secretion and gene expression. In neurons, calcium entry directly affects membrane potential and contributes to electrical properties such as excitability, repetitive firing patterns and pacemaker activity. Miller, R. J., "Multiple calcium channels and neuronal function." *Science* (1987) 235:46-52. Calcium entry further affects neuronal functions by directly regulating calcium-dependent ion channels and modulating the activity of calcium-dependent enzymes such as protein kinase C and calmodulin-dependent protein kinase II. An increase in calcium concentration at the presynaptic nerve terminal triggers the release of neurotransmitter. Calcium entry also plays a role in neurite outgrowth and growth cone migration in developing neurons and has been implicated in long-term changes in neuronal activity.

In addition to the variety of normal physiological functions mediated by calcium channels, they are also implicated in a number of human disorders. Recently, mutations identified in human and mouse calcium channel genes have been found to account for several disorders including, familial hemiplegic migraine, episodic ataxia type 2, cerebellar ataxia, absence epilepsy and seizures. Fletcher, et al. (1996) "Absence epilepsy in tottering mutant mice is associated with calcium channel defects." *Cell* 87:607-617; Burgess, et al., "Mutation of the Ca2+ channel β subunit gene Cchb4 is associated with ataxia and seizures in the lethargic (1h) mouse." *Cell* (1997) 88:385-392; Ophoff, et al., "Familial hemiplegic migraine and episodic ataxia type-2 are caused by mutations in the Ca2+ channel gene CACNL1A4. " *Cell* (1996) 87:543-552; Zhuchenko, O., et al., "Autosomal dominant cerebellar ataxia (SCA6) associated with the small polyglutamine expansions in the α1A-voltage-dependent calcium channel." *Nature Genetics* (1997) 15:62-69.

The clinical treatment of some disorders has been aided by the development of therapeutic calcium channel antagonists. Janis, et al. (1991) in *Calcium Channels: Their Properties, Functions, Regulation and Clinical Relevance*. CRC Press, London.

Native calcium channels have been classified by their electrophysiological and pharmacological properties as T, L, N, P and Q types (for reviews see McCleskey, et al., "Functional properties of voltage-dependent calcium channels." *Curr. Topics Membr.* (1991) 39:295-326, and Dunlap, et al., "Exocytotic $Ca^{2+}$ channels in mammalian central neurons." *Trends Neurosci.* (1995) 18:89-98.). T-type (or low voltage-activated) channels describe a broad class of molecules that activate at negative potentials and are highly sensitive to changes in resting potential. The L, N, P and Q-type channels activate at more positive potentials and display diverse kinetics and voltage-dependent properties. There is some overlap in biophysical properties of the high voltage-activated channels, consequently pharmacological profiles are useful to further distinguish them. L-type channels are sensitive to dihydropyridine (DHP) agonists and antagonists, N-type channels are blocked by the *Conus geographus* peptide toxin, ω-conotoxin GVIA, and P-type channels are blocked by the peptide ω-agatoxin IVA from the venom of the funnel web spider, *Agelenopsis aperta*. A fourth type of high voltage-activated Ca channel (Q-type) has been described, although whether the Q- and P-type channels are distinct molecular entities is controversial (Sather, et al., "Distinctive biophysical and pharmacological properties of class A (B1) calcium channel α1 subunits." *Neuron* (1993) 11:291-303; Stea, et al., "Localization and functional properties of a rat brain α1A calcium channel reflect similarities to neuronal Q- and P-type channels." *Proc Natl Acad Sci* (*USA*) (1994) 91:10576-10580; Bourinet, E., et al., *Nature Neuroscience* (1999) 2:407-415). Several types of calcium conductances do not fall neatly into any of the above categories and there is variability of properties even within a category suggesting that additional calcium channels subtypes remain to be classified.

Biochemical analyses show that neuronal high-threshold calcium channels are heterooligomeric complexes consisting of three distinct subunits ($\alpha_1$, $\alpha_2\delta$ and β) (reviewed by De Waard, et al., in *Ion Channels*, (1997) Volume 4, edited by Narahashi, T. Plenum Press, New York). The a, subunit is the major pore-forming subunit and contains the voltage sensor and binding sites for calcium channel antagonists. The mainly extracellular Alternatively, the $\alpha_2$ subunit is disulphide-linked to the transmembrane δ subunit and both are derived from the same gene and are proteolytically cleaved in vivo. The β subunit is a non-glycosylated, hydrophilic protein with a high affinity of binding to a cytoplasmic region of the $\alpha_1$ subunit. A fourth subunit, γ, is unique to L-type Ca channels expressed in skeletal muscle T-tubules. The isolation and characterization of γ-subunit-encoding cDNAs is described in U.S. Pat. No. 5,386,025 which is incorporated herein by reference.

Molecular cloning has revealed the cDNA and corresponding amino acid sequences of six different types of $\alpha_1$ subunits ($\alpha_{1A}$, $\alpha_{1B}$, $\alpha_{1C}$, $\alpha_{1D}$, $\alpha_{1E}$ and $\alpha_{1S}$) and four types of β subunits ($\beta_1$, $\beta_2$, $\beta_3$ and $\beta_4$) (reviewed in Stea, A., Soong, T. W. and Snutch, T. P. (1994) "Voltage-gated calcium channels." in *Handbook of Receptors and Channels*. Edited by R. A. North, CRC Press). A comparison of the amino acid sequences of these $\alpha_1$ subunits is included in this publication, which is incorporated herein by reference. PCT Patent Publication WO 95/04144, which is incorporated herein by reference, discloses the sequence and expression of as $\alpha_{1E}$ calcium channel subunits.

As described in Stea, A., et al. (1994) (supra), the $\alpha_1$ subunits are generally of the order of 2000 amino acids in length, ranging from 1873 amino acids in $\alpha_{1S}$ derived from rabbit to 2424 amino acids in $\alpha_{1A}$ derived from rabbit. Generally, these subunits contain 4 internal homologous repeats (I-IV) each having six putative alpha helical membrane spanning segments (S1-S6) with one segment (S4) having positively charged residues every 3rd or 4th amino acid. There are a minority of a splice variant exceptions. Between domains II and III there is a cytoplasmic domain which is believed to mediate excitation-contraction coupling in $\alpha_{1S}$ and which ranges from 100-400 amino acid residues among the subtypes. The domains I-IV make up roughly ⅔ of the molecule and the carboxy terminus adjacent to the S6 region of domain IV is believed to be on the intracellular side of the calcium channel. There is a consensus motif (QQ-E-L-GY-WI-E) (SEQ ID NO:44) in all of the subunits cloned and described in Stea, A., et al. (supra) downstream from the domain I S6 transmembrane segment that is a binding site for the β subunit.

PCT publication WO 98/38301, which describes the work of the inventors herein, and which is incorporated herein by reference, reports the first description of the molecular composition of T-type calcium channel $\alpha_1$ subunits. The present application describes full-length genes for 3 mammalian subtypes, $\alpha_{1G}$, $\alpha_{1H}$, and $\alpha_{1I}$ associated with T-type calcium channels.

In some expression systems the high threshold $\alpha_1$ subunits alone can form functional calcium channels although their electrophysiological and pharmacological properties can be differentially modulated by coexpression with any of the four β subunits. Until recently, the reported modulatory affects of β subunit coexpression were to mainly alter kinetic and voltage-dependent properties. More recently it has been shown that β subunits also play crucial roles in modulating channel activity by protein kinase A, protein kinase C and direct G-protein interaction. (Bourinet, et al., "Voltage-dependent facilitation of a neuronal α1C L-type calcium channel." *EMBO J* (1994) 13:5032-5039; Stea, et al., "Determinants of PKC-dependent modulation of a family of neuronal calcium channels," *Neuron* (1995) 15:929-940; Bourinet, et al., "Determinants of the G-protein-dependent opioid modulation of neuronal calcium channels." *Proc. Natl. Acad. Sci. (USA)* (1996) 93:1486-1491.)

Because of the importance of calcium channels in cellular metabolism and human disease, it would be desirable to identify the remaining classes of $\alpha_1$ subunits, and to develop expression systems for these subunits which would permit the study and characterization of these calcium channels, including the study of pharmacological modulators of calcium channel function.

DISCLOSURE OF THE INVENTION

The present invention provides sequences for a novel mammalian calcium channel subunits of T-type calcium channels, which we have labeled as $\alpha_{1G}$, $\alpha_{1H}$ and $\alpha_{1I}$ subunits. Knowledge of the sequences of these calcium channel subunits may be used in the development of probes for mapping the distribution and expression of the subunits in target tissues. In addition, as the molecular structure of the $\alpha_1$ subunits of these T-type calcium channels has been elucidated, it is possible to identify those portions which reside extracellularly and thus to design peptides to elicit antibodies which can be employed to assess the location and level of expression of T-type calcium channels. In addition, these subunits, either alone or assembled with other proteins, can produce functional calcium channels, which can be evaluated in model cell lines to determine the properties of the channels containing the subunits of the invention. These cell lines can be used to evaluate the effects of pharmaceuticals and/or toxic substances on calcium channels incorporating $\alpha_{1G}$, $\alpha_{1H}$ and $\alpha_{1I}$ subunits. The resulting identified compounds are useful in treating conditions where undesirable T-type calcium channel activity is present. These conditions include epilepsy, sleep disorders, mood disorders, cardiac hypertrophy and arrhythmia and hypertension, among others. In addition, antisense and triplex nucleotide sequences can be designed to inhibit the production of T-type calcium channels.

In a preferred embodiment the $\alpha_1$ subunits are other than those encoded by SEQ. ID. NO: 17; in another preferred embodiment the $\alpha_1$ subunits are other than those encoded by sequences that include SEQ. ID. NO: 19 and SEQ. ID. NO: 21. In another preferred embodiment, probes representing portions of or all of SEQ. ID. NOS. 1-22 or 13-21 are excluded.

BRIEF DESCRIPTION OF THE DRAWINGS

FIGS. 6A to 6L show the nucleotide and deduced amino acid sequence of human T-type calcium channel $\alpha_{1G}$.

FIG. 8 shows the characteristic pore pattern for T-type channels.

MODES OF CARRYING OUT THE INVENTION

Figure 1A:
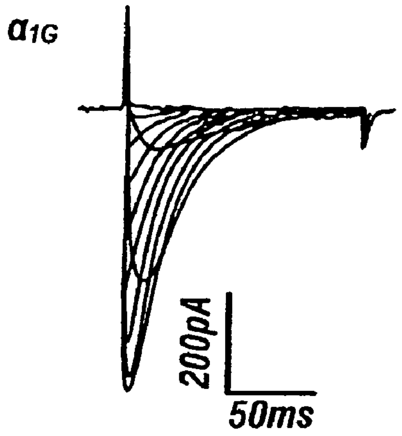
FIGS. 1A and B show a comparison of the waveforms and current voltage relationship for $\alpha_{1G}$.
Figure 1B:
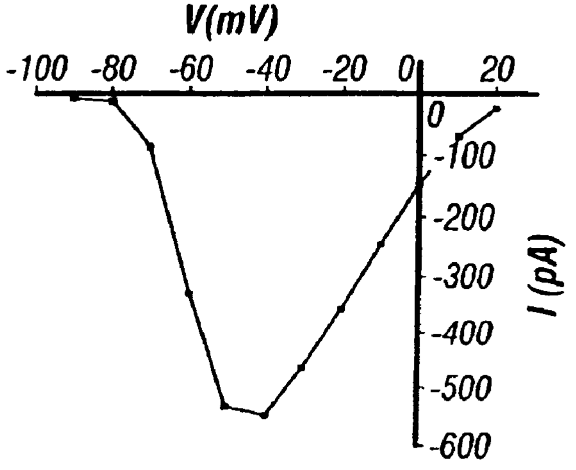
Figure 2A:
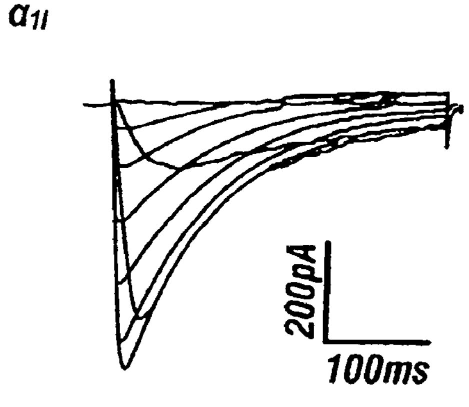
FIGS. 2A and B show a comparison of the waveforms and current voltage relationship for $\alpha_{1I}$ calcium channels.
Figure 2B:
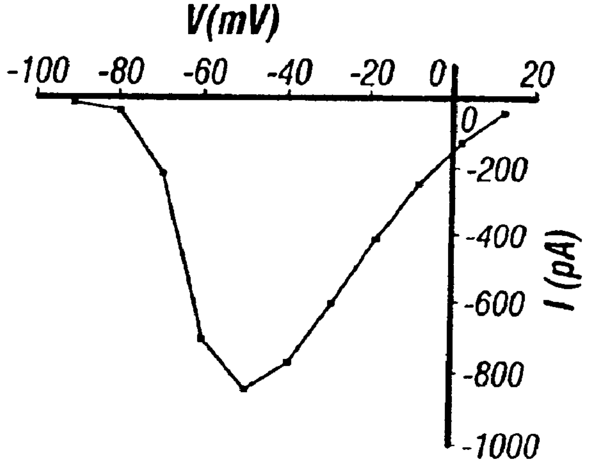

The present invention includes the following aspects for which protection is sought:

(a) novel mammalian (including human) calcium channel subunits and DNA sequences encoding such subunits. Specifically, the invention encompasses an at least partially purified DNA molecule comprising a sequence of nucleotides that encodes an $\alpha_1$ subunit of a T-type calcium channel, and such α subunits per se. It will be appreciated that polymorphic variations may be made or may exist in the DNA of some individuals leading to minor deviations in the DNA or amino acids sequences from those shown which do not lead to any substantial alteration in the function of the calcium channel. Such variations, including variations which lead to substitutions of amino acids having similar properties are considered to be within the scope of the present invention. Thus, in one embodiment, the present application claims DNA molecules which encode $\alpha_1$ subunits of mammalian T-type calcium channels, and which hybridize under conditions of medium (or higher) hybridization stringency with one or another of the specific sequences disclosed in this application. This level of hybridization stringency is generally sufficient given the length of the sequences involved to permit recovery of the subunits within the scope of the invention from mammalian DNA libraries.

Alternatively, the T-type calcium channels of the invention are recognized by their functional characteristic of low voltage gating along with defined structural characteristics which classify them as $\alpha_1$ calcium channel subunits and also characterize them as of the T-type. By virtue of the present invention, these characteristics have been elucidated as follows:

One distinguishing feature of the α1G, α1H and α1I T-type channels over other types of calcium channels and sodium channels is that the pore region (P-region) in each of the four structural domains contains a diagnostic amino acid sequence implicated in channel permeability. FIG. 8 shows that the T-type channels contain the residues glutamate/glutamate/aspartate/asparate (single letter amino acid code: EEDD (SEQ ID NO:45)) in the P-regions of domains I-IV. In contrast, FIG. 8 shows that in sodium (Na) channels the P-region of the four domains contains the residues: aspartate/glutamate/lysine/alanine (single letter amino acid code: DEKA (SEQ ID NO:46)), while high threshold calcium channels such as the L-type channel contain the residues: glutamate/glutamate/glutamate/glutamate (single letter amino acid code: EEEE (SEQ ID NO:47)). The α1G, α1H and α1I T-type channels are also distinct in this region compared to other types of ion channels including the *C. elegans* C11D2.6 and C27F2.3 and the rat NIC-channel (FIG. 8).

A second distinguishing characteristic of the $\alpha_{1G}$, $\alpha_{1H}$ and $\alpha 1_1$ T-type channels compared to other types of calcium channels is that they do not contain a β subunit binding consensus sequence in the cytoplasmic linker separating domains I and II. In contrast, all high threshold calcium channels contain a consensus sequence (single letter amino acid code: QQ-E--L-GY--WI---E) (SEQ ID NO:44) shown to physically interact with the calcium channel β subunit (Pragnell, M., De Waard, M., Mori, Y., Tanabe, T., Snutch, T. P. & Campbell, K. P., 1994, Nature 368:67-70). Thus it appears the presence of a β subunit does not modify activity, nor is its presence required.

A third distinguishing characteristic of the ($\alpha_{1G}$, $\alpha_{1H}$ and $\alpha_{1I}$ T-type channels is that they do not possess an EF-hand calcium binding motif in the region carboxyl to domain IV S6. In contrast, all high threshold calcium channels contain a consensus sequence that is closely related to the EF-hand domain found in certain calcium binding proteins (de Leon, M., Wang, Y., Jones, L., Perez-Reyes, E., Wei, X., Soong, T. W., Snutch, T. P. & Yue, D.T., *Science* (1995) 270:1502-1506).

Thus, as defined herein, "T-type calcium channel $a_1$ subunits" refers to subunits which contain these structural characteristics.

Alternatively, the T-type $\alpha_1$ subunit molecules can be defined by homology to the human and rat nucleotide and amino acid sequences described herein. Thus, T-type $\alpha_1$ subunits will typically have at least 50%, preferably 70% homology in terms of amino acid sequence or encoding nucleotide sequence to the sequences set forth in SEQ ID NOS. 23-28 herein or those shown in FIG. 6A-6L. Preferably, the homology will be at least 80%, more preferably 90%, and most preferably 95%, 97%, 98% or 99%.

Relative homology may also be defined in terms of specific regions; as set forth above, certain regions of T-type channel $\alpha_1$ subunits have very high homologies while other regions, such as the cytoplasmic region between domains II and III have less homology. Thus, T-type $\alpha_1$ subunits will have over 75% homology; preferably over 85% or over 95% homology, more preferably over 98% homology in domains I-IV to those of SEQ. ID. NOS. 23-28 or FIG. 6A-6L. The degree of homology in the cytoplasmic region between domains II and III may be substantially less, e.g., only 25% homology, preferably, 50% homology or more preferably 60% homology. Similarly, the intracellular region downstream of domain IV may be less homologous than within domains I-IV.

(b) polynucleotide sequences useful as probes in screening human cDNA libraries for genes encoding these novel calcium channel subunits. These probes can also be used in histological assay to determine the tissue distribution of the novel calcium channel subunits.

As set forth above, the elucidation herein of the structural features of T-type subunits permits the selection of appropriate probes by selecting portions of the encoding nucleotide sequence that are particularly characteristic of this type. As set forth above, for example, T-type subunits have particular patterns of amino acids in the pore forming units as set forth in FIG. 8. Alternatively, multiple probes might be used to distinguish other subunits, such as probes which represent the β-binding domain missing from the T-type $\alpha_1$ subunits combined with a probe representing a consensus sequence for calcium channel α subunits in general.

(c) at least partially purified a, subunits and related peptides for mammalian T-type calcium channels. These proteins and peptides can be used to generate polyclonal or monoclonal antibodies to determine the cellular and subcellular distribution of T-type calcium channel subunits.

Again, by virtue of the elucidation of the amino acid sequence of T-type $\alpha_1$ subunits, it is well within the ordinary skill in the art to determine which regions of the channel are displayed extracellularly and to select these regions for the generation of antibodies.

(d) eukaryotic cell lines expressing the novel calcium channel subunits. These cell lines can be used to evaluate compounds as pharmacological modifiers of the function of the novel calcium channel subunits.

(e) a method for evaluating compounds as pharmacological modifiers of the function of the novel calcium channel subunits using the cell lines expressing those subunits alone or in combination with other calcium channel subunits.

(f) Use of the compounds identified as set forth above for the treatment of conditions which are associated with undesired calcium channel activity.

These diseases include, but are not limited to; epilepsy, migraine, ataxia, schizophrenia, hypertension, arrhythmia, angina, depression, and Parkinson's disease; characterization of such associations and ultimately diagnosis of associated diseases can be carried out with probes which bind to the wild-type or defective forms of the novel calcium channels.

T-type channels in particular are responsible for rebound burst firing in central neurons and are implicated in normal brain functions such as slow-wave sleep and in neurological disorders such as epilepsy and mood disorders. They are also important in pacemaker activity in the heart, hormone secretion and fertilization, and are associated with disease states such as cardiac hypertrophy and hypertension.

As used in the specification and claims of this application, the term "T-type calcium channel" refers to a voltage-gated calcium channel having a low activation voltage, generally less than −50 mV, and most commonly less than −60 mV. T-type calcium channels also exhibit comparatively negative steady-state inactivation properties and slow deactivation kinetics. The terms "$\alpha_1$ subunit" or "$\alpha_1$ calcium channel" refer to a protein subunit of a calcium channel which is responsible for pore formation and contains the voltage sensor and binding sites for calcium channel agonists and antagonists. Such subunits may be independently functional as calcium channels or may require the presence of other subunit types for complete functionality.

As used in the specification and claims of this application, the phrase "at least partially purified" refers to DNA or protein preparations in the which the specified molecule has been separated from adjacent cellular components and molecules with which it occurs in the natural state, either by virtue of performing a physical separation process or by virtue of making the DNA or protein molecule in a non-natural environment in the first place. The term encompasses cDNA molecules and expression vectors.

In accordance with the present invention, we have identified mammalian DNA sequences which code for novel T-type calcium channel a, subunits. These subunits are believed to represent new types of $\alpha_1$ subunits of mammalian voltage-dependent calcium channels which have been designated as types $\alpha_{1G}$, $\alpha_{1H}$ and $\alpha_{1I}$.

A Bacterial Artificial Chromosome (BAC) sequence (bK206c7) was identified from sequences in Sanger Genome Sequencing Center (Cambridge, U.K.) and the Washington University Genome Sequencing Center (St. Louis. Mo.) that contains a nucleotide sequence encoding the $\alpha_{1I}$ subunit of human T-type calcium channel. The rationale for this identification is set forth in WO 98/38301, incorporated herein by reference. The relevant nucleotide sequence and the translated amino acid sequence containing 1854 amino acids are set forth in SEQ ID NOS: 17 and 18.

As described in WO 98/38031, using PCR cloning techniques to identify relevant sequences within a human brain total RNA preparation, we confirmed that the novel $\alpha_{1I}$ calcium channel subunit is present in human brain. Subcloning of the 567 nt PCR product (SEQ. ID NO: 19, amino acids SEQ. ID NO: 20) and subsequent sequencing thereof showed that this product corresponds to the derived sequence from the bK206c7 BAC genomic sequence, the nucleotide sequence of which is given as SEQ ID NO: 17 (amino acid sequence SEQ. ID NO: 18). The same experiment was performed using a rat brain RNA preparation and resulted in recovery of a substantially identical PCR product. (SEQ ID. NO: 21). The protein encoded by the rat PCR product (SEQ ID NO: 22) is 96% identical to the human PCR product (SEQ. ID NO: 20).

These sequences, which encode a partial subunit were used as a basis for constructing full length human or rat $\alpha_{1I}$ clones. Briefly, the subcloned $\alpha_{1I}$ PCR product is radiolabeled by random hexamer priming according to standard methods (See, Sambrook, J., Fritsch, E. F., and Maniatis, T., (1989) *Molecular Cloning, A Laboratory Manual*. Cold Spring Harbor Press) and used to screen commercial human brain cDNA libraries (Stratagene, La Jolla, Calif.). The screening of cDNA libraries follows standard methods and includes such protocols as infecting bacteria with recombinant lambda phage, immobilizing lambda DNA to nitrocellulose filters and screening under medium hybridization stringency conditions with radiolabeled probe. cDNA clones homologous to the probe are identified by autoradiography. Positive clones are purified by sequential rounds of screening.

Following this protocol, most purified cDNA's are likely to be partial sequence clones due the nature of the cDNA library synthesis. Full length clones are constructed from cDNA's which overlap in DNA sequence. Restriction enzyme sites which overlap between cDNAs are used to ligate the individual cDNA's to generate a full-length cDNA. For subsequent heterologous expression, the full-length cDNA is subcloned directly into an appropriate vertebrate expression vector, such as pcDNA-3 (Invitrogen, San Diego, Calif.) in which expression of the cDNA is under the control of a promoter such as the CMV major intermediate early promoter/enhancer. Other suitable expression vectors include, for example, pMT2, pRC/CMV, pcDNA3.1 and pCEP4.

Following these protocols, full length mammalian $\alpha_{1G}$, $\alpha_{1H}$ and $\alpha_{1I}$ calcium channel subunit cDNAs were isolated by using the 567 base pair human fragment (SEQ. ID NO. 19) to screen a rat brain cDNA library. Sequencing of the recovered sequences identified the three distinct classes of calcium channel subunits which have been denominated herein as $\alpha_{1G}$, $\alpha_{1H}$ and $\alpha_{1I}$ subunits. For each class of subunit, complete sequencing of the largest cDNA confirmed that it represented only a portion of the predicted calcium channel coding region. Complete sequences for the three new subunits were obtained by rescreening the rat brain cDNA library with probes derived from the partial length cDNAs to obtain overlapping segments. These segments were combined to form a complete gene by restriction digestion and ligation. The complete cDNA sequences of the rat $\alpha_{1G}$, $\alpha_{1H}$ and $\alpha_{1I}$ subunits are given by SEQ. ID NOS. 23, 25 and 27, respectively. Corresponding amino acid sequences are given by SEQ. ID NOS. 24, 26 and 28. The same techniques are employed to recover human sequences by screening of a human or other mammalian library. Thus, for example, partial length human sequences for $\alpha_{1G}$ and $\alpha_{1H}$ T-type calcium channels have been recovered using the same probe (SEQ. ID NO. 19) and the full length rat $\alpha_{1I}$ cDNA (SEQ. ID. NO. 27) has been used to recover a partial length DNA encoding a human $\alpha_{1I}$ T-type calcium channel. The DNA and amino acid sequences for these partial length human calcium channels are given by SEQ. ID NOS. 30-35. A complete coding sequence for human $\alpha_{1G}$ was also obtained and is set forth, along with the deduced amino acid reference, in FIG. 6A-6L.

Once the full length cDNA is cloned into an expression vector, the vector is then transfected into a host cell for expression. Suitable host cells include *Xenopus oocytes* or mammalian cells such as human embryonic kidney cells as described in International Patent Publication No. WO 96/39512 which is incorporated herein by reference and Ltk cells as described in U.S. Pat. No. 5,386,025 which is incorporated herein by reference. Transfection into host cells may be accomplished by microinjection, lipofection, glycerol shock, electroporation calcium phosphate or particle-mediated gene transfer. The vector may also be transfected into host cells to provide coexpression of the novel $\alpha_1$ subunits with other $\alpha$ subunits, such as an $\alpha_2\delta$ subunit or $\gamma$ subunit.

To confirm that the three full length cDNAs (SEQ. ID NOS: 23, 25 and 27) encoded functional calcium channels, the $\alpha_{1G}$ and $\alpha_{1I}$ cDNAs were transiently transfected into human embryonic kidney cells and evaluated using electrophysiological recording techniques. The results are consistent with a role of these subunits in native T-type channels in nerve, muscle and endocrine cells. Similarly, a full length clone encoding human $\alpha_{1G}$ T-type subunit was recovered and verified to have the characteristic properties of T-type channels.

The resulting cell lines expressing functional calcium channels including the novel $\alpha_1$ subunits of the invention can be used test compounds for pharmacological activity with respect to these calcium channels. Thus, the cell lines are useful for screening compounds for pharmaceutical utility. Such screening can be carried out using several available methods for evaluation of the interaction, if any, between the test compound and the calcium channel. One such method involves the binding of radiolabeled agents that interact with the calcium channel and subsequent analysis of equilibrium binding measurements including but not limited to, on rates, off rates, $K_d$ values and competitive binding by other molecules. Another such method involves the screening for the effects of compounds by electrophysiological assay whereby individual cells are impaled with a microelectrode and currents through the calcium channel are recorded before and after application of the compound of interest. Another method, high-throughput spectrophotometric assay, utilizes the loading the cell lines with a fluorescent dye sensitive to intracellular calcium concentration and subsequent examination of the effects of compounds on the ability of depolarization by potassium chloride or other means to alter intracellular calcium levels. Compounds to be tested as agonists or antagonists of the novel $\alpha_{1I}$ calcium channel subunits are combined with cells that are stably or transiently transformed with a DNA sequence encoding the $\alpha_{1G}$, $\alpha_{1H}$ and $\alpha_{1I}$ calcium channel subunits of the invention and monitored using one of these techniques.

Compounds which are shown to modulate the activity of calcium channels can then be used in pharmaceutical compositions for the treatment associated with inappropriate T-type calcium channel activity. Such conditions may also include those with inappropriate calcium channel activity in general since such activity may be modified by enhancing or decreasing T-type channel activity. Conditions appropriate for such treatment include those set forth above. The compounds identified are formulated in conventional ways as set forth in Remington's "Pharmaceutical Sciences," latest edition, Mac Publishing Co., Easton, Pa. Modes of administration are those appropriate for the condition to be treated and are within the ordinary skill of the practitioner.

In addition, the regulation of expression of T-type calcium channels can be achieved by constructing expression systems encoding antisense sequences or sequences designed for triplex binding to interrupt the expression of nucleotide sequences encoding the T-type calcium channels of the invention.

DNA fragments with sequences given by SEQ ID NOS. 13-17 and 19, or polynucleotides with the complete coding sequences as given by SEQ ID NOS. 23, 25 and 27 or FIG. 6 or distinctive portions thereof which do not exhibit non-discriminatory levels of homology with other types of calcium channel subunits may also be used for mapping the distribution of $\alpha_{1G}$, $\alpha_{1H}$ and $\alpha_{1I}$ calcium channel subunits within a tissue sample. This method follows normal histological procedures using a nucleic acid probe, and generally involves the steps of exposing the tissue to a reagent comprising a directly or indirectly detectable label coupled to a selected DNA fragment, and detecting reagent that has bound to the tissue. Suitable labels include fluorescent labels, enzyme labels, chromophores and radio-labels.

Heterologous Expression of Mammalian T-type Calcium Channels in Cells

A. Transient Transfection in Mammalian Cells

Host cells, such as human embryonic kidney cells, HEK 293 (ATCC# CRL 1573) are grown in standard DMEM medium supplemented with 2 mM glutamine and 10% fetal bovine serum. HEK 293 cells are transfected by a standard calcium-phosphate-DNA co-precipitation method using a full-length mammalian $\alpha_1$ T-type calcium channel cDNA (for example, SEQ. ID. NO: 27) in a vertebrate expression vector (for example see Current protocols in Molecular Biology). The $\alpha_{1I}$ calcium channel cDNA may be transfected alone or in combination with other cloned subunits for mammalian calcium channels, such as $\alpha 2\delta$ and $\beta$ or $\gamma$ subunits, and also with clones for marker proteins such the jellyfish green fluorescent protein.

Electrophysiological Recording: After an incubation period of from 24 to 72 hrs the culture medium is removed and replaced with external recording solution (see below). Whole cell patch clamp experiments are performed using an Axopatch 200B amplifier (Axon Instruments, Burlingame, Calif.) linked to an IBM compatible personal computer equipped with pCLAMP software. Microelectrodes are filled with 3 M CsCl and have typical resistances from 0.5 to 2.5 Mohms. The external recording solution is 2 mM $BaCl_2$. 1 mM $MgCl_2$, 10 mM HEPES, 40 mM TEACl, 10 mM Glucose, 92 mM CsCl, (pH 7.2). The internal pipette solution is 105 mM CsCl, 25 mM TEACl, 1 mM $CaCl_2$, 11 mM EGTA, 10 mM HEPES (pH 7.2). Currents are typically elicited from a holding potential of −100 mV to various test potentials. Data are filtered at 1 kHz and recorded directly on the hard-drive of a personal computer. Leak subtraction is carried out on-line using a standard P/5 protocol. Currents are analyzed using pCLAMP versions 5.5 and 6.0. Macroscopic current-voltage relations are fitted with the equation $I=\S 1/(1+\exp(-(V_m-V_h)/S)\}\times G-(V_m-E_{rev})$, where $V_m$ is the test potential, $V_h$ is the voltage at which half of the channels are activated, and S reflects the steepness of the activation curve and is an indication of the effective gating charge movement. Inactivation curves are normalized to 1 and fitted with $I=(1/1+\exp((V_m-V_h)/S)$ with $V_m$ being the holding potential. Single channel recordings are performed in the cell-attached mode with the following pipette solution (in mM): 100 $BaCl_2$, 10 HEPES, pH 7.4 and bath solution: 100 KCl, 10 EGTA, 2 $MgCl_2$, 10 HEPES, pH 7.4.

B. Transient Transfection in *Xenopus* Oocytes

Stage V and VI *Xenopus* oocytes are prepared as described by Dascal, et al., "Expression and modulation of voltage-gated calcium channels after RNA injection into *Xenopus* oocytes" *Science* (1986) 231:1147-1150. After enzymatic dissociation with collagenase, oocytes nuclei are microinjected with the human $\alpha_{1I}$ calcium channel cDNA expression vector construct (approximately 10 ng DNA per nucleus) using a Drummond nanoject apparatus. The $\alpha_{1I}$ calcium channel may be injected alone, or in combination with other mammalian calcium channel subunit cDNAs, such as the $\alpha 2$-$\delta$ and $\beta 1b$ and $\gamma$ subunits. After incubation from 48 to 96 hrs macroscopic currents are recorded using a standard two microelectrode voltage-clamp (Axoclamp 2A, Axon Instruments, Burlingame, Calif.) in a bathing medium containing (in mM): 40 Ba(OH)2, 25 TEA-OH, 25 NaOH, 2 CsOH, 5 HEPES (pH titrated to 7.3 with methane-sulfonic acid). Pipettes of typical resistance ranging from 0.5 to 1.5 Mohms are filled with 2.8M CsCl, 0.2M CsOH, 10 mM HEPES, 10 mM BAPTA free acid. Endogenous Ca (and Ba)-activated Cl currents are suppressed by systematically injecting 10-30 nl of a solution containing 100 mM BAPTA-free acid, 10 mM HEPES (pH titrated to 7.2 with CsOH) using a third pipette connected to a pneumatic injector. Leak currents and capacitive transients are subtracted using a standard P/5 procedure.

Construction of Stable Cell Lines Expressing Mammalian T-type Calcium Channels

Mammalian cell lines stably expressing human $\alpha_{1I}$ calcium channels are constructed by transfecting the $\alpha_{1I}$ calcium channel cDNA into mammalian cells such as HEK 293 and selecting for antibiotic resistance encoded for by an expression vector. Briefly, a full-length mammalian T-type calcium channel $\alpha 1$ subunit cDNA (for example SEQ. ID NO: 27) subcloned into a vertebrate expression vector with a selectable marker, such as the pcDNA3 (InvitroGen, San Diego, Calif.), is transfected into HEK 293 cells by calcium phosphate coprecipitation or lipofection or electroporation or other method according to well known procedures (Methods in Enzymology, Volume 185, Gene Expression Technology (1990) Edited by Goeddel, D. V.). The $\alpha_{1I}$ calcium channel may be transfected alone, or in combination with other mammalian calcium channel subunit cDNAs, such as the $\alpha 2$-$\delta$ and $\beta 1b$ subunits, either in a similar expression vector or other type of vector using different selectable markers. After incubation for 2 days in nonselective conditions, the medium is supplemented with Geneticin (G418) at a concentration of between 600 to 800 ug/ml. After 3 to 4 weeks in this medium, cells which are resistant to G418 are visible and can be cloned as isolated colonies using standard cloning rings. After growing up each isolated colony to confluency to establish cell lines, the expression of $\alpha_{1I}$ calcium channels can be determined at with standard gene expression methods such as Northern blotting, RNase protection and reverse-transcriptase PCR.

The functional detection of $\alpha_{1I}$ calcium channels in stably transfected cells can be examined electrophysiologically, such as by whole patch clamp or single channel analysis (see above). Other means of detecting functional calcium channels include the use of radiolabeled $^{45}Ca$ uptake, fluorescence spectroscopy using calcium sensitive dyes such as FURA-2, and the binding or displacement of radiolabeled ligands that interact with the calcium channel.

EXAMPLE 1

Partial Rat and Human Subunits

In order to recover mammalian sequences for novel calcium channels, the 567 base pair partial length human brain $\alpha_{1I}$ cDNA described in WO 98/3801 was gel-purified, radiolabeled with $^{32}p$ dATP and dCTP by random priming (Feinberg, et al., 1983, *Anal. Biochem.* 132: 6-13) and used to screen a rat brain cDNA library constructed in the phase vector Lambda Zapp II. (Snutch et al., 1990, *Proc Natl Acad Sci* (*USA*) 87: 3391-3395). Screening was carried out at 62° C. in 5×SSPE (1×SSPE=0.18 M NaCl; 1 mM EDTA; 10 mM sodium phosphate, pH=7.4 0.3% SDS, 0.2 mg/ml denatured salmon sperm DNA). Filters were washed at 62° C. in 0.2×SSPE/0.1% SDS. After three rounds of screening and plaque purification, positive phages were transformed into Bluescript phagemids (Stratagene, La Jolla, Calif.) by in vivo excision.

Double stranded DNA sequencing on the recombinant phagemids was performed using a modified dideoxynucleotide protocol (Biggin et al., 1983, *Proc Natl Acad Sci* (*USA*) 80:3963-3965) and Sequenase version 2.1 (United States Biochemical Corp.). DNA sequencing identified three distinct classes of calcium channel $\alpha_1$ subunits: designated as $\alpha_{1G}$, $\alpha_{1H}$ and $\alpha_{1I}$ calcium channel subunits.

For each class of calcium channel $\alpha_1$ subunit, the largest cDNA was completely sequenced and determined to represent only a portion of the predicted calcium channel coding region. In order to isolate the remaining portions of $\alpha_{1G}$ and $\alpha_{1I}$ calcium channel subunits, the $\alpha_{1G}$ clone was digested with HindIII and SpeI. The resulting 540 base pair fragment was gel purified, radiolabeled with $^{32}P$ dATP and dCTP by random priming and used to rescreen the rat brain cDNA library as described above. The sequence of the 540 base pair $\alpha_{1G}$ screening probe used is given by SEQ. ID NO: 29. Other sequences spanning regions of distinctiveness within the sequences for the subunits could also be employed.

Double-stranded DNA sequencing of the purified recombinant phagemids showed that additional $\alpha_{1G}$, $\alpha_{1H}$ and $\alpha_{1I}$ calcium channel subunit cDNAs overlapped with the original partial length cDNAs and together encoded complete protein coding regions as well as portions of their respective 5' and 3' non-coding untranslated regions.

To recover further human sequences for the novel $\alpha_{1G}$ and $\alpha_{1H}$ calcium channels, the 567 base pair partial length human brain $\alpha_{1I}$ cDNA (SEQ. ID. NO: 19) was radio-labeled with $^{32}P$ dATP and dCTP by random priming and used to screen a commercial human thalamus cDNA library (Clontech). Hybridization was performed overnight at 65° C. in 6×SSPE; 0.3% SDS; 5×Denhardt's. Filters were washed at 65° C. in 0.1×SSPE/0.3% SDS. After four rounds of screening and plaque purification, positive phages were selected, DNA prepared and the insert cDNA excised from the lambda vector by digestion with Eco R1 restriction enzyme. The excised cDNA was subdloned into the plasmid Bluescript KS (Stratagene, La Jolla, Calif.) and the DNA sequence determined using a modified dideoxynucleotide protocol and Sequence version 2.1. The partial length $\alpha_{1G}$ cDNA isolated consisted of 2212 base pairs of which 279 base pairs were 5' noncoding and 1,933 base pairs were coding region representing 644 amino acids (SEQ. ID NOS. 30, 31). The partial $\alpha_{1H}$ cDNA isolated consisted of 1,608 base pairs of which 53 base pairs were 5' noncoding and 1,555 were coding region representing 518 amino acids (SEQ. ID NOS. 32, 33).

To recover further human sequences for the novel $a_{1I}$ calcium channel, the full-length rat brain $\alpha_{1I}$ cDNA (SEQ. ID. NO: 27) (See Example 2) was radio-labeled $^{32}P$ dATP and dCTP by random priming and used to screen a commercial human hippocampus cDNA library (Stratagene). Hybridization was performed overnight at 65° C. in 6×SSPE; 0.3% SDS; 5×Denhardt's. Filters were washed at 65° C. in 0.1×SSPE/0.3% SDS. After four rounds of screening and plaque purification, positive phages were transformed into Bluescript phagemids (Stratagene, LA Jolla, Calif.) by in vitro excision. The excised cDNA DNA sequence was determined using a modified dideoxynucleotide protocol and Sequenase version 2.1. The partial $\alpha_{1I}$ cDNA isolated consisted of 1,080 base pairs of coding region representing 360 amino acids (SEQ. ID NOS. 34,35).

EXAMPLE 2

Full Length Rat Subunits

Double-stranded DNA sequencing of the purified recombinant phagemids from rat brain showed that additional $\alpha_{1G}$ and $\alpha_{1I}$ calcium channel cDNAs overlapped with the original partial length cDNAs and together encoded complete protein coding regions as well as portions of their respective 5' and 3' non-coding untranslated regions (SEQ. ID NOS. 23 and 27, respectively). In addition to the $\alpha_{1G}$ and $\alpha_{1I}$ calcium channel classes, DNA sequencing of the recombinant phagemids also identified a third class of calcium channel $\alpha_1$ subunit: designated as the $\alpha_{1H}$ calcium channel subunit. The partial length $\alpha_{1H}$ calcium channel cDNAs overlapped and together encoded a complete $\alpha_{1H}$ coding region as well as portions of the 5' and 3' untranslated regions (SEQ. ID. NO: 25).

Electrophysiological studies were performed on transiently-transfected human embryonic kidney cells (HEK-tsa201) prepared using the general protocol above. Transfection was carried out by standard calcium phosphate precipitation. (Okayama, et al., 1991, *Methods in Molec. Biol.*, Vol. 7, ed. Murray, E. J.). For maintenance, HEK-tsa201 cells were cultured until approximately 70% confluent, the media removed and cells dispersed with trypsin and gentle trituration. Cells were then diluted 1:10 in culture medium (10% FBS, DMEM plus L-glutamine, pen-strp) warmed to 37° C. and plated onto tissue culture dishes. For transient transfection, 0.5 mM $CaCl_2$ was mixed with a total of 20 μg of DNA (consisting of 3 μg of either rat brain $\alpha_{1G}$ or $\alpha_{1I}$ calcium channel cDNA, 2 μg of CD8 plasmid marker, and 15 μg of Bluescript plasmid carrier DNA). The DNA mixture was mixed thoroughly and then slowly added dropwise to 0.5 ml of 2 times HeBS (274 mM NaCl, 20 mM D-glucose, 10 mM KCl, 1.4 mM $Na_2HPO_4$, 40 mM Hepes (pH=7.05). After incubation at room temperature for 20 min, 100 μl of the DNA mixture was slowly added to each dish of HEK-tsa201 cells and then incubated at 37° C. for 24 to 48 hours in a tissue culture incubator (5% $CO_2$).

Positive transfectant cells were identified visually by addition of 1 μl of mouse CD8 (Lyt2) Dynabeads directly to the recording solution and gentle swirling to mix. Whole cell patch clamp readings were carried out with an Axopatch 200A amplifier (Axon Instruments) as described previously. (Zamponi et al., 1997, *Nature* 385: 442-446). The external recording solution was 2 mM $CaCl_2$, 1 mM $MgCl_2$, 10 mM HEPES, 40 mM TEA-Cl, 10 mM glucose, 92 mM CsCl, pH=7.2 with TEA-hydroxide. The internal pipette solutions was 105 mM CsCl, 25 mM TEA-Cl, 1 mM $CaCl_2$, 11 mM EGTA, 10 mM HEPES, pH 7.2 with NaOH.

For determination of current-voltage (I-V) relationships, cells were held at a resting potential of −100 mV and then stepped to various depolarizing test potentials. For steady-state inactivation, cells were held at various potentials for 20 sec. and currents recorded during a subsequent test pulse to the peak potential of the I-V. Leak currents and capacitative transients were subtracted using a P/5 procedure.

FIGS. 1-4 show the results obtained for HEK cells transfected with and expressing the cDNA of sequences ID Nos. 23 and 27, which correspond to the subunits designated as $\alpha_{1G}$ and $\alpha_{1I}$. FIGS. 1A and B and 2A and B shows a comparison of the waveforms and current-voltage relationship for the two channel subunit types. In the presence of recording solution containing 2 mM $Ca^{2+}$, both the $\alpha_{1G}$ and $\alpha_{1I}$ channel subunits exhibit activation properties consistent with native T-type calcium currents. FIGS. 1A and 2A show the subunit calcium current from a cell held at −120 mV and depolarized to a series of test potentials. FIGS. 1B and 2B show the magnitude of the calcium current. From a holding potential of −110 mV, both channel first activate at approximately −70 mV and peak currents are obtained between −40 and −50 mV. Upon depolarization to various test potentials, the current waveforms of the $\alpha_{1G}$ and $\alpha_{1I}$ calcium channels exhibit an overlapping pattern characteristic of native T-type channels in nerve, muscle and endocrine cells.

Figure 3:
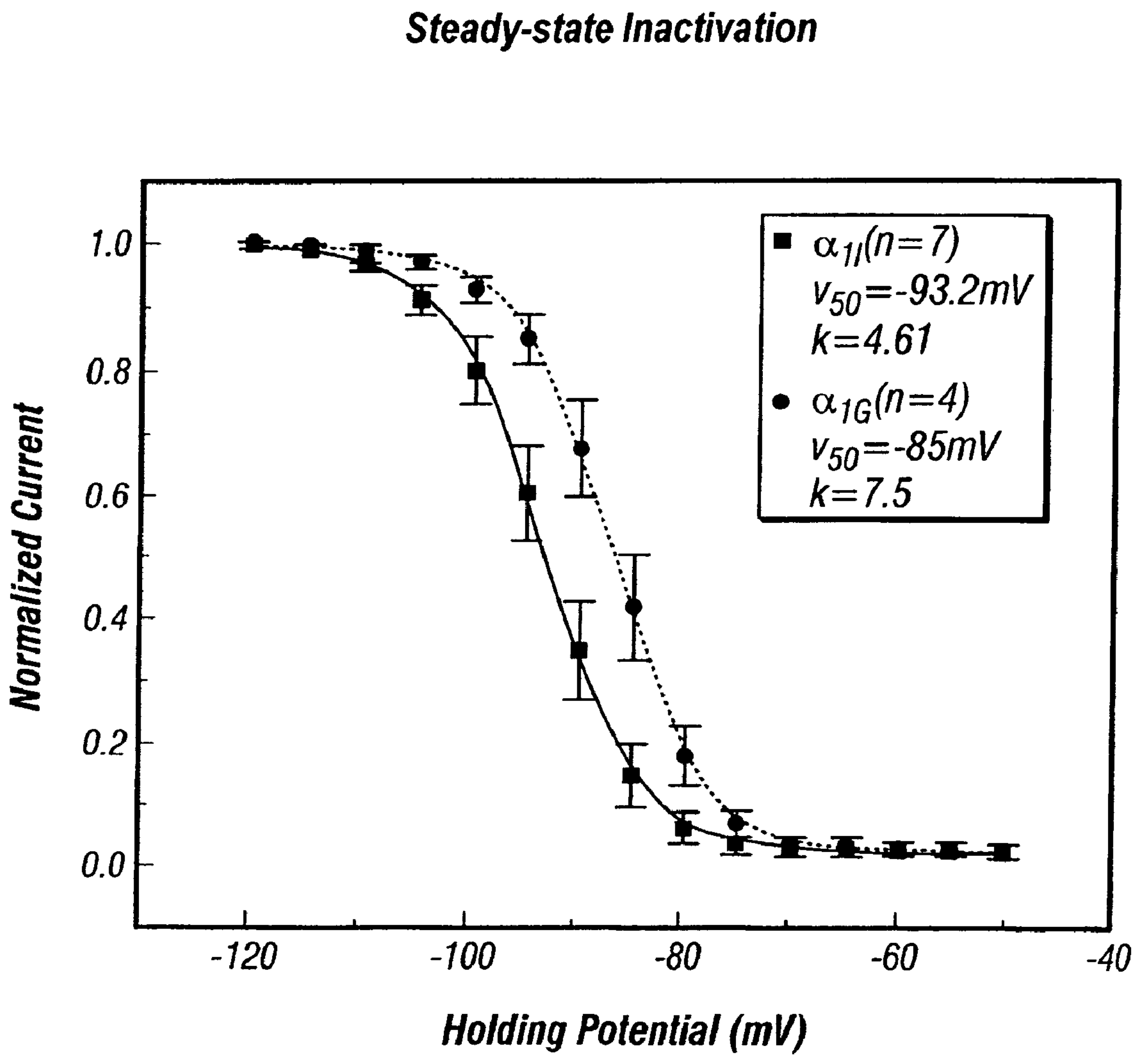
FIG. 3 shows a comparison of the steady state inactivation profiles of the $\alpha_{1G}$ and $\alpha_{1I}$ calcium channels.

FIG. 3 shows steady-state inactivation profiles for the $\alpha_{1G}$ and $\alpha_{1I}$ calcium channels in HEK 293 cells transiently transformed with full length cDNAs (SEQ ID NOS. 23 or 27) for $\alpha_{1G}$ or $\alpha_{1I}$ subunits. Steady state inactivation properties were determined by stepping from −120 mV to prepulse holding potentials between −120 mV and −50 mV for 15 sec. prior to a test potential of −30 mV. The data are plotted as normalized whole cell current versus prepulse holding potential and show that $\alpha_{1G}$ exhibits a $V_{50}$ of approximately −85 mV and $\alpha_{1I}$ a $V_{50}$ of approximately −93 mV. Thus, consistent with native T-type calcium channels, both of the $\alpha_{1G}$ and $\alpha_{1I}$ calcium channels exhibit pronounced steady-state inactivation at negative potentials.

Figures 4A, 4B, 4C:
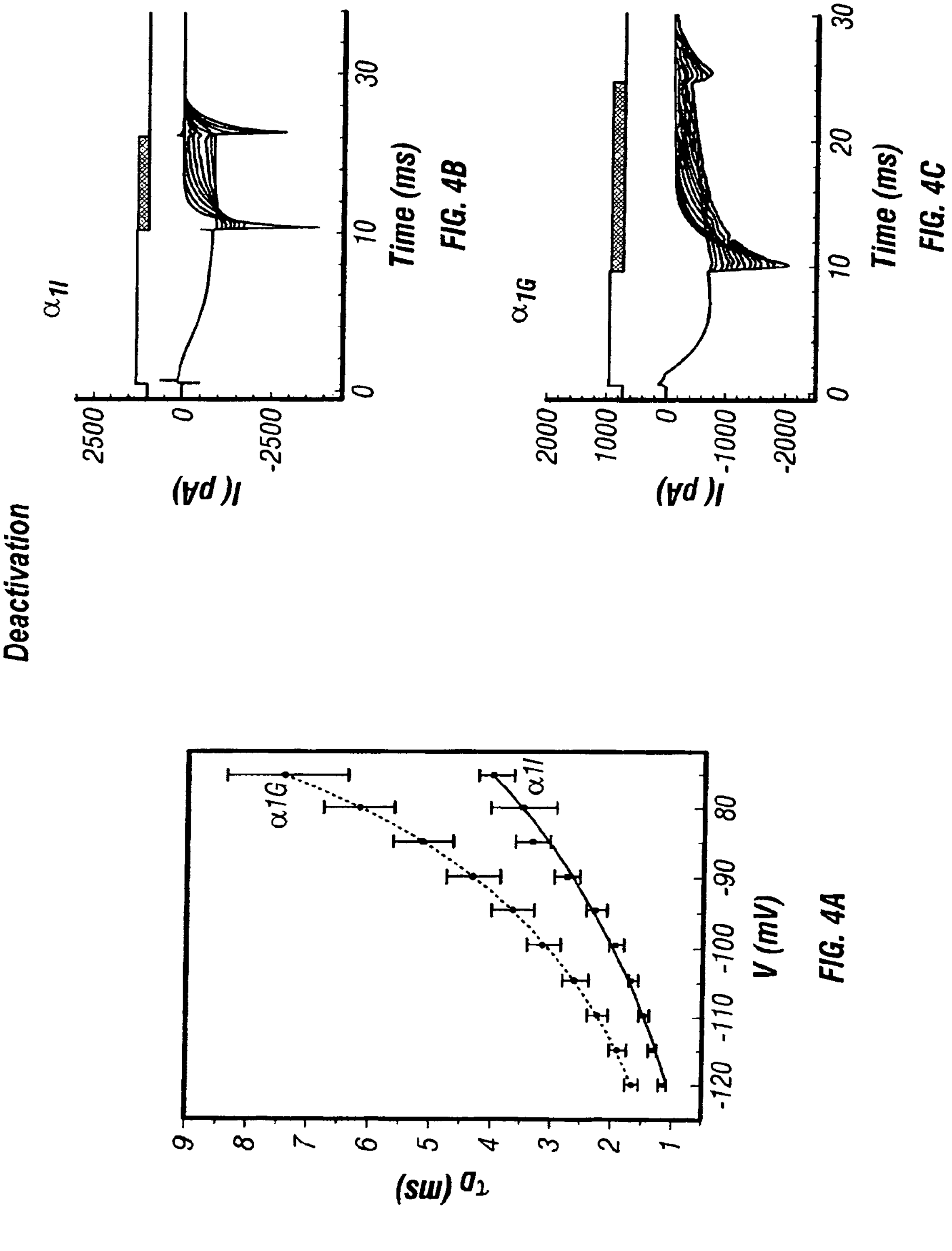
FIGS. 4A-C show a comparison of the inactivation kinetics of the $\alpha_{1G}$ and $\alpha_{1I}$ calcium channels.

FIGS. 4A-C show a comparison of the voltage-dependent deactivation profiles of the $\alpha_{1G}$ and $\alpha_{1I}$ calcium channels. HEK 293 cells were transiently transfected with either an $\alpha_{1G}$ or $\alpha_{1I}$ subunit cDNA (SEQ. ID NO: 23 or 27). The deactivation properties of $\alpha_{1G}$ were determined by stepping from a holding potential of −100 mV to −40 mV for 9 msec, and then to potentials between −120 mV and −45 mV. The deactivation properties of $\alpha_{1I}$ were determined by stepping from a holding potential of −100 mV to −40 mV for 20 msec, and then to potentials between −120 mV and −45 mV. Both channels exhibit slow deactivation kinetics compared to typical high-threshold channels, and is consistent with the $\alpha_{1G}$ and $\alpha_{1I}$ subunits being subunits for T-type calcium channels

EXAMPLE 3

Cloning of a Full Length cDNA for the Human α1G T-Type Calcium Channel Subunit Materials and Methods:

A full length cDNA encoding the human $\alpha_{1G}$ subunit was constructed from 5 overlapping clones (FIG. 1B) isolated from a human thalamus cDNA library constructed in λgt11 vector (Clontech, Cat#HL5009b).

Three λgt11 cDNA clones were isolated by conventional filter hybridization.

Clone 1 was identified by hybridization to a 567 bp cDNA probe (SEQ. ID. NO: 19) containing the transmembrane region S4 to S6 of domain I of the previously cloned human neuronal $\alpha_{1I}$ T-type calcium channel subunit. Clones HG10-1112 and HG5-1211 were identified by hybridization to a 1265 bp cDNA probe of the rat $\alpha_{1H}$ T-type calcium channel subunit spanning domain II and part of the II-III intracellular loop. cDNA probes were $^{32}$P-dCTP labeled by random priming using a Multiprime DNA labeling system (Amersham Pharmacia). Plaque lifts using H-bond nylon membranes were done in duplicate following the standard protocols supplied by manufacturer (Amersham Pharmacia). Hybridization was performed for at least 16 hrs at 65° C. for clone 1 and for at least 16 hrs at 58° C., clones HG10-1112 and HG5-1211. Membranes were washed in 0.1×SSC/0.3% SDS at 62° C. for clone 1 and 0.2×SSC/0.1% SDS at 58° C. clones HG10-1112 and HG5-1211. Blots were exposed to BioMax MS Kodak film with Kodak HE intensifying screens for at least 48 hrs at −80° C. Double positive plaques were isolated and re-screened to isolate single clones according to the procedure above. Bacteriophage DNA's were then isolated according to the λgt11 library User Manual (Clontech). Clone 1 cDNA insert was excised with EcoRI (NEB) and subcloned into pBluescriptKS (Stratagene). Clones HG10-1112 and HG5-1211 cDNA inserts were excised from λDNA with Not I (NEB) and subcloned into the Not I site of pBluescriptKS. Plasmids with cDNA inserts were transformed by electroporation into XL-I *E. coli* host strain bacteria and sequenced using universal reverse and forward primers according to Sanger double stranded DNA sequencing method in combination with automatic sequencing ABI 100 PRISM model 377 Version 3.3 (PE Biosystems).

Clone 1 was identified as a human $\alpha_{1G}$ subunit containing the 5'UTR and 1933 bp of the in-frame coding region, including part of the intracellular I-II loop. Clone HG10-1112 was identified as a human $\alpha_{1G}$ subunit of 3915 bp, spanning Domainl (S5-S6) to the III-IV loop. Clone HG5-1211 was identified as human $\alpha_{1G}$ subunit of 3984 bp containing the I-II linker and C-terminus.

For expression in HEK cells, removal of 5' UTR from clone 1 was achieved by replacing 5'UTR DNA fragment flanked by Hind III/SacII restriction sites with 5'end-291 bp cDNA fragment, containing translation start site and an incorporated Hind III site for subsequent cloning into pcDNA3.1 (Invitrogen). Following PCR conditions were used: 94° C.–30 sec, 45° C. –30 sec, 72° C.–30 sec for 5 cycles and followed by 94° C.–30 sec, 48° C.-30 sec, 72° C.-30 sec for 20 cycles (Bio-rad Gene Cycler). The cDNA fragment was subcloned into p-Gem-T-Easy plasmid vector (Promega) and the DNA sequence determined.

The remaining region of the 3' $\alpha_{1G}$ subunit cDNA was obtained using the PCR method on a human thalamus cDNA library with primers MD19-sense (5'GCG TGG AGC TCT TTG GAG 3') (SEQ ID NO:48) and G26-antisense (5' GCA CCC AGT GGA GAA AGG TG 3') (SEQ ID NO:49). The PCR protocol used was 94° C.–30 sec, 58° C.–30 sec, 72° C.–30 sec for 25 cycles (Bio-rad Gene Cycler). A cDNA fragment of 1617 bp was subcloned into p-Gem-T-Easy plasmid vector (Promega) and sequenced. The 3'PCR cDNA was identified as a human $\alpha_{1G}$ subunit spanning from Domain IV-S5 to the carboxyl terminus including the stop codon.

Figure 5A:
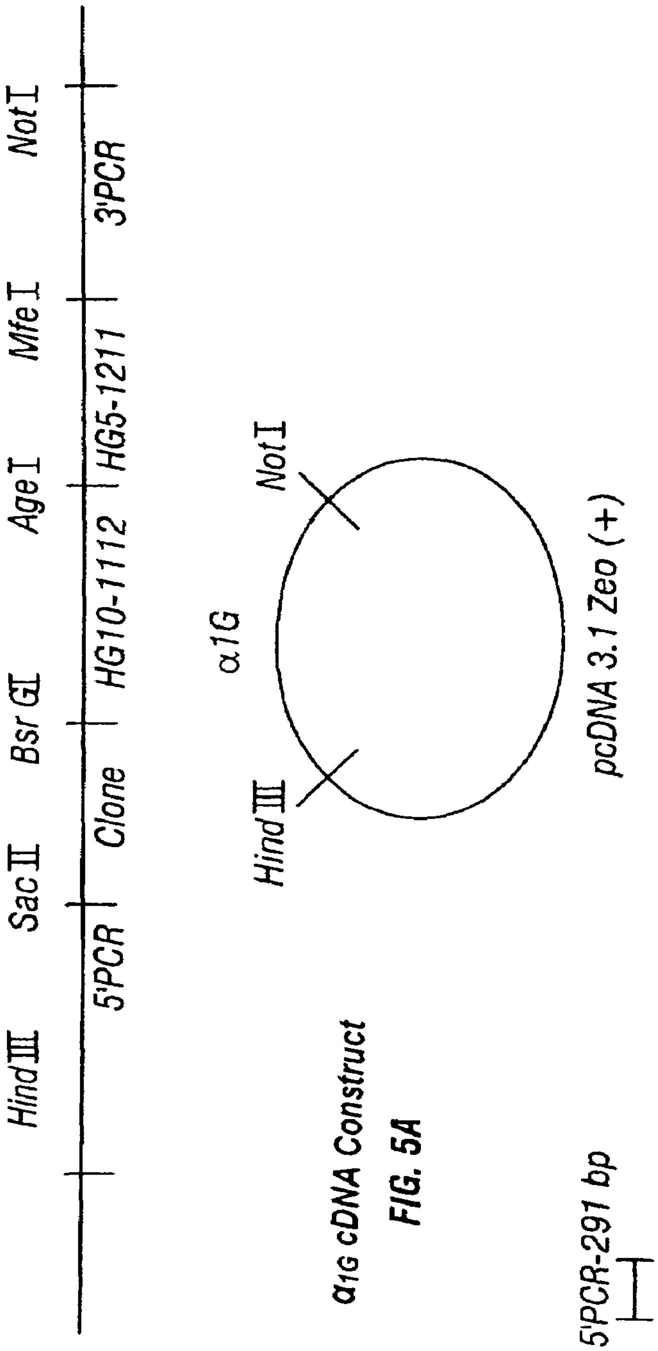
FIGS. 5A and 5B show the construction of the human $\alpha_{1G}$ cDNA complete sequence from partial clones.
Figure 5B:
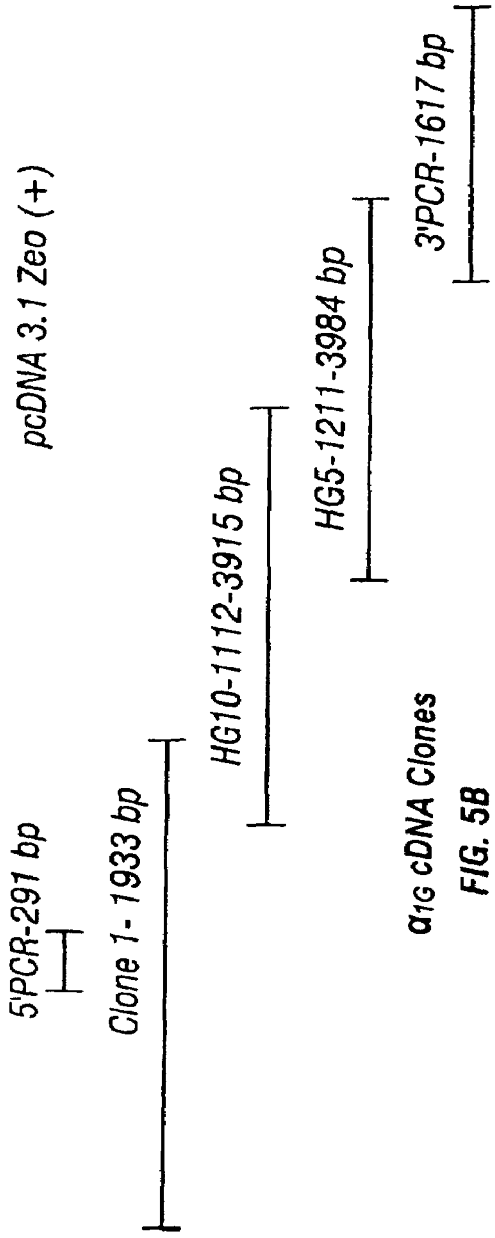

Unique restriction sites (FIGS. 5A and B) of the partial cDNA clones were used to construct the full length human $\alpha_{1G}$ T-type calcium channel in pcDNA3.1 Zeo (+) (Invitrogen) mammalian expression vector.

The complete nucleotide and amino acid sequences are shown in FIG. 6A-6L.

In order to determine the functional properties of the human $\alpha_{1G}$ channel standard calcium-phosphate transfection was used to transiently express the channel in HEK ts201 cells. Cells were cultured in Dulbecco's modified eagle medium (DMEM) supplemented with 10% fetal bovine serum, 200 U/ml penicillin and 0.2 mg/ml streptomycin at 37° C. with 5% $CO_2$. Ατ 85% χονφλυενχψ χελλσ ωερε σπλιτ ωιτη 0.25% τρψπσιν/1 μM ΕΔΤΑ ανδ πλατε δ ατ 10% χονφλυενχψ ον γλασσ χοωερσλιπσ. Ατ 12 ηουρσ τηε μεδιυμ ωασ ρεπλαχεδ ανδ τηε χελλσ τρανσιεντλψ τρανσφεχτε δ υσινγ α στανδαρδ χαλχιυμ πηοσπηατε προτοχολ ανδ τηε $\alpha_{1G}$ calcium channel cDNA. Fresh DMEM was supplied and the cells transferred to 28° C./5% $CO_2$. Cells were incubated for 1 to 2 days prior to whole cell recording. Whole cell patch recordings were performed using an Axopatch 200B amplifier (Axon Instruments) linked to an IBM compatible personal computer equipped with pCLAMP version 7.0 software. The intrapipette solution contained (in mM): 105 CsCl, 25 CsCl, 1 $CaCl_2$, 11 EGTA, 10 HEPES, pH 7.2. The extracellular solution contained (in mM): 40 TEA-Cl, 2 $CaCl_2$, 1 $MgCl_2$, 92 CsCl, 10 glucose, 10 HEPES, pH 7.2.

Figure 7:
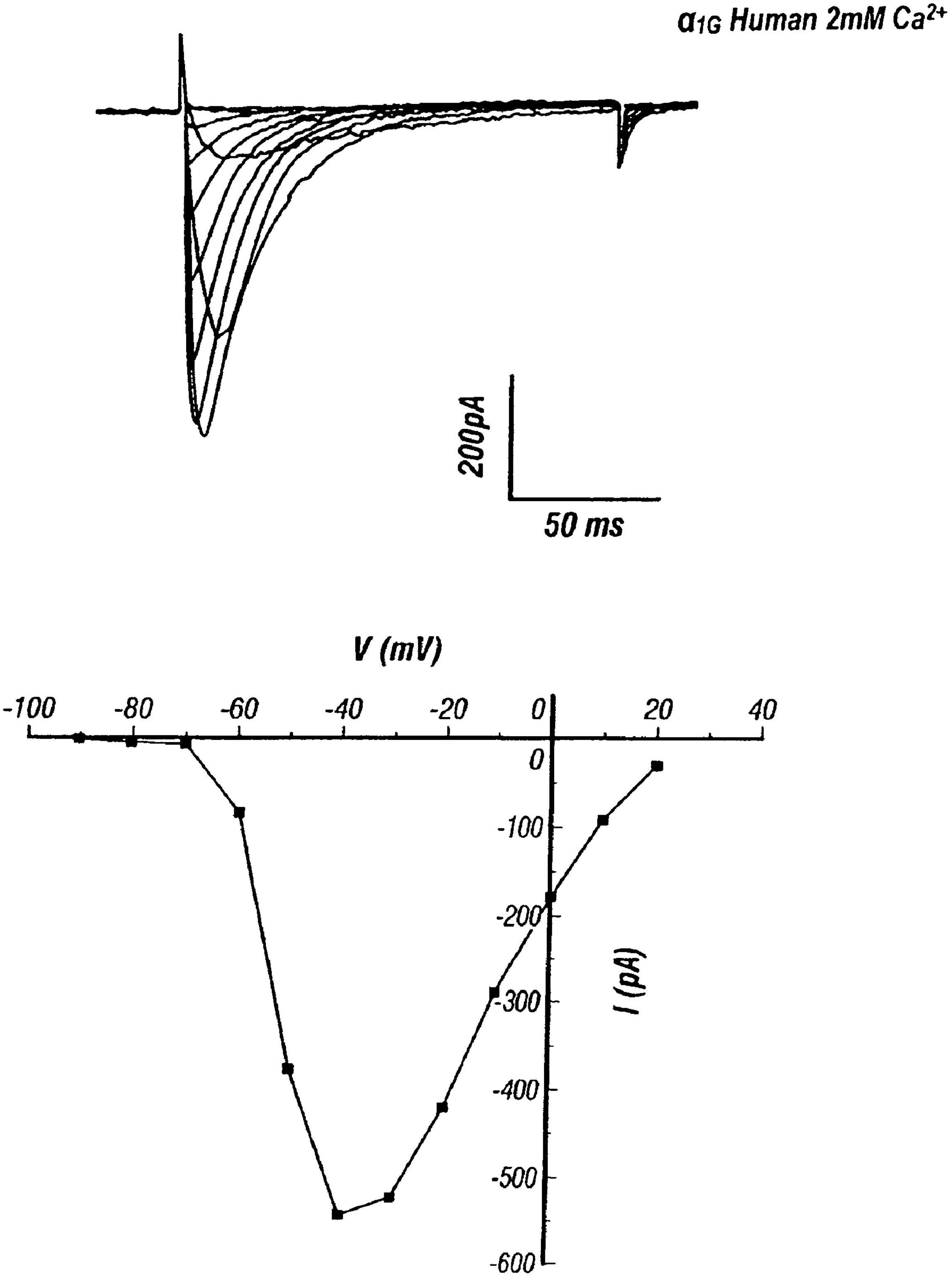
FIG. 7 shows a comparison of the waveforms and current voltage relationship for human $\alpha_{1G}$ calcium channel.

FIG. 7 shows that the human $\alpha_{1G}$ cDNA encodes a calcium channel with typical properties of a T-type current. The left panel illustrates representative current traces obtained from a holding potential of −100 mV to test pulses potentials of −90 mV to +20 mV. The traces show a typical crossover pattern and considerable inactivation during the test pulse, both of which are consistent with native T-type channels. The right panel shows a plot of the peak whole current at various test potentials and indicates that the human α1G cDNA first activates near −60 mV with maximal current near −40 mV, which is also consistent with native low-threshold T-type calcium channels.

The invention claimed is:

1. An isolated recombinant DNA molecule which comprises an expression cassette wherein said expression cassette comprises a nucleotide sequence encoding a T-type calcium channel $\alpha_{1H}$ subunit, said encoding sequence operably linked to control sequences to effect its expression; wherein said $\alpha_{1H}$ subunit has the amino acid sequence of SEQ ID NO: 26.

2. Recombinant host cells modified to contain the DNA molecule of claim 1.

3. The cells of claim 2 which are mammalian cells.

4. A method to effect production of a recombinant functional calcium channel which method comprises culturing the cells of claim 2 under conditions wherein said functional calcium channels are produced.

5. A method to effect production of a recombinant functional calcium channel which method comprises culturing the cells of claim 3 under conditions wherein said functional calcium channels are produced.

6. An isolated nucleic acid molecule which comprises a nucleotide sequence encoding a T-type calcium channel $\alpha_{1H}$ subunit or its full-length complement, wherein said $\alpha_{1H}$ subunit has the amino acid sequence of SEQ ID NO: 26.

7. Recombinant host cells modified to contain the DNA molecule of claim 6.

8. The cells of claim 7 which are mammalian cells.

9. A method to effect production of a recombinant functional calcium channel which method comprises culturing the cells of claim 7 under conditions wherein said functional calcium channels are produced.

10. A method to effect production of a recombinant functional calcium channel which method comprises culturing the cells of claim 8 under conditions wherein said functional calcium channels are produced.

* * * * *

SEQUENCE LISTING

<160> NUMBER OF SEQ ID NOS: 49

<210> SEQ ID NO 1
<211> LENGTH: 24
<212> TYPE: DNA
<213> ORGANISM: Artificial Sequence
<220> FEATURE:
<223> OTHER INFORMATION: oligonucleotide probe for locating calcium channel

<400> SEQUENCE: 1
gtcaaaactc aggccttcta ctgg 24

<210> SEQ ID NO 2
<211> LENGTH: 24
<212> TYPE: DNA
<213> ORGANISM: Artificial Sequence
<220> FEATURE:
<223> OTHER INFORMATION: oligonucleotide probe for locating calcium channel

<400> SEQUENCE: 2
aacgtgttct tggctatcgc ggtg 24

<210> SEQ ID NO 3
<211> LENGTH: 24

-continued

<212> TYPE: DNA
<213> ORGANISM: Artificial Sequence
<220> FEATURE:
<223> OTHER INFORMATION: oligonucleotide probe for locating calcium
channel

<400> SEQUENCE: 3
gtgaaagcac agagcttcta ctgg 24

<210> SEQ ID NO 4
<211> LENGTH: 24
<212> TYPE: DNA
<213> ORGANISM: Artificial Sequence
<220> FEATURE:
<223> OTHER INFORMATION: oligonucleotide probe for locating calcium
channel

<400> SEQUENCE: 4
aacgttttct tggccattgc tgtg 24

<210> SEQ ID NO 5
<211> LENGTH: 24
<212> TYPE: DNA
<213> ORGANISM: Artificial Sequence
<220> FEATURE:
<223> OTHER INFORMATION: oligonucleotide probe for locating calcium
channel

<400> SEQUENCE: 5
gttaaatcca acgtcttcta ctgg 24

<210> SEQ ID NO 6
<211> LENGTH: 24
<212> TYPE: DNA
<213> ORGANISM: Artificial Sequence
<220> FEATURE:
<223> OTHER INFORMATION: oligonucleotide probe for locating calcium
channel

<400> SEQUENCE: 6
aatgtgttct tggccattgc ggtg 24

<210> SEQ ID NO 7
<211> LENGTH: 24
<212> TYPE: DNA
<213> ORGANISM: Artificial Sequence
<220> FEATURE:
<223> OTHER INFORMATION: oligonucleotide probe for locating calcium
channel

<400> SEQUENCE: 7
gtgaagtctg tcacgtttta ctgg 24

<210> SEQ ID NO 8
<211> LENGTH: 24
<212> TYPE: DNA
<213> ORGANISM: Artificial Sequence
<220> FEATURE:
<223> OTHER INFORMATION: oligonucleotide probe for locating calcium
channel

<400> SEQUENCE: 8
aagctcttct tggccattgc tgta 24

<210> SEQ ID NO 9
<211> LENGTH: 24
<212> TYPE: DNA

-continued

```
<213> ORGANISM: Artificial Sequence
<220> FEATURE:
<223> OTHER INFORMATION: oligonucleotide probe for locating calcium
      channel

<400> SEQUENCE: 9

gtcaagtcgc aagtgttcta ctgg                                        24


<210> SEQ ID NO 10
<211> LENGTH: 24
<212> TYPE: DNA
<213> ORGANISM: Artificial Sequence
<220> FEATURE:
<223> OTHER INFORMATION: oligonucleotide probe for locating calcium
      channel

<400> SEQUENCE: 10

aatgtattct tggctatcgc tgtg                                        24


<210> SEQ ID NO 11
<211> LENGTH: 21
<212> TYPE: DNA
<213> ORGANISM: Artificial Sequence
<220> FEATURE:
<223> OTHER INFORMATION: oligonucleotide probe for locating calcium
      channel

<400> SEQUENCE: 11

atctaygcyr tsatyggsat g                                           21


<210> SEQ ID NO 12
<211> LENGTH: 20
<212> TYPE: DNA
<213> ORGANISM: Artificial Sequence
<220> FEATURE:
<223> OTHER INFORMATION: oligonucleotide probe for locating calcium
      channel

<400> SEQUENCE: 12

atggacaayt tygastaytc                                             20


<210> SEQ ID NO 13
<211> LENGTH: 168
<212> TYPE: DNA
<213> ORGANISM: Homo sapiens

<400> SEQUENCE: 13

gtgatcactc tggaaggctg ggtggagatc atgtactacg tgatggatgc tcactccttc     60

tacaacttca tctacttcat cctgcttatc atacccctct tgccttgcac cccatatggt    120

cttcccagag tgagctcatc cacctcgtca tgcctgactc gacgttca                 168


<210> SEQ ID NO 14
<211> LENGTH: 98
<212> TYPE: DNA
<213> ORGANISM: Homo sapiens

<400> SEQUENCE: 14

gatggtcgag tactccctgg accttcagaa catcaacctg tcagccatcc gcaccgtgcg     60

cgtcctgagg cccctcaaag ccatcaaccg cgtgccca                             98


<210> SEQ ID NO 15
<211> LENGTH: 94
<212> TYPE: DNA
<213> ORGANISM: Homo sapiens
```

-continued

<400> SEQUENCE: 15
catgctggtg atcctgctga actgcgtgac acttggcatg taccagccgt gcgacgacat 60
ggactgcctg tccgaccgct gcaagatcct gcag 94

<210> SEQ ID NO 16
<211> LENGTH: 123
<212> TYPE: DNA
<213> ORGANISM: Homo sapiens

<400> SEQUENCE: 16
gtatctctgg ttactttagt agccaacact cttggctact cagaccttgg tcccattaaa 60
tccctgcgaa ccttgagagc actaagacct ctaagagctt tgtctagatt tgaaggaatg 120
agg 123

<210> SEQ ID NO 17
<211> LENGTH: 5562
<212> TYPE: DNA
<213> ORGANISM: Homo sapiens

<400> SEQUENCE: 17
atgtttttcg tctcagccaa tccctgggtg agtttcacca gttttgattt aaacgtggcc 60
aatatggaca acttcttcgc ccccgttttc accatgggca aatattatac gcaaggcgac 120
aaggtgctga tgccgctggc gattcaggct ctgaaacagc tgatgttcaa attggtggcc 180
actgttgctc gaacacatgc tacaccgtca cacatcacgg gtggtcctgg aacagggatg 240
cacacgggca ccttccagga aggagctgag cctggttcat ctcagcaccc tgaggcacag 300
gccacgtata cagcagggtg caccccagcc cccacgggcg atcccacctg ctgctttgtc 360
cttgacttgg tgtgcacgtg gtttgaatgt gtcagcatgc tggtgatcct gctgaactgc 420
gtgacacttg gcatgtacca gccgtgcgac gacatggact gcctgtccga ccgctgcaag 480
atcctgcagg tctttgatga cttcatcttt atcttctttg ccatggagat ggtgctcaag 540
atggtggccc tggggatttt tggcaagaag tgctacctcg gggacacatg gaaccgcctg 600
gatttcttca tcgtcatggc aggcaacatc aacctgtcag ccatccgcac cgtgcgcgtc 660
ctgaggcccc tcaaagccat caaccgcgtg cccagtatgc ggatcctggt gaacctgctc 720
ctggacacac tgcccatgct ggggaatgtc ctgctgctct gcttctttgt cttcttcatc 780
tttggcatca taggtgtgca gctctgggcg ggcctgctgc gtaaccgctg cttcctggag 840
gagaacttca ccatacaagg ggatgtggcc ttgcccccat actaccagcc ggaggaggat 900
gatgagatgc ccttcatctg ctccctgtcg ggcgacaatg ggataatggg ctgccatgag 960
atccccccgc tcaaggagca gggccgtgag tgctgcctgt ccaaggacga cgtctacgac 1020
tttggggcgg ggcgccagga cctcaatgcc agcggcctct gtgtcaactg gaaccgttac 1080
tacaatgtgt gccgcacggg cagcgccaac ccccacaagg gtgccatcaa ctttgacaac 1140
atcggttatg cttggattgt catcttccag gtgatcactc tggaaggctg ggtggagatc 1200
atgtactacg tgatggatgc tcactccttc tacaacttca tctacttcat cctgcttatc 1260
ataagtgagc tcatccacct cgtcatgcct gactgcagct tcagcacagc acagtcccca 1320
aaatgtcaag gtgattcact cccaggagtc gctgctgaat ccctgctgct gcgagactct 1380
agctcctcag tcatcactga tgaggctgca gccatggaga acctcctggc gggcacctcc 1440
aagggggatg aaagctatct gctcaggctg gccggcagcc aagttcactc ccaggctcag 1500

-continued

```
caaatgctgg ggagggggct gggccctgaa agcctggaaa ctggagagga gccccactcg   1560
tggagccctc gggccacaag gagatgggat ccccaatgcc aaccagggca gcctctcccc   1620
cttcatttca tgcaagcaca ggtgggctcc ttcttcatga tcaacctgtg cctcgttgtc   1680
atagcgaccc agttctcgga gaccaagcaa cgggagcacc ggctgatgct ggagcagcgg   1740
cagcgctacc tgtcctccag cacggtggcc agctacgccg agcctggcga ctgctacgag   1800
gagatcttcc agtatgtctg ccacatcctg cgcaaggcca agcgccgcgc cctgggcctc   1860
taccaggccc tgcagagccg gcgccaggcc ctgggcccgg aggccccggc ccccgccaaa   1920
cctgggcccc acgccaagga gccccggcac taccctctca cagtctggga atcgattctt   1980
gggaggcaag cagaagaatg cacgctcaga gctgccgccc acccgtcctc gggtgccagc   2040
catccaggcg tgggctcgga ggaggcccca gagctgtgcc cgcaacatag cccccctggat  2100
gcgacgcccc acaccctggt gcagcccatc cccgccacgc tggcttccga tcccgccagc   2160
tgcccttgct gccagcatga ggacggccgg cggccctcgg gcctgggcag caccgactcg   2220
ggccaggagg gctcgggctc cgggagctcc gctggtggcg aggacgaggc ggatggggac   2280
ggggcccgga gcagcgagga cggagcctcc tcagaactgg ggaaggagga ggaggaggag   2340
gagcaggcgg atggggcggt ctggctgtgc ggggatgtgt ggcgggagac gcgagccaag   2400
ctgcgcggca tcgtggacag caagtacttc aaccggggca tcatgatggc catcctggtc   2460
aacaccgtca gcatgggcat cgagcaccac gagcaggcca gtgcagcgca gccgggccgg   2520
gcctgcggga gaggacaaaa tccagacctt tgcatgaccc tcaaggcccc ttgtctctgt   2580
cacaacgtcc cttcaccagg ccagggtgtc ctgtcccatc cagtgactcc accccataca   2640
gccccatggc gcatggagac aggaaagcag ggacacggat gtgaagaagg accaggacaa   2700
cgaagcagtg acatgtttgc cctggagatg atcctgaagc tggctgcatt tgggctcttc   2760
gactacctgc gtaaccccta caacatcttc gacagcatca ttgtcatcat cagcatctgg   2820
gagatcgtgg ggcaggcgga cggtgggctg tcggtgctgc ggaccttccg gctgctgcgc   2880
gtgctgaaac tggtgcgctt catgcctgcc ctgcggcgcc agctcgtggt gctcatgaag   2940
accatggaca acgtggccac cttctgcatg ctgctcatgc tcttcatctt catcttcagc   3000
atccttggga tgcatatttt tggctgcaag ttcagcctcc gcacggacac tggagacacg   3060
gtgcccgaca ggaagaactt cgactccctg ctgtgggcca tcgtcactgt gttccagatc   3120
ctcacccagg aggactggaa cgtcgttctc tacaatggca tggcctccac ttctccctgg   3180
gcctccctct actttgtcgc cctcatgacc ttcggcaact atgtgctctt caacctgctg   3240
gtggccatcc tggtggaggg cttccaggcg gaggtgactg tggtcttggc agaggaagca   3300
cccccacagg gcctgcgaaa gactgggcga gggagaggtg gcctggatgg gggagggctg   3360
caattcaaac ttctagcagg caacctatcc ctaaaggagg gggttgctga tgaggtgggt   3420
gacgccaatc gctcctactc ggacgaggac cagagctcat ccaacataga agagtttgat   3480
aagctccagg aaggcctgga cagcagcgga gatcccaagc tctgcccaat ccccatgacc   3540
cccaatgggc acctggaccc cagtctccca ctgggtgggc acctaggtcc tgctggggct   3600
gcgggacctg ccccccgact ctcactgcag ccggaccccca tgctggtggc cctgggctcc  3660
cgaaagagca gcgtcatgtc tctagggagg atgagctatg accagcgctc cctggtgggt   3720
ggtcttagag ccacagcggg ggtgcaggct gcctttgggc acctggtgcc ccagccgtgg   3780
gtgtgcctgt ggggcgctga cccgaacggg aactccttcc agtccagctc ccggagctcc   3840
tactacgggc catggggccg cagcgcggcc tgggccagcc gtcgctccag ctggaacagc   3900
```

-continued ctcaagcaca agccgccgtc ggcggagcat gagtccctgc tctctgcgga gcgcggcggc 3960
ggcgcccggg tctgcgaggt tgccgcggac gaggggccgc cgcgggccgc acccctgcac 4020
accccacacg cccaccacgt tcatcacggg ccccatctgg cgcaccgcca ccgccaccac 4080
cgccggacgc tgtccctcga caacagggac tcggtggacc tggccgagct ggtgcccgcg 4140
gtgggcgccc acccccgggc cgcctggagg gcggcaggcc cggcccccgg gcatgaggac 4200
tgcaatggca ggatgcccag catcgccaaa gacgtcttca ccaagatggg cgaccgcggg 4260
gatcgcgggg aggatgagga ggaaatcgac tacgtgagtg ggggcggggc cgaaggggac 4320
ctgaccctgt gcttccgcgt ccgcaagatg atcgacgtct ataagcccga ctggtgcgag 4380
gtccgcgaag actggtctgt ctacctcttc tctcccgaga acaggctcag ggatctgggc 4440
tgggtaagcc tcgagtgcca gggaaaggtg ggtgacctcg tggtgtgggt gtatggtcag 4500
aggaggcagc gccagaccat tattgcccac aaactcttcg actacgtcgt cctggccttc 4560
atctttctca actgcatcac catcgccctg gagcggcctc agatcgaggc cggcagcacc 4620
gaacgcatct ttctcaccgt gtccaactac atcttcacgg ccatcttcgt gggcgagatg 4680
acattgaagg tagtctcgct gggcctgtac ttcggcgagc aggcgtacct acgcagcagc 4740
tggaacgtgc tggatggctt tcttgtcttc gtgtccatca tcgacatcgt ggtgtccctg 4800
gcctcagccg gggagccaa gatcttgggg gtcctccgag tcttgcggct cctgcgcacc 4860
ctacgccccc tgcgtgtcat cagccgggcg ccgggcctga agctggtggt ggagacactc 4920
atctcctccc tcaagcccat cggcaacatc gtgctcatct gctgtgcctt cttcatcatc 4980
tttggcatcc tgggagtgca gctcttcaag ggcaagttct accactgtct gggcgtggac 5040
acccgcaaca tcaccaaccg ctcggactgc atggccgcca actaccgctg ggtccatcac 5100
aaatacaact tcgacaacct gggccaggct ctgatgtccc tctttgtcct ggcatccaag 5160
gatggttggg tgaacatcat gtacaatgga ctggatgctg ttgctgtgga ccagcagcct 5220
gtgaccaacc acaaccctg gatgctgctg tacttcatct ccttcctgct catcgtcagc 5280
ttctttgtgc tcaacatgtt tgtgggtgtc gtggtggaga acttccacaa gtgccggcag 5340
caccaggagg ctgaagaggc acggcggcgt gaggagaagc ggctgcggcg cctggagaag 5400
aagcgccgga aggcccagcg gctgccctac tatgccacct attgtcacac ccggctgctc 5460
atccactcca tgtgcaccag ccactacctg gacatcttca tcaccttcat catctgcctc 5520
aacgtggtca ccatgtccct ggagcactac aatcagccca cg 5562

<210> SEQ ID NO 18
<211> LENGTH: 1854
<212> TYPE: PRT
<213> ORGANISM: Homo sapiens

<400> SEQUENCE: 18

Met Phe Phe Val Ser Ala Asn Pro Trp Val Ser Phe Thr Ser Phe Asp
1 5 10 15

Leu Asn Val Ala Asn Met Asp Asn Phe Phe Ala Pro Val Phe Thr Met
20 25 30

Gly Lys Tyr Tyr Thr Gln Gly Asp Lys Val Leu Met Pro Leu Ala Ile
35 40 45

Gln Ala Leu Lys Gln Leu Met Phe Lys Leu Val Ala Thr Val Ala Arg
50 55 60

Thr His Ala Thr Pro Ser His Ile Thr Gly Gly Pro Gly Thr Gly Met
65 70 75 80

-continued

```
His Thr Gly Thr Phe Gln Glu Gly Ala Glu Pro Gly Ser Ser Gln His
                85                  90                  95

Pro Glu Ala Gln Ala Thr Tyr Thr Ala Gly Cys Thr Pro Ala Pro Thr
            100                 105                 110

Gly Asp Pro Thr Cys Cys Phe Val Leu Asp Leu Val Cys Thr Trp Phe
        115                 120                 125

Glu Cys Val Ser Met Leu Val Ile Leu Leu Asn Cys Val Thr Leu Gly
    130                 135                 140

Met Tyr Gln Pro Cys Asp Asp Met Asp Cys Leu Ser Asp Arg Cys Lys
145                 150                 155                 160

Ile Leu Gln Val Phe Asp Asp Phe Ile Phe Ile Phe Phe Ala Met Glu
                165                 170                 175

Met Val Leu Lys Met Val Ala Leu Gly Ile Phe Gly Lys Lys Cys Tyr
            180                 185                 190

Leu Gly Asp Thr Trp Asn Arg Leu Asp Phe Phe Ile Val Met Ala Gly
        195                 200                 205

Asn Ile Asn Leu Ser Ala Ile Arg Thr Val Arg Val Leu Arg Pro Leu
    210                 215                 220

Lys Ala Ile Asn Arg Val Pro Ser Met Arg Ile Leu Val Asn Leu Leu
225                 230                 235                 240

Leu Asp Thr Leu Pro Met Leu Gly Asn Val Leu Leu Leu Cys Phe Phe
                245                 250                 255

Val Phe Phe Ile Phe Gly Ile Ile Gly Val Gln Leu Trp Ala Gly Leu
            260                 265                 270

Leu Arg Asn Arg Cys Phe Leu Glu Glu Asn Phe Thr Ile Gln Gly Asp
        275                 280                 285

Val Ala Leu Pro Pro Tyr Tyr Gln Pro Glu Glu Asp Asp Glu Met Pro
    290                 295                 300

Phe Ile Cys Ser Leu Ser Gly Asp Asn Gly Ile Met Gly Cys His Glu
305                 310                 315                 320

Ile Pro Pro Leu Lys Glu Gln Gly Arg Glu Cys Cys Leu Ser Lys Asp
                325                 330                 335

Asp Val Tyr Asp Phe Gly Ala Gly Arg Gln Asp Leu Asn Ala Ser Gly
            340                 345                 350

Leu Cys Val Asn Trp Asn Arg Tyr Tyr Asn Val Cys Arg Thr Gly Ser
        355                 360                 365

Ala Asn Pro His Lys Gly Ala Ile Asn Phe Asp Asn Ile Gly Tyr Ala
    370                 375                 380

Trp Ile Val Ile Phe Gln Val Ile Thr Leu Glu Gly Trp Val Glu Ile
385                 390                 395                 400

Met Tyr Tyr Val Met Asp Ala His Ser Phe Tyr Asn Phe Ile Tyr Phe
                405                 410                 415

Ile Leu Leu Ile Ile Ser Glu Leu Ile His Leu Val Met Pro Asp Cys
            420                 425                 430

Ser Phe Ser Thr Ala Gln Ser Pro Lys Cys Gln Gly Asp Ser Leu Pro
        435                 440                 445

Gly Val Ala Ala Glu Ser Leu Leu Leu Arg Asp Ser Ser Ser Ser Val
    450                 455                 460

Ile Thr Asp Glu Ala Ala Ala Met Glu Asn Leu Leu Ala Gly Thr Ser
465                 470                 475                 480

Lys Gly Asp Glu Ser Tyr Leu Leu Arg Leu Ala Gly Ser Gln Val His
                485                 490                 495
```

-continued

```
Ser Gln Ala Gln Gln Met Leu Gly Arg Gly Leu Gly Pro Glu Ser Leu
            500                 505                 510

Glu Thr Gly Glu Glu Pro His Ser Trp Ser Pro Arg Ala Thr Arg Arg
        515                 520                 525

Trp Asp Pro Gln Cys Gln Pro Gly Gln Pro Leu Pro Leu His Phe Met
    530                 535                 540

Gln Ala Gln Val Gly Ser Phe Phe Met Ile Asn Leu Cys Leu Val Val
545                 550                 555                 560

Ile Ala Thr Gln Phe Ser Glu Thr Lys Gln Arg Glu His Arg Leu Met
                565                 570                 575

Leu Glu Gln Arg Gln Arg Tyr Leu Ser Ser Ser Thr Val Ala Ser Tyr
            580                 585                 590

Ala Glu Pro Gly Asp Cys Tyr Glu Glu Ile Phe Gln Tyr Val Cys His
        595                 600                 605

Ile Leu Arg Lys Ala Lys Arg Arg Ala Leu Gly Leu Tyr Gln Ala Leu
    610                 615                 620

Gln Ser Arg Arg Gln Ala Leu Gly Pro Glu Ala Pro Ala Pro Ala Lys
625                 630                 635                 640

Pro Gly Pro His Ala Lys Glu Pro Arg His Tyr Pro Leu Thr Val Trp
                645                 650                 655

Glu Ser Ile Leu Gly Arg Gln Ala Glu Glu Cys Thr Leu Arg Ala Ala
            660                 665                 670

Ala His Pro Ser Ser Gly Ala Ser His Pro Gly Val Gly Ser Glu Glu
        675                 680                 685

Ala Pro Glu Leu Cys Pro Gln His Ser Pro Leu Asp Ala Thr Pro His
    690                 695                 700

Thr Leu Val Gln Pro Ile Pro Ala Thr Leu Ala Ser Asp Pro Ala Ser
705                 710                 715                 720

Cys Pro Cys Cys Gln His Glu Asp Gly Arg Arg Pro Ser Gly Leu Gly
                725                 730                 735

Ser Thr Asp Ser Gly Gln Glu Gly Ser Gly Ser Gly Ser Ser Ala Gly
            740                 745                 750

Gly Glu Asp Glu Ala Asp Gly Asp Gly Ala Arg Ser Ser Glu Asp Gly
        755                 760                 765

Ala Ser Ser Glu Leu Gly Lys Glu Glu Glu Glu Glu Glu Gln Ala Asp
    770                 775                 780

Gly Ala Val Trp Leu Cys Gly Asp Val Trp Arg Glu Thr Arg Ala Lys
785                 790                 795                 800

Leu Arg Gly Ile Val Asp Ser Lys Tyr Phe Asn Arg Gly Ile Met Met
                805                 810                 815

Ala Ile Leu Val Asn Thr Val Ser Met Gly Ile Glu His His Glu Gln
            820                 825                 830

Ala Ser Ala Ala Gln Pro Gly Arg Ala Cys Gly Arg Gly Gln Asn Pro
        835                 840                 845

Asp Leu Cys Met Thr Leu Lys Ala Pro Cys Leu Cys His Asn Val Pro
    850                 855                 860

Ser Pro Gly Gln Gly Val Leu Ser His Pro Val Thr Pro Pro His Thr
865                 870                 875                 880

Ala Pro Trp Arg Met Glu Thr Gly Lys Gln Gly His Gly Cys Glu Glu
                885                 890                 895

Gly Pro Gly Gln Arg Ser Ser Asp Met Phe Ala Leu Glu Met Ile Leu
            900                 905                 910

Lys Leu Ala Ala Phe Gly Leu Phe Asp Tyr Leu Arg Asn Pro Tyr Asn
```

-continued

```
        915                 920                 925

Ile Phe Asp Ser Ile Ile Val Ile Ile Ser Ile Trp Glu Ile Val Gly
    930                 935                 940

Gln Ala Asp Gly Gly Leu Ser Val Leu Arg Thr Phe Arg Leu Leu Arg
945                 950                 955                 960

Val Leu Lys Leu Val Arg Phe Met Pro Ala Leu Arg Arg Gln Leu Val
                965                 970                 975

Val Leu Met Lys Thr Met Asp Asn Val Ala Thr Phe Cys Met Leu Leu
            980                 985                 990

Met Leu Phe Ile Phe Ile Phe Ser Ile Leu Gly Met His Ile Phe Gly
        995                 1000                1005

Cys Lys Phe Ser Leu Arg Thr Asp Thr Gly Asp Thr Val Pro Asp Arg
    1010                1015                1020

Lys Asn Phe Asp Ser Leu Leu Trp Ala Ile Val Thr Val Phe Gln Ile
1025                1030                1035                1040

Leu Thr Gln Glu Asp Trp Asn Val Val Leu Tyr Asn Gly Met Ala Ser
                1045                1050                1055

Thr Ser Pro Trp Ala Ser Leu Tyr Phe Val Ala Leu Met Thr Phe Gly
            1060                1065                1070

Asn Tyr Val Leu Phe Asn Leu Leu Val Ala Ile Leu Val Glu Gly Phe
        1075                1080                1085

Gln Ala Glu Val Thr Val Val Leu Ala Glu Glu Ala Pro Pro Gln Gly
    1090                1095                1100

Leu Arg Lys Thr Gly Arg Gly Arg Gly Gly Leu Asp Gly Gly Gly Leu
1105                1110                1115                1120

Gln Phe Lys Leu Leu Ala Gly Asn Leu Ser Leu Lys Glu Gly Val Ala
                1125                1130                1135

Asp Glu Val Gly Asp Ala Asn Arg Ser Tyr Ser Asp Glu Asp Gln Ser
            1140                1145                1150

Ser Ser Asn Ile Glu Glu Phe Asp Lys Leu Gln Glu Gly Leu Asp Ser
        1155                1160                1165

Ser Gly Asp Pro Lys Leu Cys Pro Ile Pro Met Thr Pro Asn Gly His
    1170                1175                1180

Leu Asp Pro Ser Leu Pro Leu Gly Gly His Leu Gly Pro Ala Gly Ala
1185                1190                1195                1200

Ala Gly Pro Ala Pro Arg Leu Ser Leu Gln Pro Asp Pro Met Leu Val
                1205                1210                1215

Ala Leu Gly Ser Arg Lys Ser Ser Val Met Ser Leu Gly Arg Met Ser
            1220                1225                1230

Tyr Asp Gln Arg Ser Leu Val Gly Gly Leu Arg Ala Thr Ala Gly Val
        1235                1240                1245

Gln Ala Ala Phe Gly His Leu Val Pro Gln Pro Trp Val Cys Leu Trp
    1250                1255                1260

Gly Ala Asp Pro Asn Gly Asn Ser Phe Gln Ser Ser Ser Arg Ser Ser
1265                1270                1275                1280

Tyr Tyr Gly Pro Trp Gly Arg Ser Ala Ala Trp Ala Ser Arg Arg Ser
                1285                1290                1295

Ser Trp Asn Ser Leu Lys His Lys Pro Pro Ser Ala Glu His Glu Ser
            1300                1305                1310

Leu Leu Ser Ala Glu Arg Gly Gly Gly Ala Arg Val Cys Glu Val Ala
        1315                1320                1325

Ala Asp Glu Gly Pro Pro Arg Ala Ala Pro Leu His Thr Pro His Ala
    1330                1335                1340
```

-continued

```
His His Val His His Gly Pro His Leu Ala His Arg His Arg His His
1345                1350                1355                1360

Arg Arg Thr Leu Ser Leu Asp Asn Arg Asp Ser Val Asp Leu Ala Glu
                1365                1370                1375

Leu Val Pro Ala Val Gly Ala His Pro Arg Ala Ala Trp Arg Ala Ala
            1380                1385                1390

Gly Pro Ala Pro Gly His Glu Asp Cys Asn Gly Arg Met Pro Ser Ile
        1395                1400                1405

Ala Lys Asp Val Phe Thr Lys Met Gly Asp Arg Gly Asp Arg Gly Glu
    1410                1415                1420

Asp Glu Glu Glu Ile Asp Tyr Val Ser Gly Gly Gly Ala Glu Gly Asp
1425                1430                1435                1440

Leu Thr Leu Cys Phe Arg Val Arg Lys Met Ile Asp Val Tyr Lys Pro
                1445                1450                1455

Asp Trp Cys Glu Val Arg Glu Asp Trp Ser Val Tyr Leu Phe Ser Pro
            1460                1465                1470

Glu Asn Arg Leu Arg Asp Leu Gly Trp Val Ser Leu Glu Cys Gln Gly
        1475                1480                1485

Lys Val Gly Asp Leu Val Val Trp Val Tyr Gly Gln Arg Arg Gln Arg
    1490                1495                1500

Gln Thr Ile Ile Ala His Lys Leu Phe Asp Tyr Val Val Leu Ala Phe
1505                1510                1515                1520

Ile Phe Leu Asn Cys Ile Thr Ile Ala Leu Glu Arg Pro Gln Ile Glu
                1525                1530                1535

Ala Gly Ser Thr Glu Arg Ile Phe Leu Thr Val Ser Asn Tyr Ile Phe
            1540                1545                1550

Thr Ala Ile Phe Val Gly Glu Met Thr Leu Lys Val Val Ser Leu Gly
        1555                1560                1565

Leu Tyr Phe Gly Glu Gln Ala Tyr Leu Arg Ser Ser Trp Asn Val Leu
    1570                1575                1580

Asp Gly Phe Leu Val Phe Val Ser Ile Ile Asp Ile Val Val Ser Leu
1585                1590                1595                1600

Ala Ser Ala Gly Gly Ala Lys Ile Leu Gly Val Leu Arg Val Leu Arg
                1605                1610                1615

Leu Leu Arg Thr Leu Arg Pro Leu Arg Val Ile Ser Arg Ala Pro Gly
            1620                1625                1630

Leu Lys Leu Val Val Glu Thr Leu Ile Ser Ser Leu Lys Pro Ile Gly
        1635                1640                1645

Asn Ile Val Leu Ile Cys Cys Ala Phe Phe Ile Ile Phe Gly Ile Leu
    1650                1655                1660

Gly Val Gln Leu Phe Lys Gly Lys Phe Tyr His Cys Leu Gly Val Asp
1665                1670                1675                1680

Thr Arg Asn Ile Thr Asn Arg Ser Asp Cys Met Ala Ala Asn Tyr Arg
                1685                1690                1695

Trp Val His His Lys Tyr Asn Phe Asp Asn Leu Gly Gln Ala Leu Met
            1700                1705                1710

Ser Leu Phe Val Leu Ala Ser Lys Asp Gly Trp Val Asn Ile Met Tyr
        1715                1720                1725

Asn Gly Leu Asp Ala Val Ala Val Asp Gln Gln Pro Val Thr Asn His
    1730                1735                1740

Asn Pro Trp Met Leu Leu Tyr Phe Ile Ser Phe Leu Leu Ile Val Ser
1745                1750                1755                1760
```

-continued

```
Phe Phe Val Leu Asn Met Phe Val Gly Val Val Val Glu Asn Phe His
                1765                1770                1775

Lys Cys Arg Gln His Gln Glu Ala Glu Glu Ala Arg Arg Arg Glu Glu
            1780                1785                1790

Lys Arg Leu Arg Arg Leu Glu Lys Lys Arg Arg Lys Ala Gln Arg Leu
        1795                1800                1805

Pro Tyr Tyr Ala Thr Tyr Cys His Thr Arg Leu Leu Ile His Ser Met
    1810                1815                1820

Cys Thr Ser His Tyr Leu Asp Ile Phe Ile Thr Phe Ile Ile Cys Leu
1825                1830                1835                1840

Asn Val Val Thr Met Ser Leu Glu His Tyr Asn Gln Pro Thr
                1845                1850


<210> SEQ ID NO 19
<211> LENGTH: 567
<212> TYPE: DNA
<213> ORGANISM: Homo sapiens

<400> SEQUENCE: 19

atgcggatcc tggtgaacct gctcctggac acactgccca tgctggggaa tgtcctgctg      60

ctctgcttct ttgtcttctt cacctttggc atcataggtg tgcagctctg ggcgggcctg     120

ctgcgtaacc gctgcttcct ggaggagaac ttcaccatac aaggggatgt ggccttgccc     180

ccatactacc agccggagga ggatgatgag atgcccttca tctgctccct gtcgggcgac     240

aatgggataa tgggctgcca tgagatcccc ccgctcaagg agcagggccg tgagtgctgc     300

ctgtccaagg acgacgtcta cgactttggg gcggggcgcc aggacctcaa tgccagcggc     360

ctctgtgtca actggaaccg ttactacaat gtgtgccgca cgggcagcgc caaccccccac     420

aagggtgcca tcagctttga caacatcggt tatgcttgga ttgtcatctt ccaggtgatc     480

actctggaag gctgggtggc gatcatgtac tacgtgatgg atgctctctc cttctacaac     540

ttcgtctact tcatcctgct tatcata                                         567


<210> SEQ ID NO 20
<211> LENGTH: 189
<212> TYPE: PRT
<213> ORGANISM: Homo sapiens

<400> SEQUENCE: 20

Met Arg Ile Leu Val Asn Leu Leu Leu Asp Thr Leu Pro Met Leu Gly
 1               5                  10                  15

Asn Val Leu Leu Leu Cys Phe Phe Val Phe Phe Thr Phe Gly Ile Ile
            20                  25                  30

Gly Val Gln Leu Trp Ala Gly Leu Leu Arg Asn Arg Cys Phe Leu Glu
        35                  40                  45

Glu Asn Phe Thr Ile Gln Gly Asp Val Ala Leu Pro Pro Tyr Tyr Gln
    50                  55                  60

Pro Glu Glu Asp Asp Glu Met Pro Phe Ile Cys Ser Leu Ser Gly Asp
65                  70                  75                  80

Asn Gly Ile Met Gly Cys His Glu Ile Pro Pro Leu Lys Glu Gln Gly
                85                  90                  95

Arg Glu Cys Cys Leu Ser Lys Asp Asp Val Tyr Asp Phe Gly Ala Gly
            100                 105                 110

Arg Gln Asp Leu Asn Ala Ser Gly Leu Cys Val Asn Trp Asn Arg Tyr
        115                 120                 125

Tyr Asn Val Cys Arg Thr Gly Ser Ala Asn Pro His Lys Gly Ala Ile
```

-continued

```
    130                 135                 140

Ser Phe Asp Asn Ile Gly Tyr Ala Trp Ile Val Ile Phe Gln Val Ile
145                 150                 155                 160

Thr Leu Glu Gly Trp Val Ala Ile Met Tyr Tyr Val Met Asp Ala Leu
                165                 170                 175

Ser Phe Tyr Asn Phe Val Tyr Phe Ile Leu Leu Ile Ile
            180                 185


<210> SEQ ID NO 21
<211> LENGTH: 567
<212> TYPE: DNA
<213> ORGANISM: Rattus

<400> SEQUENCE: 21

atgcggatcc tggtgaacct gctgctcgac acgctgccca tgctggggaa cgtgctcctg      60

ctctgtttct tcgtcttctt catcttcggc atcattggcg tgcagctctg ggcaggcctg     120

ctacggaacc gctgcttcct ggaagaaaac ttcaccatac aaggggatgt ggccctgccc     180

ccttattacc aaccagagga ggatgacgag atgcccttta tctgctccct gactggggac     240

aatggcatca tgggctgcca cgagatcccc ccactgaagg agcagggccg ggaatgctgc     300

ctgtccaaag atgatgtgta tgacttcggg gcggggcgcc aggacctcaa cgccagcggt     360

ctgtgcgtca actggaaccg ctactacaac gtctgccgca cgggcaacgc caaccctcac     420

aagggcgcca tcaactttga caacattggc tatgcctgga ttgtgatttt ccaggtgatc     480

actctggaag gctgggtgga gatcatgtac tatgtgatgg acgcacattc tttctacaac     540

ttcatctact tcatcctgct tatcata                                          567


<210> SEQ ID NO 22
<211> LENGTH: 189
<212> TYPE: PRT
<213> ORGANISM: Rattus

<400> SEQUENCE: 22

Met Arg Ile Leu Val Asn Leu Leu Leu Asp Thr Leu Pro Met Leu Gly
 1               5                  10                  15

Asn Val Leu Leu Leu Cys Phe Phe Val Phe Phe Ile Phe Gly Ile Ile
            20                  25                  30

Gly Val Gln Leu Trp Ala Gly Leu Leu Arg Asn Arg Cys Phe Leu Glu
        35                  40                  45

Glu Asn Phe Thr Ile Gln Gly Asp Val Ala Leu Pro Pro Tyr Tyr Gln
    50                  55                  60

Pro Glu Glu Asp Asp Glu Met Pro Phe Ile Cys Ser Leu Thr Gly Asp
65                  70                  75                  80

Asn Gly Ile Met Gly Cys His Glu Ile Pro Pro Leu Lys Glu Gln Gly
                85                  90                  95

Arg Glu Cys Cys Leu Ser Lys Asp Asp Val Tyr Asp Phe Gly Ala Gly
            100                 105                 110

Arg Gln Asp Leu Asn Ala Ser Gly Leu Cys Val Asn Trp Asn Arg Tyr
        115                 120                 125

Tyr Asn Val Cys Arg Thr Gly Asn Ala Asn Pro His Lys Gly Ala Ile
    130                 135                 140

Asn Phe Asp Asn Ile Gly Tyr Ala Trp Ile Val Ile Phe Gln Val Ile
145                 150                 155                 160

Thr Leu Glu Gly Trp Val Glu Ile Met Tyr Tyr Val Met Asp Ala His
                165                 170                 175
```

-continued

```
Ser Phe Tyr Asn Phe Ile Tyr Phe Ile Leu Leu Ile Ile
            180                 185
```

<210> SEQ ID NO 23
<211> LENGTH: 7540
<212> TYPE: DNA
<213> ORGANISM: Rattus

<400> SEQUENCE: 23

```
ccgtctctgg cgcggagcgg gacgatgctg acccccttaga tcctgctcca gctgcgccga     60

gggaagaggg ggcgcccctc cccggacccc cgccctccat cgggtggccc cttttttttc    120

tcttcctctc gggggctgct tcgccgaagg tagcgcctgt tacgggcaac cggagcctgg    180

gcgcgaacga agaagccgga acaaagtgag gggaagccgc ccggctagtc ggggagcccc    240

cgggaaccca ggggaagcgg gactctacgc caggcggggc ttccctgaga cccggcgccc    300

cgcgggcagc atgccctgag ggcaggggga gctgagctga actggccctc ctggggactc    360

agcaagctct ctagagcccc ccacatgctc ccccaccggg tcccccgttg cgtgaggaca    420

cctcctctga ggggctccgc tcgcccctct tcggaccccc cggggccccg gctggccaga    480

ggatggacga ggaggaggat ggagcgggcg ccgaggagtc gggacagccc cgtagcttca    540

cgcagctcaa cgacctgtcc ggggccgggg gcggcagggg ccgggtcgac ggaaaaggac    600

ccgggcagcg cggactccga ggcggagggg ctgccgtacc cggcgctagc cccggtggtt    660

ttcttctact tgagccagga cagccgcccg cggagctggt gtctccgcac ggtctgtaac    720

ccgtggttcg agcgagtcag tatgctggtc attcttctca actgtgtgac tctgggtatg    780

ttcaggccgt gtgaggacat tgcctgtgac tcccagcgct gccggatcct gcaggccttc    840

gatgacttca tctttgcctt ctttgctgtg gaaatggtgg tgaagatggt ggccttgggc    900

atctttggga agaaatgtta cctgggagac acttggaacc ggcttgactt tttcattgtc    960

attgcaggga tgctggagta ttcgctggac ctgcagaacg tcagcttctc cgcagtcagg   1020

acagtccgtg tgctgcgacc gctcagggcc attaaccggg tgcccagcat gcgcattctc   1080

gtcacattac tgctggacac cttgcctatg ctgggcaacg tcctgctgct ctgtttcttc   1140

gtctttttca tctttggcat cgtgggcgtc cagctgtggg caggactgct tcgcaaccgg   1200

tgcttcctcc ccgagaactt cagcctcccc ctgagcgtgg acctggagcc ttattaccag   1260

acagagaatg aggacgagag cccccttcatc tgctctcagc ctcgggagaa tggcatgaga   1320

tcctgcagga gtgtgcccac actgcgtggg gaaggcggtg gtggcccacc ctgcagtctg   1380

gactatgaga cctataacag ttccagcaac accacctgtg tcaactggaa ccagtactat   1440

accaactgct ctgcgggcga gcacaacccc ttcaaaggcg ccatcaactt tgacaacatt   1500

ggctatgcct ggatcgccat cttccaggtc atcacactgg agggctgggt cgacatcatg   1560

tacttcgtaa tggacgctca ctccttctac aacttcatct acttcattct tctcatcatc   1620

gtgggctcct tcttcatgat caacctgtgc ctggtggtga ttgccacgca gttctccgag   1680

accaaacagc gggagagtca gctgatgcgg gagcagcgtg tacgattcct gtccaatgct   1740

agcaccctgg caagcttctc tgagccaggc agctgctatg aggagctact caagtacctg   1800

gtgtacatcc tccgaaaagc agcccgaagg ctggcccagg tctctagggc tataggcgtg   1860

cgggctgggc tgctcagcag cccagtggcc cgtagtgggc aggagcccca gcccagtggc   1920

agctgcactc gctcacaccg tcgtctgtct gtccaccacc tggtccacca ccatcaccac   1980

caccatcacc actaccacct gggtaatggg acgctcagag ttccccgggc cagcccagag   2040
```

-continued

```
atccaggaca gggatgccaa tgggtctcgc cggctcatgc taccaccacc ctctacaccc   2100
actccctctg gggcccctcc gaggggtgcg gagtctgtac acagcttcta ccatgctgac   2160
tgccacttgg agccagtccg ttgccaggca ccccctccca gatgcccatc ggaggcatct   2220
ggtaggactg tgggtagtgg gaaggtgtac cccactgtgc ataccagccc tccaccagag   2280
atactgaagg ataaagcact agtggaggtg gcccccagcc ctgggccccc caccctcacc   2340
agcttcaaca tcccacctgg gcccttcagc tccatgcaca agctcctgga gacacagagt   2400
acgggagcct gccatagctc ctgcaaaatc tccagccctt gctccaaggc agacagtgga   2460
gcctgcgggc cggacagttg tccctactgt gcccggacag gagcaggaga gccagagtcc   2520
gctgaccatg tcatgcctga ctcagacagc gaggctgtgt atgagttcac acaggacgct   2580
cagcacagtg acctccggga tccccacagc cggcggcgac agcggagcct gggcccagat   2640
gcagagccta gttctgtgct ggctttctgg aggctgatct gtgacacatt ccggaagatc   2700
gtagatagca aatactttgg ccggggaatc atgatcgcca tcctggtcaa tacactcagc   2760
atgggcatcg agtaccacga gcagcccgag gagctcacca acgccctgga aatcagcaac   2820
atcgtcttca ccagcctctt cgccttggag atgctgctga aactgcttgt ctacggtccc   2880
tttggctaca ttaagaatcc ctacaacatc tttgatggtg tcattgtggt catcagtgtg   2940
tgggagattg tgggccagca gggaggtggc ctgtcggtgc tgcggacctt ccgcctgatg   3000
cgggtgctga agctggtgcg cttcctgccg gccctgcagc gccagctcgt ggtgctcatg   3060
aagaccatgg acaacgtggc caccttctgc atgctcctca tgctgttcat cttcatcttc   3120
agcatcctgg gcatgcatct ctttggttgc aagttcgcat ctgaacggga tggggacacg   3180
ttgccagacc ggaagaattt cgactccctg ctctgggcca tcgtcactgt ctttcagatt   3240
ctgactcagg aagactggaa taaagtcctc tacaacggca tggcctccac atcgtcttgg   3300
gctgctcttt acttcatcgc cctcatgact tttggcaact atgtgctctt taacctgctg   3360
gtggccattc ttgtggaagg attccaggca gagggagatg ccaccaagtc tgagtcagag   3420
cctgatttct tttcgcccag tgtggatggt gatggggaca gaaagaagcg cttggccctg   3480
gtggctttgg gagaacacgc ggaactacga aagagccttt tgccacccct catcatccat   3540
acggctgcga caccaatgtc acaccccaag agctccagca caggtgtggg ggaagcactg   3600
ggctctggct ctcgacgtac cagtagcagt gggtccgctg agcctggagc tgcccaccat   3660
gagatgaaat gtccgccaag tgcccgcagc tccccgcaca gtccctggag tgcggcaagc   3720
agctggacca gcaggcgctc cagcaggaac agcctgggcc gggcccccag cctaaagcgg   3780
aggagcccga gcggggagcg gaggtccctg ctgtctggag agggccagga gagtcaggat   3840
gaggaggaaa gttcagaaga ggaccgggcc agcccagcag gcagtgacca tcgccacagg   3900
ggttccttgg aacgtgaggc caagagttcc tttgacctgc ctgacactct gcaggtgccg   3960
gggctgcacc gcacagccag cggccggagc tctgcctctg agcaccaaga ctgtaatggc   4020
aagtcggctt cagggcgttt ggcccgcacc ctgaggactg atgaccccca actggatggg   4080
gatgatgaca atgatgaggg aaatctgagc aaaggggaac gcatacaagc ctgggtcaga   4140
tcccggcttc ctgcctgttg ccgagagcga gattcctggt cggcctatat ctttcctcct   4200
cagtcaaggt ttcgtctcct gtgtcaccgg atcatcaccc acaagatgtt tgaccatgtg   4260
gtcctcgtca tcatcttcct caactgtatc accatcgcta tggagcgccc caaaattgac   4320
ccccacagcg ctgagcgcat cttcctgacc ctctccaact acatcttcac ggcagtcttt   4380
```

-continued

```
ctagctgaaa tgacagtgaa ggtggtggca ctgggctggt gctttgggga gcaggcctac   4440
ctgcgcagca gctggaatgt gctggacggc ttgctggtgc tcatctccgt catcgacatc   4500
ctggtctcca tggtctccga cagcggcacc aagatccttg gcatgctgag ggtgctgcgg   4560
ctgctgcgga ccctgcgtcc actcagggtc atcagccggg cccagggact gaagctggtg   4620
gtagagactc tgatgtcatc cctcaaaccc attggcaaca ttgtggtcat ttgctgtgcc   4680
ttcttcatca tttttggaat tctcggggtg cagctcttca aagggaagtt cttcgtgtgt   4740
cagggtgagg acaccaggaa catcactaac aaatccgact gcgctgaggc cagctaccga   4800
tgggtccggc acaagtacaa ctttgacaac ctgggccagg ctctgatgtc cctgtttgtg   4860
ctggcctcca aggatggttg ggttgacatc atgtatgatg ggctggatgc tgtgggtgtg   4920
gatcagcagc ccatcatgaa ccacaacccc tggatgctgc tatacttcat ctccttcctc   4980
ctcatcgtgg ccttctttgt cctgaacatg tttgtgggcg tggtggtgga gaacttccat   5040
aagtgcagac agcaccagga ggaggaggag gcgaggcggc gtgaggagaa gcgactacgg   5100
aggctggaga aaaagagaag gagtaaggag aagcagatgg ccgaagccca gtgcaagccc   5160
tactactctg actactcgag attccggctc cttgtccacc acctgtgtac cagccactac   5220
ctggacctct tcatcactgg tgtcatcggg ctgaacgtgg tcactatggc catggaacat   5280
taccagcagc cccagatcct ggacgaggct ctgaagatct gcaattacat ctttaccgtc   5340
atctttgtct ttgagtcagt tttcaaactt gtggcctttg cgttccgccg tttcttccag   5400
gacaggtgga accagctgga cctggctatt gtgcttctgt ccatcatggg catcacactg   5460
gaggagattg aggtcaatct gtcgctgccc atcaacccca ccatcatccg tatcatgagg   5520
gtgctccgca ttgctcgagt tctgaagctg ttgaagatgg ctgtgggcat gcgggcactg   5580
ctgcacacgg tgatgcaggc cctgccccag gtggggaacc tgggacttct cttcatgtta   5640
ttgtttttca tctttgcagc tctgggcgtg gagctctttg gagacctgga gtgtgatgag   5700
acacaccctt gtgagggctt gggtcggcat gccaccttta ggaactttgg tatggccttt   5760
ctgaccctct tccgagtctc cactggtgac aactggaatg gtattatgaa ggacccttcc   5820
cgggactgtg accaggagtc cacctgctac aacactgtca tctcccctat ctactttgtg   5880
tccttcgtgc tgacggccca gtttgtgctg gtcaacgtgg tcatagctgt gctgatgaag   5940
cacctggaag aaagcaacaa agaggccaag gaggaggccg agctcgaggc cgagctggag   6000
ctggagatga agacgctcag cccgcagccc cactccccgc tgggcagccc cttcctctgg   6060
cccggggtgg agggtgtcaa cagtactgac agccctaagc ctggggctcc acacaccact   6120
gcccacattg gagcagcctc gggcttctcc cttgagcacc ccacgatggt accccacccc   6180
gaggaggtgc cagtcccccct aggaccagac ctgctgactg tgaggaagtc tggtgtcagc   6240
cggacgcact ctctgcccaa tgacagctac atgtgccgca atgggagcac tgctgagaga   6300
tccctaggac acaggggctg gggctcccc aaagcccagt caggctccat cttgtccgtt   6360
cactcccaac cagcagacac cagctgcatc ctacagcttc ccaaagatgt gcactatctg   6420
ctccagcctc atggggctcc cacctggggc gccatcccta aactacccc acctggccgc   6480
tcccctctgg ctcagaggcc tctcaggcgc caggcagcaa taaggactga ctccctggat   6540
gtgcagggcc tgggtagccg ggaagacctg ttgtcagagg tgagtgggcc ctcctgccct   6600
ctgacccggt cctcatcctt ctggggcggg tcgagcatcc aggtgcagca gcgttccggc   6660
atccagagca aagtctccaa gcacatccgc ctgccagccc cttgcccagg cctggaaccc   6720
agctgggcca aggaccctcc agagaccaga agcagcttag agctggacac ggagctgagc   6780
```

-continued

```
tggatttcag gagacctcct tcccagcagc caggaagaac ccctgttccc acgggacctg   6840

aagaagtgct acagtgtaga gacccagagc tgcaggcgca ggcctgggtt ctggctagat   6900

gaacagcgga gacactccat tgctgtcagc tgtctggaca gcggctccca accccgccta   6960

tgtccaagcc cctcaagcct cgggggccaa cctcttgggg gtcctgggag ccggcctaag   7020

aaaaaactca gcccacccag tatctctata gaccccccgg agagccaggg ctctcggccc   7080

ccatgcagtc ctggtgtctg cctcaggagg agggcgccgg ccagtgactc taaggatccc   7140

tcggtctcca gcccccttga cagcacggct gcctcaccct ccccaaagaa agacacgctg   7200

agtctctctg gtttgtcttc tgacccaaca gacatggacc cctgagtcct acccactctc   7260

ccccatcacc tttctccacc gggtgcagat cctacgtccg cctcctgggc agcgtttctg   7320

aaaagtccca cgtaagcagc aagcagccac gaggcacctc acctgccttc ttcagtggct   7380

ggtggggatg acgagcagaa cttccggaga gtcgatctga agagaacaca gccctggagc   7440

ccctgcctcc gggaagaagg aaaaggagaa gcccagtgtg gccaaggctc ccgacaccag   7500

gagctgttgg gagaagcaat acgtttgtgc agaatctcta                         7540


<210> SEQ ID NO 24
<211> LENGTH: 2287
<212> TYPE: PRT
<213> ORGANISM: Rattus

<400> SEQUENCE: 24

Met Leu Pro His Arg Val Pro Arg Cys Val Arg Thr Pro Pro Leu Arg
 1               5                  10                  15

Gly Ser Ala Arg Pro Ser Ser Asp Pro Pro Gly Pro Arg Leu Ala Arg
            20                  25                  30

Gly Trp Thr Arg Arg Arg Met Glu Arg Ala Pro Arg Ser Arg Asp Ser
        35                  40                  45

Pro Val Ala Ser Arg Ser Ser Thr Thr Cys Pro Gly Pro Gly Ala Ala
    50                  55                  60

Gly Ala Gly Ser Thr Glu Lys Asp Pro Gly Ser Ala Asp Ser Glu Ala
65                  70                  75                  80

Glu Gly Leu Pro Tyr Pro Ala Leu Ala Pro Val Val Phe Phe Tyr Leu
                85                  90                  95

Ser Gln Asp Ser Arg Pro Arg Ser Trp Cys Leu Arg Thr Val Cys Asn
            100                 105                 110

Pro Trp Phe Glu Arg Val Ser Met Leu Val Ile Leu Leu Asn Cys Val
        115                 120                 125

Thr Leu Gly Met Phe Arg Pro Cys Glu Asp Ile Ala Cys Asp Ser Gln
    130                 135                 140

Arg Cys Arg Ile Leu Gln Ala Phe Asp Asp Phe Ile Phe Ala Phe Phe
145                 150                 155                 160

Ala Val Glu Met Val Val Lys Met Val Ala Leu Gly Ile Phe Gly Lys
                165                 170                 175

Lys Cys Tyr Leu Gly Asp Thr Trp Asn Arg Leu Asp Phe Phe Ile Val
            180                 185                 190

Ile Ala Gly Met Leu Glu Tyr Ser Leu Asp Leu Gln Asn Val Ser Phe
        195                 200                 205

Ser Ala Val Arg Thr Val Arg Val Leu Arg Pro Leu Arg Ala Ile Asn
    210                 215                 220

Arg Val Pro Ser Met Arg Ile Leu Val Thr Leu Leu Leu Asp Thr Leu
225                 230                 235                 240
```

-continued

```
Pro Met Leu Gly Asn Val Leu Leu Leu Cys Phe Phe Val Phe Phe Ile
                245                 250                 255

Phe Gly Ile Val Gly Val Gln Leu Trp Ala Gly Leu Leu Arg Asn Arg
            260                 265                 270

Cys Phe Leu Pro Glu Asn Phe Ser Leu Pro Leu Ser Val Asp Leu Glu
        275                 280                 285

Pro Tyr Tyr Gln Thr Glu Asn Glu Asp Glu Ser Pro Phe Ile Cys Ser
    290                 295                 300

Gln Pro Arg Glu Asn Gly Met Arg Ser Cys Arg Ser Val Pro Thr Leu
305                 310                 315                 320

Arg Gly Glu Gly Gly Gly Gly Pro Pro Cys Ser Leu Asp Tyr Glu Thr
                325                 330                 335

Tyr Asn Ser Ser Ser Asn Thr Thr Cys Val Asn Trp Asn Gln Tyr Tyr
            340                 345                 350

Thr Asn Cys Ser Ala Gly Glu His Asn Pro Phe Lys Gly Ala Ile Asn
        355                 360                 365

Phe Asp Asn Ile Gly Tyr Ala Trp Ile Ala Ile Phe Gln Val Ile Thr
    370                 375                 380

Leu Glu Gly Trp Val Asp Ile Met Tyr Phe Val Met Asp Ala His Ser
385                 390                 395                 400

Phe Tyr Asn Phe Ile Tyr Phe Ile Leu Leu Ile Ile Val Gly Ser Phe
                405                 410                 415

Phe Met Ile Asn Leu Cys Leu Val Val Ile Ala Thr Gln Phe Ser Glu
            420                 425                 430

Thr Lys Gln Arg Glu Ser Gln Leu Met Arg Glu Gln Arg Val Arg Phe
        435                 440                 445

Leu Ser Asn Ala Ser Thr Leu Ala Ser Phe Ser Glu Pro Gly Ser Cys
    450                 455                 460

Tyr Glu Glu Leu Leu Lys Tyr Leu Val Tyr Ile Leu Arg Lys Ala Ala
465                 470                 475                 480

Arg Arg Leu Ala Gln Val Ser Arg Ala Ile Gly Val Arg Ala Gly Leu
                485                 490                 495

Leu Ser Ser Pro Val Ala Arg Ser Gly Gln Glu Pro Gln Pro Ser Gly
            500                 505                 510

Ser Cys Thr Arg Ser His Arg Arg Leu Ser Val His His Leu Val His
        515                 520                 525

His His His His His His His His Tyr His Leu Gly Asn Gly Thr Leu
    530                 535                 540

Arg Val Pro Arg Ala Ser Pro Glu Ile Gln Asp Arg Asp Ala Asn Gly
545                 550                 555                 560

Ser Arg Arg Leu Met Leu Pro Pro Pro Ser Thr Pro Thr Pro Ser Gly
                565                 570                 575

Gly Pro Pro Arg Gly Ala Glu Ser Val His Ser Phe Tyr His Ala Asp
            580                 585                 590

Cys His Leu Glu Pro Val Arg Cys Gln Ala Pro Pro Pro Arg Cys Pro
        595                 600                 605

Ser Glu Ala Ser Gly Arg Thr Val Gly Ser Gly Lys Val Tyr Pro Thr
    610                 615                 620

Val His Thr Ser Pro Pro Pro Glu Ile Leu Lys Asp Lys Ala Leu Val
625                 630                 635                 640

Glu Val Ala Pro Ser Pro Gly Pro Pro Thr Leu Thr Ser Phe Asn Ile
                645                 650                 655
```

-continued

```
Pro Pro Gly Pro Phe Ser Ser Met His Lys Leu Leu Glu Thr Gln Ser
            660                 665                 670

Thr Gly Ala Cys His Ser Ser Cys Lys Ile Ser Ser Pro Cys Ser Lys
        675                 680                 685

Ala Asp Ser Gly Ala Cys Gly Pro Asp Ser Cys Pro Tyr Cys Ala Arg
    690                 695                 700

Thr Gly Ala Gly Glu Pro Glu Ser Ala Asp His Val Met Pro Asp Ser
705                 710                 715                 720

Asp Ser Glu Ala Val Tyr Glu Phe Thr Gln Asp Ala Gln His Ser Asp
                725                 730                 735

Leu Arg Asp Pro His Ser Arg Arg Arg Gln Arg Ser Leu Gly Pro Asp
            740                 745                 750

Ala Glu Pro Ser Ser Val Leu Ala Phe Trp Arg Leu Ile Cys Asp Thr
        755                 760                 765

Phe Arg Lys Ile Val Asp Ser Lys Tyr Phe Gly Arg Gly Ile Met Ile
    770                 775                 780

Ala Ile Leu Val Asn Thr Leu Ser Met Gly Ile Glu Tyr His Glu Gln
785                 790                 795                 800

Pro Glu Glu Leu Thr Asn Ala Leu Glu Ile Ser Asn Ile Val Phe Thr
                805                 810                 815

Ser Leu Phe Ala Leu Glu Met Leu Leu Lys Leu Leu Val Tyr Gly Pro
            820                 825                 830

Phe Gly Tyr Ile Lys Asn Pro Tyr Asn Ile Phe Asp Gly Val Ile Val
        835                 840                 845

Val Ile Ser Val Trp Glu Ile Val Gly Gln Gln Gly Gly Gly Leu Ser
    850                 855                 860

Val Leu Arg Thr Phe Arg Leu Met Arg Val Leu Lys Leu Val Arg Phe
865                 870                 875                 880

Leu Pro Ala Leu Gln Arg Gln Leu Val Val Leu Met Lys Thr Met Asp
                885                 890                 895

Asn Val Ala Thr Phe Cys Met Leu Leu Met Leu Phe Ile Phe Ile Phe
            900                 905                 910

Ser Ile Leu Gly Met His Leu Phe Gly Cys Lys Phe Ala Ser Glu Arg
        915                 920                 925

Asp Gly Asp Thr Leu Pro Asp Arg Lys Asn Phe Asp Ser Leu Leu Trp
    930                 935                 940

Ala Ile Val Thr Val Phe Gln Ile Leu Thr Gln Glu Asp Trp Asn Lys
945                 950                 955                 960

Val Leu Tyr Asn Gly Met Ala Ser Thr Ser Ser Trp Ala Ala Leu Tyr
                965                 970                 975

Phe Ile Ala Leu Met Thr Phe Gly Asn Tyr Val Leu Phe Asn Leu Leu
            980                 985                 990

Val Ala Ile Leu Val Glu Gly Phe Gln Ala Glu Gly Asp Ala Thr Lys
        995                 1000                1005

Ser Glu Ser Glu Pro Asp Phe Phe Ser Pro Ser Val Asp Gly Asp Gly
    1010                1015                1020

Asp Arg Lys Lys Arg Leu Ala Leu Val Ala Leu Gly Glu His Ala Glu
1025                1030                1035                1040

Leu Arg Lys Ser Leu Leu Pro Pro Leu Ile Ile His Thr Ala Ala Thr
                1045                1050                1055

Pro Met Ser His Pro Lys Ser Ser Ser Thr Gly Val Gly Glu Ala Leu
            1060                1065                1070

Gly Ser Gly Ser Arg Arg Thr Ser Ser Ser Gly Ser Ala Glu Pro Gly
```

-continued

```
        1075                1080                1085

Ala Ala His His Glu Met Lys Cys Pro Pro Ser Ala Arg Ser Ser Pro
    1090                1095                1100

His Ser Pro Trp Ser Ala Ala Ser Ser Trp Thr Ser Arg Arg Ser Ser
1105                1110                1115                1120

Arg Asn Ser Leu Gly Arg Ala Pro Ser Leu Lys Arg Arg Ser Pro Ser
                1125                1130                1135

Gly Glu Arg Arg Ser Leu Leu Ser Gly Glu Gly Gln Glu Ser Gln Asp
            1140                1145                1150

Glu Glu Glu Ser Ser Glu Glu Asp Arg Ala Ser Pro Ala Gly Ser Asp
        1155                1160                1165

His Arg His Arg Gly Ser Leu Glu Arg Glu Ala Lys Ser Ser Phe Asp
    1170                1175                1180

Leu Pro Asp Thr Leu Gln Val Pro Gly Leu His Arg Thr Ala Ser Gly
1185                1190                1195                1200

Arg Ser Ser Ala Ser Glu His Gln Asp Cys Asn Gly Lys Ser Ala Ser
                1205                1210                1215

Gly Arg Leu Ala Arg Thr Leu Arg Thr Asp Asp Pro Gln Leu Asp Gly
            1220                1225                1230

Asp Asp Asp Asn Asp Glu Gly Asn Leu Ser Lys Gly Glu Arg Ile Gln
        1235                1240                1245

Ala Trp Val Arg Ser Arg Leu Pro Ala Cys Cys Arg Glu Arg Asp Ser
    1250                1255                1260

Trp Ser Ala Tyr Ile Phe Pro Pro Gln Ser Arg Phe Arg Leu Leu Cys
1265                1270                1275                1280

His Arg Ile Ile Thr His Lys Met Phe Asp His Val Val Leu Val Ile
                1285                1290                1295

Ile Phe Leu Asn Cys Ile Thr Ile Ala Met Glu Arg Pro Lys Ile Asp
            1300                1305                1310

Pro His Ser Ala Glu Arg Ile Phe Leu Thr Leu Ser Asn Tyr Ile Phe
        1315                1320                1325

Thr Ala Val Phe Leu Ala Glu Met Thr Val Lys Val Val Ala Leu Gly
    1330                1335                1340

Trp Cys Phe Gly Glu Gln Ala Tyr Leu Arg Ser Ser Trp Asn Val Leu
1345                1350                1355                1360

Asp Gly Leu Leu Val Leu Ile Ser Val Ile Asp Ile Leu Val Ser Met
                1365                1370                1375

Val Ser Asp Ser Gly Thr Lys Ile Leu Gly Met Leu Arg Val Leu Arg
            1380                1385                1390

Leu Leu Arg Thr Leu Arg Pro Leu Arg Val Ile Ser Arg Ala Gln Gly
        1395                1400                1405

Leu Lys Leu Val Val Glu Thr Leu Met Ser Ser Leu Lys Pro Ile Gly
    1410                1415                1420

Asn Ile Val Val Ile Cys Cys Ala Phe Phe Ile Ile Phe Gly Ile Leu
1425                1430                1435                1440

Gly Val Gln Leu Phe Lys Gly Lys Phe Phe Val Cys Gln Gly Glu Asp
                1445                1450                1455

Thr Arg Asn Ile Thr Asn Lys Ser Asp Cys Ala Glu Ala Ser Tyr Arg
            1460                1465                1470

Trp Val Arg His Lys Tyr Asn Phe Asp Asn Leu Gly Gln Ala Leu Met
        1475                1480                1485

Ser Leu Phe Val Leu Ala Ser Lys Asp Gly Trp Val Asp Ile Met Tyr
    1490                1495                1500
```

-continued

```
Asp Gly Leu Asp Ala Val Gly Val Asp Gln Gln Pro Ile Met Asn His
1505                1510                1515                1520

Asn Pro Trp Met Leu Leu Tyr Phe Ile Ser Phe Leu Leu Ile Val Ala
                1525                1530                1535

Phe Phe Val Leu Asn Met Phe Val Gly Val Val Val Glu Asn Phe His
            1540                1545                1550

Lys Cys Arg Gln His Gln Glu Glu Glu Glu Ala Arg Arg Arg Glu Glu
        1555                1560                1565

Lys Arg Leu Arg Arg Leu Glu Lys Lys Arg Arg Ser Lys Glu Lys Gln
    1570                1575                1580

Met Ala Glu Ala Gln Cys Lys Pro Tyr Tyr Ser Asp Tyr Ser Arg Phe
1585                1590                1595                1600

Arg Leu Leu Val His His Leu Cys Thr Ser His Tyr Leu Asp Leu Phe
                1605                1610                1615

Ile Thr Gly Val Ile Gly Leu Asn Val Val Thr Met Ala Met Glu His
            1620                1625                1630

Tyr Gln Gln Pro Gln Ile Leu Asp Glu Ala Leu Lys Ile Cys Asn Tyr
        1635                1640                1645

Ile Phe Thr Val Ile Phe Val Phe Glu Ser Val Phe Lys Leu Val Ala
    1650                1655                1660

Phe Ala Phe Arg Arg Phe Phe Gln Asp Arg Trp Asn Gln Leu Asp Leu
1665                1670                1675                1680

Ala Ile Val Leu Leu Ser Ile Met Gly Ile Thr Leu Glu Glu Ile Glu
                1685                1690                1695

Val Asn Leu Ser Leu Pro Ile Asn Pro Thr Ile Ile Arg Ile Met Arg
            1700                1705                1710

Val Leu Arg Ile Ala Arg Val Leu Lys Leu Leu Lys Met Ala Val Gly
        1715                1720                1725

Met Arg Ala Leu Leu His Thr Val Met Gln Ala Leu Pro Gln Val Gly
    1730                1735                1740

Asn Leu Gly Leu Leu Phe Met Leu Leu Phe Phe Ile Phe Ala Ala Leu
1745                1750                1755                1760

Gly Val Glu Leu Phe Gly Asp Leu Glu Cys Asp Glu Thr His Pro Cys
                1765                1770                1775

Glu Gly Leu Gly Arg His Ala Thr Phe Arg Asn Phe Gly Met Ala Phe
            1780                1785                1790

Leu Thr Leu Phe Arg Val Ser Thr Gly Asp Asn Trp Asn Gly Ile Met
        1795                1800                1805

Lys Asp Pro Ser Arg Asp Cys Asp Gln Glu Ser Thr Cys Tyr Asn Thr
    1810                1815                1820

Val Ile Ser Pro Ile Tyr Phe Val Ser Phe Val Leu Thr Ala Gln Phe
1825                1830                1835                1840

Val Leu Val Asn Val Val Ile Ala Val Leu Met Lys His Leu Glu Glu
                1845                1850                1855

Ser Asn Lys Glu Ala Lys Glu Glu Ala Glu Leu Glu Ala Glu Leu Glu
            1860                1865                1870

Leu Glu Met Lys Thr Leu Ser Pro Gln Pro His Ser Pro Leu Gly Ser
        1875                1880                1885

Pro Phe Leu Trp Pro Gly Val Glu Gly Val Asn Ser Thr Asp Ser Pro
    1890                1895                1900

Lys Pro Gly Ala Pro His Thr Thr Ala His Ile Gly Ala Ala Ser Gly
1905                1910                1915                1920
```

-continued

```
Phe Ser Leu Glu His Pro Thr Met Val Pro His Pro Glu Glu Val Pro
                1925                1930                1935

Val Pro Leu Gly Pro Asp Leu Leu Thr Val Arg Lys Ser Gly Val Ser
            1940                1945                1950

Arg Thr His Ser Leu Pro Asn Asp Ser Tyr Met Cys Arg Asn Gly Ser
        1955                1960                1965

Thr Ala Glu Arg Ser Leu Gly His Arg Gly Trp Gly Leu Pro Lys Ala
    1970                1975                1980

Gln Ser Gly Ser Ile Leu Ser Val His Ser Gln Pro Ala Asp Thr Ser
1985                1990                1995                2000

Cys Ile Leu Gln Leu Pro Lys Asp Val His Tyr Leu Leu Gln Pro His
                2005                2010                2015

Gly Ala Pro Thr Trp Gly Ala Ile Pro Lys Leu Pro Pro Pro Gly Arg
            2020                2025                2030

Ser Pro Leu Ala Gln Arg Pro Leu Arg Arg Gln Ala Ala Ile Arg Thr
        2035                2040                2045

Asp Ser Leu Asp Val Gln Gly Leu Gly Ser Arg Glu Asp Leu Leu Ser
    2050                2055                2060

Glu Val Ser Gly Pro Ser Cys Pro Leu Thr Arg Ser Ser Ser Phe Trp
2065                2070                2075                2080

Gly Gly Ser Ser Ile Gln Val Gln Gln Arg Ser Gly Ile Gln Ser Lys
                2085                2090                2095

Val Ser Lys His Ile Arg Leu Pro Ala Pro Cys Pro Gly Leu Glu Pro
            2100                2105                2110

Ser Trp Ala Lys Asp Pro Pro Glu Thr Arg Ser Ser Leu Glu Leu Asp
        2115                2120                2125

Thr Glu Leu Ser Trp Ile Ser Gly Asp Leu Leu Pro Ser Ser Gln Glu
    2130                2135                2140

Glu Pro Leu Phe Pro Arg Asp Leu Lys Lys Cys Tyr Ser Val Glu Thr
2145                2150                2155                2160

Gln Ser Cys Arg Arg Arg Pro Gly Phe Trp Leu Asp Glu Gln Arg Arg
                2165                2170                2175

His Ser Ile Ala Val Ser Cys Leu Asp Ser Gly Ser Gln Pro Arg Leu
            2180                2185                2190

Cys Pro Ser Pro Ser Ser Leu Gly Gly Gln Pro Leu Gly Gly Pro Gly
        2195                2200                2205

Ser Arg Pro Lys Lys Lys Leu Ser Pro Pro Ser Ile Ser Ile Asp Pro
    2210                2215                2220

Pro Glu Ser Gln Gly Ser Arg Pro Pro Cys Ser Pro Gly Val Cys Leu
2225                2230                2235                2240

Arg Arg Arg Ala Pro Ala Ser Asp Ser Lys Asp Pro Ser Val Ser Ser
                2245                2250                2255

Pro Leu Asp Ser Thr Ala Ala Ser Pro Ser Pro Lys Lys Asp Thr Leu
            2260                2265                2270

Ser Leu Ser Gly Leu Ser Ser Asp Pro Thr Asp Met Asp Pro Glx
        2275                2280                2285


<210> SEQ ID NO 25
<211> LENGTH: 8447
<212> TYPE: DNA
<213> ORGANISM: Rattus

<400> SEQUENCE: 25

cgggataatt ctgtctcatt accataggca cacaataaaa catctttacc atttctctaa     60
```

-continued

```
actcagccat tggccaaagc cagaaggaag acctgtgcat ttgcatctgg ggatccgatc    120
ctgactgatg ctctaggttg ctgcgtatac agtggaggag actgtgagaa aggaccatag    180
tagtcaagga agaaagcatc ctgggacaga gccacaatca cgagatgatt cctaccaatg    240
aacctcttcg gactgggtcc cagtgacagc gccgcccggg ctatgccacg gggacgccgc    300
tagccaccgg agcgaggtga gatgcggagg gtacgcgcgc ttactgcgcg cctgggaccc    360
tttgaacttg agctctgtgg gctccgagcc cctagggctc ccgcaaccct tcgcctcggc    420
cttgggggtg gggctgccag gctttgccgg cgggaggggg cggggggcgc atttgtctct    480
aataaggaga gacaaagaca tcccggcggc cgcggctgtt cccgcagctc cgctccgcct    540
gaggcggggc gggggcgtcg ttcctgggcc agggtcacct cctgccctct ctccgcaggt    600
gctgccctcc gccaccatga ccgagggcac gctggcagcg gacgaagtcc gggtgcccct    660
gggcgcttcg ccgccggccc ctgcagcgcc ggtgagagct tccccagcga gccctggggc    720
gccggggcgc gaggagcagg gaggatccgg gtcgggagtg ttggctcccg agagcccagg    780
gaccgagtgt ggtgcggacc tgggcgccga cgaggaacag ccggtcccat acccagctct    840
ggctgccaca gtcttcttct gcctcgggca aaccacgcgg ccgcgcagct ggtgcctccg    900
actggtttgt aacccgtggt tcgagcacgt cagcatgctg gtcatcatgc tgaactgcgt    960
gacactgggc atgttcaggc cctgtgagga tgttgagtgc cgctccgaac gttgcagcat   1020
cttggaggcc ttcgacgact tcatctttgc cttcttcgcc gtggagatgg tgatcaagat   1080
ggtggctttg ggcctgtttg ggcaaaaatg ctacctgggt gacacctgga acaggctgga   1140
cttcttcatt gtcatggcgg gcatgatgga gtactctctg gacggacaca aggtgagcct   1200
ctctgccatc cgaaccgtgc gtgtgctgcg gcccctccgc gccatcaacc gagtccccag   1260
tatgcggatc ctggtcactc tgctgctgga cacgctgccc atgcttggga atgtcctcct   1320
cctctgcttc ttcgtcttct tcatcttcgg cattgttggg gtccagctct gggctggcct   1380
gcttcggaac cgatgcttcc tggacagcgc cttcgtcagg aacaacaacc tgaccttctt   1440
gcggccatac taccagacgg aggagggtga ggagaaccct ttcatctgct cctcccgccg   1500
tgacaacggc atgcagaagt gctcgcacat ccccagccgc cgtgagcttc gagtgcagtg   1560
cacactcggc tgggaggcct atgggcagcc acaggctgag gatgggggtg ctggccgcaa   1620
cgcctgtatc aactggaacc agtattacaa cgtgtgccgc tcgggggaat tcaaccctca   1680
caacggtgcc atcaacttcg acaacattgg ctacgcttgg attgccatct tccaggtcat   1740
cacactggag ggctgggtgg acatcatgta ctacgtcatg gatgcccact cgttctacaa   1800
cttcatctac ttcatcctcc tcatcattat gggctccttc ttcatgatca acctgtgcct   1860
ggtggtgata gccacacagt tctcagagac aaagcaaagg gaaaaccagc tgatgcgaga   1920
acagcgggcc cgctatctgt ccaacgacag cactctggcc agcttctcag agcccggcag   1980
ctgctacgag gagctcctca agtatgtagg ccacatcttc cggaaggtta aacgccgtag   2040
cctgcgtctt tatgcccgct ggcagagccg ctggcgtaag aaggtggatc ccagcagtac   2100
cgtgcatggc caaggccctg ggcggcggcc acgacgggca ggcaggcgta cagcttcagt   2160
gcaccatctg gtctaccacc accaccacca ccatcaccac cattaccact ttagccacgg   2220
tggcccacgc aggcccagcc cagagccagg tgctggtgac aacaggttgg tcagggcctg   2280
tgcgccaccc tcgccgccat ccccaggcca tgggccacca gactctgagt ctgtgcacag   2340
tatctaccat gctgactgcc acgtggaggg gccgcaggaa cgagcccgag tggcacactc   2400
catagccact gctgctagcc tcaagctggc ctcaggtttg ggtaccatga actaccccac   2460
```

-continued catcctacct tcaggaacag tcaacagcaa aggtggcacc agctcacgac ccaaggggct 2520
acgaggtgct ggcgccccag gggctgcagt acacagccct ctgagcctgg gaagccccag 2580
accctatgag aagatccagg atgtggtggg agaacaagga ctaggccgag cctctagcca 2640
cctgtcaggc ctgagtgtgc cttgcccccct gcccagcccc caggctggca cgctgacctg 2700
tgagctgaag agctgcccat attgtgccag cgccctggag gaccccgagt ttgaattcag 2760
tggctcagag agcggggact cggatgccca cggagtctat gagtttaccc aggatgtacg 2820
gcatggggat tgtcgggacc ctgtgcagca gccccatgaa gtgggcacac caggccacag 2880
caatgagcgg cggcggacac cactgcggaa ggcctcacaa ccaggaggga taggccacct 2940
ctgggcatcc ttcagtggca agctacgtcg cattgtagac agcaagtact tcaaccgagg 3000
catcatggca gccatcctcg tcaatactct gagcatgggc gttgagtatc atgaacagcc 3060
tgaggagctg accaacgccc tggagataag caacatcgtg ttcaccagca tgtttgcctt 3120
ggagatgcta ctgaagctgc tggcctgcgg cccactggga tacatccgga acccctacaa 3180
catcttcgat ggcattgttg tcgtcataag tgtctgggag atcgtggggc aggcagacgg 3240
tggccagtct gtgctgcgca ccttcaggct gctgcgggtg ctgaagctgg tgcgcttcct 3300
gccggccctg cggcgccagc tcgtggtgct catgaggacc atggacaacg tggccacctt 3360
ctgcatgctc ctcatgctgt tcatcttcat cttcagcatc ctgggcatgc acctgttcgg 3420
ctgtaagttc agcctgaaga cagactctgg agacaccgtc cctgacagga agaacttcga 3480
ctccctactg tgggccatcg tcaccgtgtt tcagatcttg acacaggaag actggaacgt 3540
ggttctgtac aacggcatgg cctccacttc gtcctgggcc gccctttact ttgtggccct 3600
catgaccttt gggaactatg tgctcttcaa cctgctggta gccatcctgg tggaaggttt 3660
ccaggcagag ggtgacgcca ccagatctga caccgacgag gataagacgt ctacccagct 3720
agagggagat ttcgataagc tcagagatct tcgagccaca gagatgaaga tgtattcact 3780
ggcagtgacc cctaacgggc acctagaggg ccgaggcagc ctgccgccgc ccctcatcac 3840
tcacacggca gctacgccta tgcctactcc caaaagctcc ccaaacctgg acgtggccca 3900
tgctctcctg gactctcggc gcagcagcag cggctctgtg gacccccagc tgggggacca 3960
gaagtctctg gccagcctcc gcagctcccc ttgcacccca tggggcccca acagcgctgg 4020
gagcagcagg cgctccagtt ggaacagcct gggccgcgca cccagcctca aacgccgcag 4080
ccagtgtggg gagcgcgagt ccctgctctc tggagagggg aagggcagca ccgatgacga 4140
ggccgaggac agcagaccaa gcacgggaac ccacccaggg gcctcgccag ggccccgagc 4200
cacgccactg cggcgtgccg agtcattgga ccaccgcagc acgctggacc tgtgtccacc 4260
acggcctgcg cctcctgccg tccaagttca tgactgcaac gggcagatgg tggccctgcc 4320
cagcgagttc tttctgcgca tcgacagcca caaggaggat gcagcggagt ttgatgatga 4380
catagaggat agctgctgct tccgtctaca caaagtgctg gaaccctatg caccccagtg 4440
gtgccgtagc cgggagtcct gggccctgta tctcttccca ccgcagaaca ggctacgcgt 4500
ctcctgccag aaagtcatcg cacacaagat gtttgaccac gtggtccttg tcttcatctt 4560
cctcaactgt atcaccattg ctctggagag gccagacatt gacccaggca gcactgagcg 4620
ggccttcctc agcgtctcca actacatctt cacagccatc ttcgtggtgg agatgatggt 4680
gaaggtggta gccctgggac tgctgtgggg tgaacatgcc tacctacaga gcagttggaa 4740
tgtgctggac gggctgcttg tcctggtatc cctggttgac atcatcgtgg ccatggcctc 4800

-continued

```
agctggcggt gccaagatcc taggcgtcct gcgtgtcgtg cgcctgctgc ggaccctgag   4860
gcctctgagg gtcatcagcc gagctccagg cctcaagctg gttgtagaga ctctgatatc   4920
atcgctcagg cccattggga acatcgtcct catctgctgc gccttcttca tcatctttgg   4980
catcctcggg gtgcagcttt tcaagggcaa attctactac tgcgagggca cagataccag   5040
gaatatcacc accaaggccg agtgccatgc tgcccactac cgctgggtga ggcgcaaata   5100
caactttgac aacctgggtc aggcgctgat gtctctgttc gtgctgtcat ctaaggatgg   5160
ctgggtaaac atcatgtatg acgggctgga tgccgtgggc atcgaccagc agcccgtgca   5220
gaaccacaac ccctggatgc tgctctactt catctccttc ctgctcatcg tcagcttctt   5280
cgtgctcaac atgtttgtgg gcgtggtggt ggagaacttc cacaagtgcc ggcagcacca   5340
ggaggctgag gaggctcggc gccgggagga gaaacggctg cggcgcctgg agaggaggcg   5400
caggaaggcc cagcgccggc cctactacgc agactattca cacactcgcc gctccatcca   5460
ttcgctgtgc accagccact acctggacct cttcatcacc ttcatcatct gcctcaatgt   5520
catcaccatg tccatggagc actacaacca gcccaagtcc ctggatgagg ccctcaagta   5580
ctgcaactac gtctttacca tcgtcttcgt ctttgaggct gcactgaagc tggtggcctt   5640
tgggttccgg aggttcttca aggacaggtg gaaccagctg gacttggcca tcgtcctcct   5700
atccatcatg ggcattgcgc tggaggagat tgagatgaac gccgccctgc ccatcaatcc   5760
caccatcatc cgcatcatgc gtgtgcttcg aatcgcccgt gtgctgaagc tactgaagat   5820
ggccacaggc atgcgcgcct tgctggatac tgtggttcaa gctctgcctc aggtagggaa   5880
ccttggtctt cttttcatgc tcctgttttt tatctatgct gccctgggag tggagctgtt   5940
tgggaggcta gagtgcagcg aggataaccc ctgcgagggc ctgagcaggc acgctacctt   6000
caccaacttc ggcatggcct tcctcacact gttccgagtg tccactgggg acaactggaa   6060
tgggattatg aaggataccc tccgtgagtg tacccgtgag gacaagcact gcctcagcta   6120
cctgcccgcg ctctcacccg tctacttcgt caccttcatg ctggtggctc agttcgtgct   6180
ggtcaatgtg gtggtggccg tgctcatgaa gcacctggag gagagcaaca aggaggcccg   6240
cgaggatgca gagatggacg ccgagatcga gctggagatg gcacaggggt ccacagccca   6300
gcccccacct acagcacagg aaagccaagg tacccagcca gacaccccga acctcctggt   6360
cgtgcgaaaa gtatctgtgt ccaggatgct ctcgctgccc aatgacagct acatgttcag   6420
gccggtggct cccgcggctg ccccacattc ccacccactg caggaagtgg agatggagac   6480
ctacacaggc ccggtcacct ctgctcactc gccacccctg gagccccgcg cctctttcca   6540
ggtcccatca gccgcgtcct ccccagccag ggtcagtgac cccctttgtg ccctttcacc   6600
ccggggtaca ccccgctctc tgagtctctc acggatactc tgcagacagg aggccatgca   6660
ctctgagtcc ctggaaggga aggttgatga tgttggagga gacagcatcc cagactacac   6720
agagcctgct gaaaatatgt ccacgagcca ggcatcaaca ggtgccccga ggtcccctcc   6780
gtgctccccg cgacctgcca gcgtccgtac ccgcaagcac acgtttgggc aacgctgcat   6840
ctccagccgc cctcccaccc tgggaggaga tgaggctgaa gcagcagacc cagcagatga   6900
ggaggtcagc cacatcacca gctcagccca cccctggccg gctacagagc cccacagccc   6960
tgaggcctcc ccaacagcct ctcctgtgaa aggcacaatg ggcagtgggc gggacccacg   7020
caggttctgc agtgtagatg ctcagagctt cctggacaaa ccaggtcggc cagatgcaca   7080
acggtggtcc tcagtggaac tggataacgg agaaagccac ctagagtccg gggaagtgag   7140
gggccgggcc tcagagctcg aaccagctct tgggtcacga aggaagaaga agatgagccc   7200
```

-continued

```
tccctgcatc tccattgaac ctcccactaa ggatgagggc tcttcccggc cccctgcagc   7260

cgaaggaggc aacactaccc tgaggcgccg aaccccatcc tgtgaggctg ccctccatag   7320

ggactgccca gagcctacag aaggcccagg caccggaggg gaccctgtag ccaagggtga   7380

gcgctggggc caggcctctt gccgagcaga gcatctgact gtccccaact ttgcctttga   7440

gcctctggac atgggcggac ctggtggaga ctgtttcttg gacagtgacc aaagtgtgac   7500

cccagaaccc agagtttcct ctttgggggc tatagtgcct ctgatactag aaactgaact   7560

ttctatgccc tctcctgact gcccagagaa ggaacaagga ctgtacctca ctgtgcccca   7620

gaccccccttg aagaaaccag ggtctacccc agccactcct gccccagatg acagtggaga   7680

tgagcctgtg tagatggggc tgcgtgtcca cagggctttg gcattgaggt tgttggctcc   7740

tgcagggtgg tagggccatg agtggaccct gcttaggccc cactaaggca gagggaccgg   7800

gagataacca tcccaggaga ggcagcagac atcccgtctc tgcaccatga cacaggagca   7860

gcctcgggcc ccacgagcct ccctcgtggt gattcaggtt tgggttttcc tgagttttaa   7920

ccaccaccag aagctgtacc aggaccaggt catcagtctc aggaggagag gctgtgtcct   7980

gggaaggacc agtaattcct cacaggcacc acagctccat ccatgtgaca cacaggtttc   8040

cgacagggag tacagcttga gcctgtgtac attgggtcct gcagccaccg cacccaatat   8100

caccttcgtt cacagtcctg tttctgtcca ccactcggca tccttccctc tcacagtgcc   8160

cctcccccat tccatcccct tagatggtct agaactttgc agtgaccctg ggaagtactg   8220

acccatgcaa taagacattg cagtcccaac tgaggtgggg cttcccatcc attccaggct   8280

gttgggctca acattcattt gacatccatt tgctttatgt catccgtttc tacaaattca   8340

ggttaaatgt tgcaataatc tgatgcagaa aacttggctt cctaagtcaa agctgagggg   8400

aggggagggg aggggcaagg caaatctgaa taaacactaa cttattg                 8447
```

<210> SEQ ID NO 26
<211> LENGTH: 2359
<212> TYPE: PRT
<213> ORGANISM: Rattus

<400> SEQUENCE: 26

```
Met Thr Glu Gly Thr Leu Ala Ala Asp Glu Val Arg Val Pro Leu Gly
 1               5                  10                  15

Ala Ser Pro Pro Ala Pro Ala Ala Pro Val Arg Ala Ser Pro Ala Ser
            20                  25                  30

Pro Gly Ala Pro Gly Arg Glu Glu Gln Gly Gly Ser Gly Ser Gly Val
        35                  40                  45

Leu Ala Pro Glu Ser Pro Gly Thr Glu Cys Gly Ala Asp Leu Gly Ala
    50                  55                  60

Asp Glu Glu Gln Pro Val Pro Tyr Pro Ala Leu Ala Ala Thr Val Phe
65                  70                  75                  80

Phe Cys Leu Gly Gln Thr Thr Arg Pro Arg Ser Trp Cys Leu Arg Leu
                85                  90                  95

Val Cys Asn Pro Trp Phe Glu His Val Ser Met Leu Val Ile Met Leu
            100                 105                 110

Asn Cys Val Thr Leu Gly Met Phe Arg Pro Cys Glu Asp Val Glu Cys
        115                 120                 125

Arg Ser Glu Arg Cys Ser Ile Leu Glu Ala Phe Asp Asp Phe Ile Phe
    130                 135                 140

Ala Phe Phe Ala Val Glu Met Val Ile Lys Met Val Ala Leu Gly Leu
```

-continued

```
145                 150                 155                 160

Phe Gly Gln Lys Cys Tyr Leu Gly Asp Thr Trp Asn Arg Leu Asp Phe
                165                 170                 175

Phe Ile Val Met Ala Gly Met Met Glu Tyr Ser Leu Asp Gly His Lys
            180                 185                 190

Val Ser Leu Ser Ala Ile Arg Thr Val Arg Val Leu Arg Pro Leu Arg
        195                 200                 205

Ala Ile Asn Arg Val Pro Ser Met Arg Ile Leu Val Thr Leu Leu Leu
    210                 215                 220

Asp Thr Leu Pro Met Leu Gly Asn Val Leu Leu Leu Cys Phe Phe Val
225                 230                 235                 240

Phe Phe Ile Phe Gly Ile Val Gly Val Gln Leu Trp Ala Gly Leu Leu
                245                 250                 255

Arg Asn Arg Cys Phe Leu Asp Ser Ala Phe Val Arg Asn Asn Asn Leu
            260                 265                 270

Thr Phe Leu Arg Pro Tyr Tyr Gln Thr Glu Glu Gly Glu Glu Asn Pro
        275                 280                 285

Phe Ile Cys Ser Ser Arg Arg Asp Asn Gly Met Gln Lys Cys Ser His
    290                 295                 300

Ile Pro Ser Arg Arg Glu Leu Arg Val Gln Cys Thr Leu Gly Trp Glu
305                 310                 315                 320

Ala Tyr Gly Gln Pro Gln Ala Glu Asp Gly Gly Ala Gly Arg Asn Ala
                325                 330                 335

Cys Ile Asn Trp Asn Gln Tyr Tyr Asn Val Cys Arg Ser Gly Glu Phe
            340                 345                 350

Asn Pro His Asn Gly Ala Ile Asn Phe Asp Asn Ile Gly Tyr Ala Trp
        355                 360                 365

Ile Ala Ile Phe Gln Val Ile Thr Leu Glu Gly Trp Val Asp Ile Met
    370                 375                 380

Tyr Tyr Val Met Asp Ala His Ser Phe Tyr Asn Phe Ile Tyr Phe Ile
385                 390                 395                 400

Leu Leu Ile Ile Met Gly Ser Phe Phe Met Ile Asn Leu Cys Leu Val
                405                 410                 415

Val Ile Ala Thr Gln Phe Ser Glu Thr Lys Gln Arg Glu Asn Gln Leu
            420                 425                 430

Met Arg Glu Gln Arg Ala Arg Tyr Leu Ser Asn Asp Ser Thr Leu Ala
        435                 440                 445

Ser Phe Ser Glu Pro Gly Ser Cys Tyr Glu Glu Leu Leu Lys Tyr Val
    450                 455                 460

Gly His Ile Phe Arg Lys Val Lys Arg Arg Ser Leu Arg Leu Tyr Ala
465                 470                 475                 480

Arg Trp Gln Ser Arg Trp Arg Lys Lys Val Asp Pro Ser Ser Thr Val
                485                 490                 495

His Gly Gln Gly Pro Gly Arg Arg Pro Arg Arg Ala Gly Arg Arg Thr
            500                 505                 510

Ala Ser Val His His Leu Val Tyr His His His His His His His His
        515                 520                 525

His Tyr His Phe Ser His Gly Gly Pro Arg Arg Pro Ser Pro Glu Pro
    530                 535                 540

Gly Ala Gly Asp Asn Arg Leu Val Arg Ala Cys Ala Pro Pro Ser Pro
545                 550                 555                 560

Pro Ser Pro Gly His Gly Pro Pro Asp Ser Glu Ser Val His Ser Ile
                565                 570                 575
```

-continued

```
Tyr His Ala Asp Cys His Val Glu Gly Pro Gln Glu Arg Ala Arg Val
            580                 585                 590

Ala His Ser Ile Ala Thr Ala Ala Ser Leu Lys Leu Ala Ser Gly Leu
        595                 600                 605

Gly Thr Met Asn Tyr Pro Thr Ile Leu Pro Ser Gly Thr Val Asn Ser
    610                 615                 620

Lys Gly Gly Thr Ser Ser Arg Pro Lys Gly Leu Arg Gly Ala Gly Ala
625                 630                 635                 640

Pro Gly Ala Ala Val His Ser Pro Leu Ser Leu Gly Ser Pro Arg Pro
                645                 650                 655

Tyr Glu Lys Ile Gln Asp Val Val Gly Glu Gln Gly Leu Gly Arg Ala
            660                 665                 670

Ser Ser His Leu Ser Gly Leu Ser Val Pro Cys Pro Leu Pro Ser Pro
        675                 680                 685

Gln Ala Gly Thr Leu Thr Cys Glu Leu Lys Ser Cys Pro Tyr Cys Ala
    690                 695                 700

Ser Ala Leu Glu Asp Pro Glu Phe Glu Phe Ser Gly Ser Glu Ser Gly
705                 710                 715                 720

Asp Ser Asp Ala His Gly Val Tyr Glu Phe Thr Gln Asp Val Arg His
                725                 730                 735

Gly Asp Cys Arg Asp Pro Val Gln Gln Pro His Glu Val Gly Thr Pro
            740                 745                 750

Gly His Ser Asn Glu Arg Arg Arg Thr Pro Leu Arg Lys Ala Ser Gln
        755                 760                 765

Pro Gly Gly Ile Gly His Leu Trp Ala Ser Phe Ser Gly Lys Leu Arg
    770                 775                 780

Arg Ile Val Asp Ser Lys Tyr Phe Asn Arg Gly Ile Met Ala Ala Ile
785                 790                 795                 800

Leu Val Asn Thr Leu Ser Met Gly Val Glu Tyr His Glu Gln Pro Glu
                805                 810                 815

Glu Leu Thr Asn Ala Leu Glu Ile Ser Asn Ile Val Phe Thr Ser Met
            820                 825                 830

Phe Ala Leu Glu Met Leu Leu Lys Leu Leu Ala Cys Gly Pro Leu Gly
        835                 840                 845

Tyr Ile Arg Asn Pro Tyr Asn Ile Phe Asp Gly Ile Val Val Val Ile
    850                 855                 860

Ser Val Trp Glu Ile Val Gly Gln Ala Asp Gly Gly Gln Ser Val Leu
865                 870                 875                 880

Arg Thr Phe Arg Leu Leu Arg Val Leu Lys Leu Val Arg Phe Leu Pro
                885                 890                 895

Ala Leu Arg Arg Gln Leu Val Val Leu Met Arg Thr Met Asp Asn Val
            900                 905                 910

Ala Thr Phe Cys Met Leu Leu Met Leu Phe Ile Phe Ile Phe Ser Ile
        915                 920                 925

Leu Gly Met His Leu Phe Gly Cys Lys Phe Ser Leu Lys Thr Asp Ser
    930                 935                 940

Gly Asp Thr Val Pro Asp Arg Lys Asn Phe Asp Ser Leu Leu Trp Ala
945                 950                 955                 960

Ile Val Thr Val Phe Gln Ile Leu Thr Gln Glu Asp Trp Asn Val Val
                965                 970                 975

Leu Tyr Asn Gly Met Ala Ser Thr Ser Ser Trp Ala Ala Leu Tyr Phe
            980                 985                 990
```

-continued

```
Val Ala Leu Met Thr Phe Gly Asn Tyr Val Leu Phe Asn Leu Leu Val
        995                 1000                1005

Ala Ile Leu Val Glu Gly Phe Gln Ala Glu Gly Asp Ala Thr Arg Ser
    1010                1015                1020

Asp Thr Asp Glu Asp Lys Thr Ser Thr Gln Leu Glu Gly Asp Phe Asp
1025                1030                1035                1040

Lys Leu Arg Asp Leu Arg Ala Thr Glu Met Lys Met Tyr Ser Leu Ala
                1045                1050                1055

Val Thr Pro Asn Gly His Leu Glu Gly Arg Gly Ser Leu Pro Pro Pro
            1060                1065                1070

Leu Ile Thr His Thr Ala Ala Thr Pro Met Pro Thr Pro Lys Ser Ser
        1075                1080                1085

Pro Asn Leu Asp Val Ala His Ala Leu Leu Asp Ser Arg Arg Ser Ser
    1090                1095                1100

Ser Gly Ser Val Asp Pro Gln Leu Gly Asp Gln Lys Ser Leu Ala Ser
1105                1110                1115                1120

Leu Arg Ser Ser Pro Cys Thr Pro Trp Gly Pro Asn Ser Ala Gly Ser
                1125                1130                1135

Ser Arg Arg Ser Ser Trp Asn Ser Leu Gly Arg Ala Pro Ser Leu Lys
            1140                1145                1150

Arg Arg Ser Gln Cys Gly Glu Arg Glu Ser Leu Leu Ser Gly Glu Gly
        1155                1160                1165

Lys Gly Ser Thr Asp Asp Glu Ala Glu Asp Ser Arg Pro Ser Thr Gly
    1170                1175                1180

Thr His Pro Gly Ala Ser Pro Gly Pro Arg Ala Thr Pro Leu Arg Arg
1185                1190                1195                1200

Ala Glu Ser Leu Asp His Arg Ser Thr Leu Asp Leu Cys Pro Pro Arg
                1205                1210                1215

Pro Ala Pro Pro Ala Val Gln Val His Asp Cys Asn Gly Gln Met Val
            1220                1225                1230

Ala Leu Pro Ser Glu Phe Phe Leu Arg Ile Asp Ser His Lys Glu Asp
        1235                1240                1245

Ala Ala Glu Phe Asp Asp Asp Ile Glu Asp Ser Cys Cys Phe Arg Leu
    1250                1255                1260

His Lys Val Leu Glu Pro Tyr Ala Pro Gln Trp Cys Arg Ser Arg Glu
1265                1270                1275                1280

Ser Trp Ala Leu Tyr Leu Phe Pro Pro Gln Asn Arg Leu Arg Val Ser
                1285                1290                1295

Cys Gln Lys Val Ile Ala His Lys Met Phe Asp His Val Val Leu Val
            1300                1305                1310

Phe Ile Phe Leu Asn Cys Ile Thr Ile Ala Leu Glu Arg Pro Asp Ile
        1315                1320                1325

Asp Pro Gly Ser Thr Glu Arg Ala Phe Leu Ser Val Ser Asn Tyr Ile
    1330                1335                1340

Phe Thr Ala Ile Phe Val Val Glu Met Met Val Lys Val Val Ala Leu
1345                1350                1355                1360

Gly Leu Leu Trp Gly Glu His Ala Tyr Leu Gln Ser Ser Trp Asn Val
                1365                1370                1375

Leu Asp Gly Leu Leu Val Leu Val Ser Leu Val Asp Ile Ile Val Ala
            1380                1385                1390

Met Ala Ser Ala Gly Gly Ala Lys Ile Leu Gly Val Leu Arg Val Val
        1395                1400                1405

Arg Leu Leu Arg Thr Leu Arg Pro Leu Arg Val Ile Ser Arg Ala Pro
```

-continued

```
    1410                1415                1420

Gly Leu Lys Leu Val Val Glu Thr Leu Ile Ser Ser Leu Arg Pro Ile
1425                1430                1435                1440

Gly Asn Ile Val Leu Ile Cys Cys Ala Phe Phe Ile Ile Phe Gly Ile
                1445                1450                1455

Leu Gly Val Gln Leu Phe Lys Gly Lys Phe Tyr Tyr Cys Glu Gly Thr
            1460                1465                1470

Asp Thr Arg Asn Ile Thr Thr Lys Ala Glu Cys His Ala Ala His Tyr
        1475                1480                1485

Arg Trp Val Arg Arg Lys Tyr Asn Phe Asp Asn Leu Gly Gln Ala Leu
    1490                1495                1500

Met Ser Leu Phe Val Leu Ser Ser Lys Asp Gly Trp Val Asn Ile Met
1505                1510                1515                1520

Tyr Asp Gly Leu Asp Ala Val Gly Ile Asp Gln Gln Pro Val Gln Asn
                1525                1530                1535

His Asn Pro Trp Met Leu Leu Tyr Phe Ile Ser Phe Leu Leu Ile Val
            1540                1545                1550

Ser Phe Phe Val Leu Asn Met Phe Val Gly Val Val Val Glu Asn Phe
        1555                1560                1565

His Lys Cys Arg Gln His Gln Glu Ala Glu Glu Ala Arg Arg Arg Glu
    1570                1575                1580

Glu Lys Arg Leu Arg Arg Leu Glu Arg Arg Arg Arg Lys Ala Gln Arg
1585                1590                1595                1600

Arg Pro Tyr Tyr Ala Asp Tyr Ser His Thr Arg Arg Ser Ile His Ser
                1605                1610                1615

Leu Cys Thr Ser His Tyr Leu Asp Leu Phe Ile Thr Phe Ile Ile Cys
            1620                1625                1630

Leu Asn Val Ile Thr Met Ser Met Glu His Tyr Asn Gln Pro Lys Ser
        1635                1640                1645

Leu Asp Glu Ala Leu Lys Tyr Cys Asn Tyr Val Phe Thr Ile Val Phe
    1650                1655                1660

Val Phe Glu Ala Ala Leu Lys Leu Val Ala Phe Gly Phe Arg Arg Phe
1665                1670                1675                1680

Phe Lys Asp Arg Trp Asn Gln Leu Asp Leu Ala Ile Val Leu Leu Ser
                1685                1690                1695

Ile Met Gly Ile Ala Leu Glu Glu Ile Glu Met Asn Ala Ala Leu Pro
            1700                1705                1710

Ile Asn Pro Thr Ile Ile Arg Ile Met Arg Val Leu Arg Ile Ala Arg
        1715                1720                1725

Val Leu Lys Leu Leu Lys Met Ala Thr Gly Met Arg Ala Leu Leu Asp
    1730                1735                1740

Thr Val Val Gln Ala Leu Pro Gln Val Gly Asn Leu Gly Leu Leu Phe
1745                1750                1755                1760

Met Leu Leu Phe Phe Ile Tyr Ala Ala Leu Gly Val Glu Leu Phe Gly
                1765                1770                1775

Arg Leu Glu Cys Ser Glu Asp Asn Pro Cys Glu Gly Leu Ser Arg His
            1780                1785                1790

Ala Thr Phe Thr Asn Phe Gly Met Ala Phe Leu Thr Leu Phe Arg Val
        1795                1800                1805

Ser Thr Gly Asp Asn Trp Asn Gly Ile Met Lys Asp Thr Leu Arg Glu
    1810                1815                1820

Cys Thr Arg Glu Asp Lys His Cys Leu Ser Tyr Leu Pro Ala Leu Ser
1825                1830                1835                1840
```

-continued

```
Pro Val Tyr Phe Val Thr Phe Met Leu Val Ala Gln Phe Val Leu Val
                1845                1850                1855

Asn Val Val Val Ala Val Leu Met Lys His Leu Glu Glu Ser Asn Lys
            1860                1865                1870

Glu Ala Arg Glu Asp Ala Glu Met Asp Ala Glu Ile Glu Leu Glu Met
        1875                1880                1885

Ala Gln Gly Ser Thr Ala Gln Pro Pro Pro Thr Ala Gln Glu Ser Gln
    1890                1895                1900

Gly Thr Gln Pro Asp Thr Pro Asn Leu Leu Val Val Arg Lys Val Ser
1905                1910                1915                1920

Val Ser Arg Met Leu Ser Leu Pro Asn Asp Ser Tyr Met Phe Arg Pro
                1925                1930                1935

Val Ala Pro Ala Ala Ala Pro His Ser His Pro Leu Gln Glu Val Glu
            1940                1945                1950

Met Glu Thr Tyr Thr Gly Pro Val Thr Ser Ala His Ser Pro Pro Leu
        1955                1960                1965

Glu Pro Arg Ala Ser Phe Gln Val Pro Ser Ala Ala Ser Ser Pro Ala
    1970                1975                1980

Arg Val Ser Asp Pro Leu Cys Ala Leu Ser Pro Arg Gly Thr Pro Arg
1985                1990                1995                2000

Ser Leu Ser Leu Ser Arg Ile Leu Cys Arg Gln Glu Ala Met His Ser
                2005                2010                2015

Glu Ser Leu Glu Gly Lys Val Asp Asp Val Gly Gly Asp Ser Ile Pro
            2020                2025                2030

Asp Tyr Thr Glu Pro Ala Glu Asn Met Ser Thr Ser Gln Ala Ser Thr
        2035                2040                2045

Gly Ala Pro Arg Ser Pro Pro Cys Ser Pro Arg Pro Ala Ser Val Arg
    2050                2055                2060

Thr Arg Lys His Thr Phe Gly Gln Arg Cys Ile Ser Ser Arg Pro Pro
2065                2070                2075                2080

Thr Leu Gly Gly Asp Glu Ala Glu Ala Ala Asp Pro Ala Asp Glu Glu
                2085                2090                2095

Val Ser His Ile Thr Ser Ser Ala His Pro Trp Pro Ala Thr Glu Pro
            2100                2105                2110

His Ser Pro Glu Ala Ser Pro Thr Ala Ser Pro Val Lys Gly Thr Met
        2115                2120                2125

Gly Ser Gly Arg Asp Pro Arg Arg Phe Cys Ser Val Asp Ala Gln Ser
    2130                2135                2140

Phe Leu Asp Lys Pro Gly Arg Pro Asp Ala Gln Arg Trp Ser Ser Val
2145                2150                2155                2160

Glu Leu Asp Asn Gly Glu Ser His Leu Glu Ser Gly Glu Val Arg Gly
                2165                2170                2175

Arg Ala Ser Glu Leu Glu Pro Ala Leu Gly Ser Arg Arg Lys Lys Lys
            2180                2185                2190

Met Ser Pro Pro Cys Ile Ser Ile Glu Pro Pro Thr Lys Asp Glu Gly
        2195                2200                2205

Ser Ser Arg Pro Pro Ala Ala Glu Gly Gly Asn Thr Thr Leu Arg Arg
    2210                2215                2220

Arg Thr Pro Ser Cys Glu Ala Ala Leu His Arg Asp Cys Pro Glu Pro
2225                2230                2235                2240

Thr Glu Gly Pro Gly Thr Gly Gly Asp Pro Val Ala Lys Gly Glu Arg
                2245                2250                2255
```

-continued

```
Trp Gly Gln Ala Ser Cys Arg Ala Glu His Leu Thr Val Pro Asn Phe
            2260                2265                2270

Ala Phe Glu Pro Leu Asp Met Gly Gly Pro Gly Gly Asp Cys Phe Leu
        2275                2280                2285

Asp Ser Asp Gln Ser Val Thr Pro Glu Pro Arg Val Ser Ser Leu Gly
    2290                2295                2300

Ala Ile Val Pro Leu Ile Leu Glu Thr Glu Leu Ser Met Pro Ser Pro
2305                2310                2315                2320

Asp Cys Pro Glu Lys Glu Gln Gly Leu Tyr Leu Thr Val Pro Gln Thr
                2325                2330                2335

Pro Leu Lys Lys Pro Gly Ser Thr Pro Ala Thr Pro Ala Pro Asp Asp
            2340                2345                2350

Ser Gly Asp Glu Pro Val Glx
        2355


<210> SEQ ID NO 27
<211> LENGTH: 5735
<212> TYPE: DNA
<213> ORGANISM: Rattus

<400> SEQUENCE: 27

ccggcttcgg cgccgtgccc ggccacgtcc atgccaaggg ctccctgctc cacgctgaca      60

tggctgacag caacttaccg ccctcatctg cagcagcccc ggcccccgag ccgggaatca     120

ctgagcagcc ggggccccgg agtccccctc catcccctcc aggcctggag gagccattgg     180

aaggaaccaa ccctgacgtc ccacatccag acctggctcc tgttgctttc ttctgcctgc     240

gccagaccac gagcccacgg aactggtgca tcaagatggt ttgtaacccg tggttcgagt     300

gtgtgagcat gctggttatt ctgctgaact gtgtgaccct gggcatgtac cagccatgtg     360

atgacatgga gtgcctgtcg gaccgttgca agatcctgca ggtcttcgat gacttcatct     420

tcatcttctt tgccatggag atggtgctta agatggtggc cctgggcatt tttggcaaga     480

agtgctacct cggagacaca tggaaccgcc tggatttctt cattgtcatg gcagggatgg     540

ttgagtactc tctggaccta cagaacatca acctgtcagc catccgcact gtgcgtgtcc     600

tgaggcctct caaagccatc aaccgtgtac ccagcctgcg gatcctggtg aacctgctgc     660

tcgacacgct gcccatgctg gggaacgtgc tcctgctctg tttcttcgtc ttcttcatct     720

tcggcatcat tggcgtgcag ctctgggcag gcctgctacg gaaccgctgc ttcctggaag     780

aaaacttcac catacaaggg gatgtggccc tgccccctta ttaccaacca gaggaggatg     840

acgagatgcc ctttatctgc tccctgactg gggacaatgg catcatgggc tgccacgaga     900

tccccccact gaaggagcag ggccgggaag tctgcctgtc caaagatgat gtgtatgact     960

tcggggcggg gcgccaggac ctcaacgcca gcggtctgtg cgtcaactgg aaccgctact    1020

acaacgtctg ccgcacgggc aacgccaacc ctcacaaggg cgccatcaac tttgacaaca    1080

ttggctatgc ctggattgtg attttccagg tgatcactct ggaaggctgg gtggagatca    1140

tgtactatgt gatggacgca cattctttct acaacttcat tctgctcatc atagtgggct    1200

ccttcttcat gatcaacttg tgcctcgttc tcatagcaac ccagttctct gagaccaagc    1260

aacggaacca ccggctgatg ctggagcaac gccagcgcta cctgtcctcc agcacggtgg    1320

ccagttacgc tgagcccggt gattgctatg aggagatctt ccaatatgtc tgtcacatcc    1380

ttcgcaaagc caagcgccgt gccctaggcc tctaccaggc cctgcagaac cggcgccagg    1440

ccatgggccc ggggacacca gcccctgcca agcctgggcc ccatgccaag gagcccagcc    1500
```

-continued

```
actcgaagct gtgcccacga cacagccccc tggaccccac tccccacaca ctggtgcagc   1560
ccatctctgc cattctggcc tcttacccca gcagctgccc tcactgccag cacgaggcag   1620
gcaggcggcc ctctggcctg ggcagcactg actcaggcca ggaaggctca ggttctggtg   1680
gctctgcaga ggccgaagcc aatggggatg gactccagag cagagaggat ggggtctcct   1740
cggacctggg gaaggaggag gaacaggagg acggggcagc ccgactgtgt ggggatgtat   1800
ggcgcgagac acgaaaaaag ctgcggggca tcgtggacag caagtacttc aacagaggta   1860
tcatgatggc tatcctggtg aacacagtca gcatgggcat cgagcaccac gaacagcccg   1920
aggagctgac caacatcctg gagatctgca atgtggtctt caccagtatg tttgccctgg   1980
agatgatcct gaaactggcc gcctttgggc tcttcgacta cctgcggaac ccttacaaca   2040
tctttgacag catcatcgtc atcatcagca tctgggaaat cgtggggcag gcggacagtg   2100
gcctgtctgt gctgcgcact tcccggttgc tgcgggtgct gaagctagtg cgcttcatgc   2160
cggcgctgcg ccagctcgtg gtgctcatga agaccatgga caacgtggcc accttctgca   2220
tgctactcat gctgttcatc ttcatcttca gcatccttgg gatcgatatc tttggctgca   2280
aattcagcct ccgcacggac acgggagaca ccgttcctga caggaagaac ttcgattcct   2340
tactgtgggc catcgtcaca gtgttccaga tcctcactca ggaggactgg aacgttgtcc   2400
tgtacaatgg catggcctcc accacccccct gggcctccct ctattttgtt gccctcatga   2460
cctttggcaa ctacgttctc ttcaatctcc tggtggctat cctggtagag ggtttccagg   2520
ctgagggtga tgctaatcgt tcctactctg atgaggacca gagctcatcc aatttagagg   2580
agttagacaa gctcccagag ggcctggaca acaggagaga tctcaagctc tgcccaatac   2640
ccatgacacc caatggacac ctggacccta gcctccctct gggtgcgcat ctgggtcctg   2700
ctggtaccat gggtactgcc ccccgcctct cactgcagcc agacccggta ctggtggccc   2760
gggactctcg gaaaagcagt tactggtccc tgggcaggat gagctatgat cagcgatcct   2820
tgtccagctc ccggagctcc tactacggcc ctgggggccg cagtgggacc tgggctagcc   2880
gccgctccag ctggaacagc ctgaaacaca agccgccctc agctgagcat gagtccttac   2940
tgtctgggga gggtggaggt agctgcgtca gggcctgtga aggcgcccgg gaggaggcgc   3000
caactcgcac cgcacccctg catgctccac accggcacca cgcgcaccat ggaccccacc   3060
tggcacaccg tcaccgacac caccgccgga ctctgtccct cgataccagg gactctgttg   3120
acctgggaga gctggtgccc gtggtgggtg cccactcacg ggccgcttgg agggggggcgg   3180
gtcaggcccc tgggcacgag gactgcaatg gcagaatgcc caacatggcc aaggatgtct   3240
tcaccaagat ggatgaccgc cgcgaccgcg gggaggacga ggaggagatc gactataccc   3300
tgtgtttccg ggtccgcaag atgatttgct gtgtgtacaa gccggactgg tgcgaagtcc   3360
gcgaggactg gtcggtctac ctcttctccc ccgagaacaa gttccggatc ctgtgtcaga   3420
ctatcattgc tcacaagctt tttgactacg tggtcttggc ctttatcttc ctcaactgta   3480
tcaccattgc tctggagaga ccccagattg aagctggtag cactgagcgc atcttcctca   3540
cggtgtctaa ctacatcttc acagccatct tcgtgggcga gatgacactg aaggtggttt   3600
ctctgggcct gtactttggt gagcaggcgt acctgcgtac ggactggaat gtactggatg   3660
gtttcctggt ctttgtgtcc atcatcgata tcgtagtgtc cgtggcctct gctgggggag   3720
ccaagattct gggggtcctg cggctcctgc gtaccttacg tcctttgaga gttatcagcc   3780
gggcccctgg gctgaagctg gtggtagaga cgctcatctc ctccctcaag cccattggga   3840
acatcgtcct catctgctgt gccttcttca tcatcttcgg catcctgggg gtgcagcttt   3900
```

-continued

```
tcaaaggcaa gttctaccat tgtttgggag tggacacccg aaacatcacc aaccgatctg   3960
actgcgtggc ggccaactac cgctgggtgc atcacaaata caactttgac aacctgggcc   4020
aggcattgat gtccctcttt gtcttggcct ccaaggacgg ctgggtgaac atcatgtata   4080
atggattaga tgctgttgct gtggaccagc agcccgtgac gaaccacaac ccctggatgc   4140
tactgtactt catttcgttc ctgctcatcg tcagcttctt tgtgctcaac atgtttgtgg   4200
gcgtggtcgt ggagaacttc cacaagtgcc ggcagcacca ggaggctgag gaggcgcgga   4260
ggcgtgagga gaaacggctg cggcgcctgg aaaagaagcg ccgttacgct cagaggctgc   4320
cctactatgc tacctactgt cccacaaggc tgctcatcca ctccatgtgc accagccact   4380
acctggacat cttcattacc ttcatcatct gcctcaatgt tgtcaccatg tccctggagc   4440
actacaacca gcctacatcc ctagagacag cccttaagta ctgcaactac atgttcacca   4500
ctgtgtttgt gctggaggct gtgctgaagc tggtggcatt tggcctgagg cgtttcttca   4560
aggaccgatg gaaccagctg gacctggcca ttgtgctgct gtccgtcatg ggcatcacac   4620
tggaggagat cgagatcaat gccgcccttc ccatcaaccc caccatcatc cgtatcatgc   4680
gtgttctgcg tatcgcccgg gtgttgaagc tattgaagat ggccacagga atgcgggccc   4740
tgctggacac agtggtacag gctctgcccc aggtgggcaa cctgggcctg ctcttcatgc   4800
tgctcttctt catctatgct gctctgggag tggagctctt cggaaagctg gtctgcaatg   4860
acgagaaccc gtgtgagggt atgagccggc acgccacctt tgaaaactct gctagggcct   4920
tcctcacgct cttccaggtc tccacaggcg ataactggaa tggaattatg aaggacaccc   4980
tgcgagactg tacccatgat gagcgcacgt gcctaagcag cctgcagttt gtgtcaccgc   5040
tctactttgt gagcttcgtg ctcacagctc agttcgtgct catcaacgtg gtggtggccg   5100
tgctgatgaa acatctggat gacagcaaca aggaggccca ggaggatgca gagatggatg   5160
ctgagatcga gctggagatg gcccatggct ccggcccctg ccctggcccc tgccctggtc   5220
cctgcccctg cccctgcccc tgcccctgtt ctggcccgag gtgcccacta gttacctggg   5280
gctcgggggc gatggatcgg gaggggcagg tgctggaggc acaccgagag tcacctgtgc   5340
gcactgctat caggtgctgg acaccgagag tcacctgtgc cggcactgct attctccagc   5400
ccaggagacc ctgtggctgg acagggtctc tttaatcatc aaggactcct tggaggggga   5460
gctgaccatc attgacaacc tgtctgggtc cgtcttccac cactacgcct cactgacggc   5520
tgtggcaagt gtcaccatga caagcaagag gtgcagctgg ctgagacaga ggccttctcc   5580
ctgaactcag acaggtcttc atccatcctg ctgggggatg acctgagtct tgaggacccc   5640
acggcctcgc acagggcccc aaaggagagc aagggtgaac aataaagagc ctccggagcc   5700
catgcaggct ggagacctgg atgaatgcaa aaaaa                              5735
```

```
<210> SEQ ID NO 28
<211> LENGTH: 1792
<212> TYPE: PRT
<213> ORGANISM: Rattus

<400> SEQUENCE: 28

Met Ala Asp Ser Asn Leu Pro Pro Ser Ser Ala Ala Ala Pro Ala Pro
 1               5                  10                  15

Glu Pro Gly Ile Thr Glu Gln Pro Gly Pro Arg Ser Pro Pro Pro Ser
            20                  25                  30

Pro Pro Gly Leu Glu Glu Pro Leu Glu Gly Thr Asn Pro Asp Val Pro
        35                  40                  45
```

-continued

```
His Pro Asp Leu Ala Pro Val Ala Phe Phe Cys Leu Arg Gln Thr Thr
    50                  55                  60

Ser Pro Arg Asn Trp Cys Ile Lys Met Val Cys Asn Pro Trp Phe Glu
65                  70                  75                  80

Cys Val Ser Met Leu Val Ile Leu Leu Asn Cys Val Thr Leu Gly Met
                85                  90                  95

Tyr Gln Pro Cys Asp Asp Met Glu Cys Leu Ser Asp Arg Cys Lys Ile
            100                 105                 110

Leu Gln Val Phe Asp Asp Phe Ile Phe Ile Phe Phe Ala Met Glu Met
        115                 120                 125

Val Leu Lys Met Val Ala Leu Gly Ile Phe Gly Lys Lys Cys Tyr Leu
    130                 135                 140

Gly Asp Thr Trp Asn Arg Leu Asp Phe Phe Ile Val Met Ala Gly Met
145                 150                 155                 160

Val Glu Tyr Ser Leu Asp Leu Gln Asn Ile Asn Leu Ser Ala Ile Arg
                165                 170                 175

Thr Val Arg Val Leu Arg Pro Leu Lys Ala Ile Asn Arg Val Pro Ser
            180                 185                 190

Leu Arg Ile Leu Val Asn Leu Leu Leu Asp Thr Leu Pro Met Leu Gly
        195                 200                 205

Asn Val Leu Leu Leu Cys Phe Phe Val Phe Phe Ile Phe Gly Ile Ile
    210                 215                 220

Gly Val Gln Leu Trp Ala Gly Leu Leu Arg Asn Arg Cys Phe Leu Glu
225                 230                 235                 240

Glu Asn Phe Thr Ile Gln Gly Asp Val Ala Leu Pro Pro Tyr Tyr Gln
                245                 250                 255

Pro Glu Glu Asp Asp Glu Met Pro Phe Ile Cys Ser Leu Thr Gly Asp
            260                 265                 270

Asn Gly Ile Met Gly Cys His Glu Ile Pro Pro Leu Lys Glu Gln Gly
        275                 280                 285

Arg Glu Val Cys Leu Ser Lys Asp Asp Val Tyr Asp Phe Gly Ala Gly
    290                 295                 300

Arg Gln Asp Leu Asn Ala Ser Gly Leu Cys Val Asn Trp Asn Arg Tyr
305                 310                 315                 320

Tyr Asn Val Cys Arg Thr Gly Asn Ala Asn Pro His Lys Gly Ala Ile
                325                 330                 335

Asn Phe Asp Asn Ile Gly Tyr Ala Trp Ile Val Ile Phe Gln Val Ile
            340                 345                 350

Thr Leu Glu Gly Trp Val Glu Ile Met Tyr Tyr Val Met Asp Ala His
        355                 360                 365

Ser Phe Tyr Asn Phe Ile Leu Leu Ile Ile Val Gly Ser Phe Phe Met
    370                 375                 380

Ile Asn Leu Cys Leu Val Leu Ile Ala Thr Gln Phe Ser Glu Thr Lys
385                 390                 395                 400

Gln Arg Asn His Arg Leu Met Leu Glu Gln Arg Gln Arg Tyr Leu Ser
                405                 410                 415

Ser Ser Thr Val Ala Ser Tyr Ala Glu Pro Gly Asp Cys Tyr Glu Glu
            420                 425                 430

Ile Phe Gln Tyr Val Cys His Ile Leu Arg Lys Ala Lys Arg Arg Ala
        435                 440                 445

Leu Gly Leu Tyr Gln Ala Leu Gln Asn Arg Arg Gln Ala Met Gly Pro
    450                 455                 460
```

-continued

```
Gly Thr Pro Ala Pro Ala Lys Pro Gly Pro His Ala Lys Glu Pro Ser
465                 470                 475                 480

His Ser Lys Leu Cys Pro Arg His Ser Pro Leu Asp Pro Thr Pro His
                485                 490                 495

Thr Leu Val Gln Pro Ile Ser Ala Ile Leu Ala Ser Tyr Pro Ser Ser
            500                 505                 510

Cys Pro His Cys Gln His Glu Ala Gly Arg Arg Pro Ser Gly Leu Gly
        515                 520                 525

Ser Thr Asp Ser Gly Gln Glu Gly Ser Gly Ser Gly Gly Ser Ala Glu
    530                 535                 540

Ala Glu Ala Asn Gly Asp Gly Leu Gln Ser Arg Glu Asp Gly Val Ser
545                 550                 555                 560

Ser Asp Leu Gly Lys Glu Glu Glu Gln Glu Asp Gly Ala Ala Arg Leu
                565                 570                 575

Cys Gly Asp Val Trp Arg Glu Thr Arg Lys Lys Leu Arg Gly Ile Val
            580                 585                 590

Asp Ser Lys Tyr Phe Asn Arg Gly Ile Met Met Ala Ile Leu Val Asn
        595                 600                 605

Thr Val Ser Met Gly Ile Glu His His Glu Gln Pro Glu Glu Leu Thr
    610                 615                 620

Asn Ile Leu Glu Ile Cys Asn Val Val Phe Thr Ser Met Phe Ala Leu
625                 630                 635                 640

Glu Met Ile Leu Lys Leu Ala Ala Phe Gly Leu Phe Asp Tyr Leu Arg
                645                 650                 655

Asn Pro Tyr Asn Ile Phe Asp Ser Ile Ile Val Ile Ile Ser Ile Trp
            660                 665                 670

Glu Ile Val Gly Gln Ala Asp Ser Gly Leu Ser Val Leu Arg Thr Ser
        675                 680                 685

Arg Leu Leu Arg Val Leu Lys Leu Val Arg Phe Met Pro Ala Leu Arg
    690                 695                 700

Gln Leu Val Val Leu Met Lys Thr Met Asp Asn Val Ala Thr Phe Cys
705                 710                 715                 720

Met Leu Leu Met Leu Phe Ile Phe Ile Phe Ser Ile Leu Gly Ile Asp
                725                 730                 735

Ile Phe Gly Cys Lys Phe Ser Leu Arg Thr Asp Thr Gly Asp Thr Val
            740                 745                 750

Pro Asp Arg Lys Asn Phe Asp Ser Leu Leu Trp Ala Ile Val Thr Val
        755                 760                 765

Phe Gln Ile Leu Thr Gln Glu Asp Trp Asn Val Val Leu Tyr Asn Gly
    770                 775                 780

Met Ala Ser Thr Thr Pro Trp Ala Ser Leu Tyr Phe Val Ala Leu Met
785                 790                 795                 800

Thr Phe Gly Asn Tyr Val Leu Phe Asn Leu Leu Val Ala Ile Leu Val
                805                 810                 815

Glu Gly Phe Gln Ala Glu Gly Asp Ala Asn Arg Ser Tyr Ser Asp Glu
            820                 825                 830

Asp Gln Ser Ser Ser Asn Leu Glu Glu Leu Asp Lys Leu Pro Glu Gly
        835                 840                 845

Leu Asp Asn Arg Arg Asp Leu Lys Leu Cys Pro Ile Pro Met Thr Pro
    850                 855                 860

Asn Gly His Leu Asp Pro Ser Leu Pro Leu Gly Ala His Leu Gly Pro
865                 870                 875                 880

Ala Gly Thr Met Gly Thr Ala Pro Arg Leu Ser Leu Gln Pro Asp Pro
```

-continued

```
                885                 890                 895

Val Leu Val Ala Arg Asp Ser Arg Lys Ser Ser Tyr Trp Ser Leu Gly
            900                 905                 910

Arg Met Ser Tyr Asp Gln Arg Ser Leu Ser Ser Ser Arg Ser Ser Tyr
        915                 920                 925

Tyr Gly Pro Gly Gly Arg Ser Gly Thr Trp Ala Ser Arg Arg Ser Ser
    930                 935                 940

Trp Asn Ser Leu Lys His Lys Pro Pro Ser Ala Glu His Glu Ser Leu
945                 950                 955                 960

Leu Ser Gly Glu Gly Gly Gly Ser Cys Val Arg Ala Cys Glu Gly Ala
                965                 970                 975

Arg Glu Glu Ala Pro Thr Arg Thr Ala Pro Leu His Ala Pro His Arg
            980                 985                 990

His His Ala His His Gly Pro His Leu Ala His Arg His Arg His His
        995                 1000                1005

Arg Arg Thr Leu Ser Leu Asp Thr Arg Asp Ser Val Asp Leu Gly Glu
    1010                1015                1020

Leu Val Pro Val Val Gly Ala His Ser Arg Ala Ala Trp Arg Gly Ala
1025                1030                1035                1040

Gly Gln Ala Pro Gly His Glu Asp Cys Asn Gly Arg Met Pro Asn Met
                1045                1050                1055

Ala Lys Asp Val Phe Thr Lys Met Asp Asp Arg Arg Asp Arg Gly Glu
            1060                1065                1070

Asp Glu Glu Glu Ile Asp Tyr Thr Leu Cys Phe Arg Val Arg Lys Met
        1075                1080                1085

Ile Cys Cys Val Tyr Lys Pro Asp Trp Cys Glu Val Arg Glu Asp Trp
    1090                1095                1100

Ser Val Tyr Leu Phe Ser Pro Glu Asn Lys Phe Arg Ile Leu Cys Gln
1105                1110                1115                1120

Thr Ile Ile Ala His Lys Leu Phe Asp Tyr Val Val Leu Ala Phe Ile
                1125                1130                1135

Phe Leu Asn Cys Ile Thr Ile Ala Leu Glu Arg Pro Gln Ile Glu Ala
            1140                1145                1150

Gly Ser Thr Glu Arg Ile Phe Leu Thr Val Ser Asn Tyr Ile Phe Thr
        1155                1160                1165

Ala Ile Phe Val Gly Glu Met Thr Leu Lys Val Val Ser Leu Gly Leu
    1170                1175                1180

Tyr Phe Gly Glu Gln Ala Tyr Leu Arg Thr Asp Trp Asn Val Leu Asp
1185                1190                1195                1200

Gly Phe Leu Val Phe Val Ser Ile Ile Asp Ile Val Val Ser Val Ala
                1205                1210                1215

Ser Ala Gly Gly Ala Lys Ile Leu Gly Val Leu Arg Leu Leu Arg Thr
            1220                1225                1230

Leu Arg Pro Leu Arg Val Ile Ser Arg Ala Pro Gly Leu Lys Leu Val
        1235                1240                1245

Val Glu Thr Leu Ile Ser Ser Leu Lys Pro Ile Gly Asn Ile Val Leu
    1250                1255                1260

Ile Cys Cys Ala Phe Phe Ile Ile Phe Gly Ile Leu Gly Val Gln Leu
1265                1270                1275                1280

Phe Lys Gly Lys Phe Tyr His Cys Leu Gly Val Asp Thr Arg Asn Ile
                1285                1290                1295

Thr Asn Arg Ser Asp Cys Val Ala Ala Asn Tyr Arg Trp Val His His
            1300                1305                1310
```

-continued

```
Lys Tyr Asn Phe Asp Asn Leu Gly Gln Ala Leu Met Ser Leu Phe Val
        1315                1320                1325

Leu Ala Ser Lys Asp Gly Trp Val Asn Ile Met Tyr Asn Gly Leu Asp
    1330                1335                1340

Ala Val Ala Val Asp Gln Gln Pro Val Thr Asn His Asn Pro Trp Met
1345                1350                1355                1360

Leu Leu Tyr Phe Ile Ser Phe Leu Leu Ile Val Ser Phe Phe Val Leu
                1365                1370                1375

Asn Met Phe Val Gly Val Val Val Glu Asn Phe His Lys Cys Arg Gln
            1380                1385                1390

His Gln Glu Ala Glu Glu Ala Arg Arg Arg Glu Glu Lys Arg Leu Arg
        1395                1400                1405

Arg Leu Glu Lys Lys Arg Arg Tyr Ala Gln Arg Leu Pro Tyr Tyr Ala
    1410                1415                1420

Thr Tyr Cys Pro Thr Arg Leu Leu Ile His Ser Met Cys Thr Ser His
1425                1430                1435                1440

Tyr Leu Asp Ile Phe Ile Thr Phe Ile Ile Cys Leu Asn Val Val Thr
                1445                1450                1455

Met Ser Leu Glu His Tyr Asn Gln Pro Thr Ser Leu Glu Thr Ala Leu
            1460                1465                1470

Lys Tyr Cys Asn Tyr Met Phe Thr Thr Val Phe Val Leu Glu Ala Val
        1475                1480                1485

Leu Lys Leu Val Ala Phe Gly Leu Arg Arg Phe Phe Lys Asp Arg Trp
    1490                1495                1500

Asn Gln Leu Asp Leu Ala Ile Val Leu Leu Ser Val Met Gly Ile Thr
1505                1510                1515                1520

Leu Glu Glu Ile Glu Ile Asn Ala Ala Leu Pro Ile Asn Pro Thr Ile
                1525                1530                1535

Ile Arg Ile Met Arg Val Leu Arg Ile Ala Arg Val Leu Lys Leu Leu
            1540                1545                1550

Lys Met Ala Thr Gly Met Arg Ala Leu Leu Asp Thr Val Val Gln Ala
        1555                1560                1565

Leu Pro Gln Val Gly Asn Leu Gly Leu Leu Phe Met Leu Leu Phe Phe
    1570                1575                1580

Ile Tyr Ala Ala Leu Gly Val Glu Leu Phe Gly Lys Leu Val Cys Asn
1585                1590                1595                1600

Asp Glu Asn Pro Cys Glu Gly Met Ser Arg His Ala Thr Phe Glu Asn
                1605                1610                1615

Ser Ala Arg Ala Phe Leu Thr Leu Phe Gln Val Ser Thr Gly Asp Asn
            1620                1625                1630

Trp Asn Gly Ile Met Lys Asp Thr Leu Arg Asp Cys Thr His Asp Glu
        1635                1640                1645

Arg Thr Cys Leu Ser Ser Leu Gln Phe Val Ser Pro Leu Tyr Phe Val
    1650                1655                1660

Ser Phe Val Leu Thr Ala Gln Phe Val Leu Ile Asn Val Val Val Ala
1665                1670                1675                1680

Val Leu Met Lys His Leu Asp Asp Ser Asn Lys Glu Ala Gln Glu Asp
                1685                1690                1695

Ala Glu Met Asp Ala Glu Ile Glu Leu Glu Met Ala His Gly Ser Gly
            1700                1705                1710

Pro Cys Pro Gly Pro Cys Pro Gly Pro Cys Pro Cys Pro Cys Pro Cys
        1715                1720                1725
```

-continued

```
Pro Cys Ser Gly Pro Arg Cys Pro Leu Val Thr Trp Gly Ser Gly Ala
    1730                1735                1740

Met Asp Arg Glu Gly Gln Val Leu Glu Ala His Arg Glu Ser Pro Val
1745                1750                1755                1760

Arg Thr Ala Ile Arg Cys Trp Thr Pro Arg Val Thr Cys Ala Gly Thr
                1765                1770                1775

Ala Ile Leu Gln Pro Arg Arg Pro Cys Gly Trp Thr Gly Ser Leu Glx
            1780                1785                1790


<210> SEQ ID NO 29
<211> LENGTH: 540
<212> TYPE: DNA
<213> ORGANISM: Rattus

<400> SEQUENCE: 29

aagcttctct gagccaggca gctgctatga ggagctactc aagtacctgg tgtacatcct      60

ccgaaaagca gcccgaaggc tggcccaggt ctctagggct ataggcgtgc gggctgggct     120

gctcagcagc ccagtggccc gtagtgggca ggagccccag cccagtggca gctgcactcg     180

ctcacaccgt cgtctgtctg tccaccacct ggtccaccac catcaccacc accatcacca     240

ctaccacctg ggtaatggga cgctcagagt tccccgggcc agcccagaga tccaggacag     300

ggatgccaat gggtctcgcc ggctcatgct accaccaccc tctacaccca ctccctctgg     360

gggccctccg aggggtgcgg agtctgtaca cagcttctac catgctgact gccacttgga     420

gccagtccgt tgccaggcac cccctcccag atgcccatcg gaggcatctg gtaggactgt     480

gggtagtggg aaggtgtacc ccactgtgca taccagccct ccaccagaga tactgaagga     540


<210> SEQ ID NO 30
<211> LENGTH: 2212
<212> TYPE: DNA
<213> ORGANISM: Homo sapiens

<400> SEQUENCE: 30

gtgaggggga gccggccggc tggcccggga agccccaggg gcgcagggga agcgggactc      60

gcgccgggcg gggtttccct gcgccccggc gccccgcggg cagcatgccc ctgcgggcag     120

ggggagctgg gctgaactgg ccctcccggg ggctcagctt gcgccctaga gcccaccaga     180

tgtgcccccg ccggggcccc cgggttgcgt gaggacacct cctctgaggg gcgccgcttg     240

cccctctccg gatcgcccgg ggccccggct ggccagagga tggacgagga ggaggatgga     300

gcgggcgccg aggagtcggg acagccccgg agcttcatgc ggctcaacga cctgtcgggg     360

gccgggggcc ggccggggcc ggggtcagca gaaaaggacc cgggcagcgc ggactccgag     420

gcggaggggc tgccgtaccc ggcgctggcc ccggtggttt tcttctactt gagccaggac     480

agccgcccgc ggagctggtg tctccgcacg gtctgtaacc cctggtttga gcgcatcagc     540

atgttggtca tccttctcaa ctgcgtgacc ctgggcatgt tccggccatg cgaggacatc     600

gcctgtgact cccagcgctg ccggatcctg caggcctttg atgacttcat ctttgccttc     660

tttgccgtgg agatggtggt gaagatggtg gccttgggca tctttgggaa aaagtgttac     720

ctgggagaca cttggaaccg gcttgacttt ttcatcgtca tcgcagggat gctggagtac     780

tcgctggacc tgcagaacgt cagcttctca gctgtcagga cagtccgtgt gctgcgaccg     840

ctcagggcca ttaaccgggt gcccagcatg cgcatccttg tcacgttgct gctggatacg     900

ctgcccatgc tgggcaacgt cctgctgctc tgcttcttcg tcttcttcat cttcggcatc     960

gtcggcgtcc agctgtgggc agggctgctt cggaaccgat gcttcctacc tgagaatttc    1020
```

-continued

```
agcctccccc tgagcgtgga cctggagcgc tattaccaga cagagaacga ggatgagagc   1080

cccttcatct gctcccagcc acgcgagaac ggcatgcggt cctgcagaag cgtgcccacg   1140

ctgcgcgggg acgggggcgg tggcccacct tgcggtctgg actatgaggc ctacaacagc   1200

tccagcaaca ccacctgtgt caactggaac cagtactaca ccaactgctc agcgggggag   1260

cacaacccct tcaagggcgc catcaacttt gacaacattg gctatgcctg gatcgccatc   1320

ttccaggtca tcacgctgga gggctgggtc gacatcatgt actttgtgat ggatgctcat   1380

tccttctaca atttcatcta cttcatcctc ctcatcatcg tgggctcctt cttcatgatc   1440

aacctgtgcc tggtggtgat tgccacgcag ttctcagaga ccaagcagcg ggaaagccag   1500

ctgatgcggg agcagcgtgt gcggttcctg tccaacgcca gcaccctggc tagcttctct   1560

gagcccggca gctgctatga ggagctgctc aagtacctgg tgtacatcct tcgtaaggca   1620

gcccgcaggc tggctcaggt ctctcgggca gcaggtgtgc gggttgggct gctcagcagc   1680

ccagcacccc tcgggggcca ggagacccag cccagcagca gctgctctcg ctcccaccgc   1740

cgcctatccg tccaccacct ggtgcaccac caccaccacc atcaccacca ctaccacctg   1800

ggcaatggga cgctcagggc cccccgggcc agcccggaga tccaggacag ggatgccaat   1860

gggtcccgcc ggctcatgct gccaccaccc tcgacgcctg ccctctccgg ggcccccct   1920

ggtggcgcag agtctgtgca cagcttctac catgccgact gccacttaga gccagtccgc   1980

tgccaggcgc cccctcccag gtccccatct gaggcatccg gcaggactgt gggcagcggg   2040

aaggtgtatc ccaccgtgca caccagccct ccaccggaga cgctgaagga gaaggcacta   2100

gtagaggtgg ctgccagctc tggccccca accctcacca gcctcaacat cccacccggg   2160

ccctacagct ccatgcacaa gctgctggag acacagagta caggtgcctg cc           2212
```

```
<210> SEQ ID NO 31
<211> LENGTH: 644
<212> TYPE: PRT
<213> ORGANISM: Homo sapiens

<400> SEQUENCE: 31

Met Asp Glu Glu Glu Asp Gly Ala Gly Ala Glu Glu Ser Gly Gln Pro
 1               5                  10                  15

Arg Ser Phe Met Arg Leu Asn Asp Leu Ser Gly Ala Gly Gly Arg Pro
            20                  25                  30

Gly Pro Gly Ser Ala Glu Lys Asp Pro Gly Ser Ala Asp Ser Glu Ala
        35                  40                  45

Glu Gly Leu Pro Tyr Pro Ala Leu Ala Pro Val Val Phe Phe Tyr Leu
    50                  55                  60

Ser Gln Asp Ser Arg Pro Arg Ser Trp Cys Leu Arg Thr Val Cys Asn
65                  70                  75                  80

Pro Trp Phe Glu Arg Ile Ser Met Leu Val Ile Leu Leu Asn Cys Val
                85                  90                  95

Thr Leu Gly Met Phe Arg Pro Cys Glu Asp Ile Ala Cys Asp Ser Gln
            100                 105                 110

Arg Cys Arg Ile Leu Gln Ala Phe Asp Asp Phe Ile Phe Ala Phe Phe
        115                 120                 125

Ala Val Glu Met Val Val Lys Met Val Ala Leu Gly Ile Phe Gly Lys
    130                 135                 140

Lys Cys Tyr Leu Gly Asp Thr Trp Asn Arg Leu Asp Phe Phe Ile Val
145                 150                 155                 160
```

-continued

```
Ile Ala Gly Met Leu Glu Tyr Ser Leu Asp Leu Gln Asn Val Ser Phe
                165                 170                 175

Ser Ala Val Arg Thr Val Arg Val Leu Arg Pro Leu Arg Ala Ile Asn
            180                 185                 190

Arg Val Pro Ser Met Arg Ile Leu Val Thr Leu Leu Leu Asp Thr Leu
        195                 200                 205

Pro Met Leu Gly Asn Val Leu Leu Leu Cys Phe Phe Val Phe Phe Ile
    210                 215                 220

Phe Gly Ile Val Gly Val Gln Leu Trp Ala Gly Leu Leu Arg Asn Arg
225                 230                 235                 240

Cys Phe Leu Pro Glu Asn Phe Ser Leu Pro Leu Ser Val Asp Leu Glu
                245                 250                 255

Arg Tyr Tyr Gln Thr Glu Asn Glu Asp Glu Ser Pro Phe Ile Cys Ser
            260                 265                 270

Gln Pro Arg Glu Asn Gly Met Arg Ser Cys Arg Ser Val Pro Thr Leu
        275                 280                 285

Arg Gly Asp Gly Gly Gly Gly Pro Pro Cys Gly Leu Asp Tyr Glu Ala
    290                 295                 300

Tyr Asn Ser Ser Ser Asn Thr Thr Cys Val Asn Trp Asn Gln Tyr Tyr
305                 310                 315                 320

Thr Asn Cys Ser Ala Gly Glu His Asn Pro Phe Lys Gly Ala Ile Asn
                325                 330                 335

Phe Asp Asn Ile Gly Tyr Ala Trp Ile Ala Ile Phe Gln Val Ile Thr
            340                 345                 350

Leu Glu Gly Trp Val Asp Ile Met Tyr Phe Val Met Asp Ala His Ser
        355                 360                 365

Phe Tyr Asn Phe Ile Tyr Phe Ile Leu Leu Ile Ile Val Gly Ser Phe
    370                 375                 380

Phe Met Ile Asn Leu Cys Leu Val Val Ile Ala Thr Gln Phe Ser Glu
385                 390                 395                 400

Thr Lys Gln Arg Glu Ser Gln Leu Met Arg Glu Gln Arg Val Arg Phe
                405                 410                 415

Leu Ser Asn Ala Ser Thr Leu Ala Ser Phe Ser Glu Pro Gly Ser Cys
            420                 425                 430

Tyr Glu Glu Leu Leu Lys Tyr Leu Val Tyr Ile Leu Arg Lys Ala Ala
        435                 440                 445

Arg Arg Leu Ala Gln Val Ser Arg Ala Ala Gly Val Arg Val Gly Leu
    450                 455                 460

Leu Ser Ser Pro Ala Pro Leu Gly Gly Gln Glu Thr Gln Pro Ser Ser
465                 470                 475                 480

Ser Cys Ser Arg Ser His Arg Arg Leu Ser Val His His Leu Val His
                485                 490                 495

His His His His His His His His Tyr His Leu Gly Asn Gly Thr Leu
            500                 505                 510

Arg Ala Pro Arg Ala Ser Pro Glu Ile Gln Asp Arg Asp Ala Asn Gly
        515                 520                 525

Ser Arg Arg Leu Met Leu Pro Pro Pro Ser Thr Pro Ala Leu Ser Gly
    530                 535                 540

Ala Pro Pro Gly Gly Ala Glu Ser Val His Ser Phe Tyr His Ala Asp
545                 550                 555                 560

Cys His Leu Glu Pro Val Arg Cys Gln Ala Pro Pro Pro Arg Ser Pro
                565                 570                 575

Ser Glu Ala Ser Gly Arg Thr Val Gly Ser Gly Lys Val Tyr Pro Thr
```

-continued

```
            580                 585                 590

Val His Thr Ser Pro Pro Pro Glu Thr Leu Lys Glu Lys Ala Leu Val
        595                 600                 605

Glu Val Ala Ala Ser Ser Gly Pro Pro Thr Leu Thr Ser Leu Asn Ile
    610                 615                 620

Pro Pro Gly Pro Tyr Ser Ser Met His Lys Leu Leu Glu Thr Gln Ser
625                 630                 635                 640

Thr Gly Ala Cys


<210> SEQ ID NO 32
<211> LENGTH: 1608
<212> TYPE: DNA
<213> ORGANISM: Homo sapiens

<400> SEQUENCE: 32

atgcccgcgg ggacgccgcc ggccagcaga gcgaggtgct gccggccgcc accatgaccg      60

agggcgcacg ggccgccgac gaggtccggg tgcccctggg cgcgccgccc cctggccctg     120

cggcgttggt gggggcgtcc ccggagagcc ccggggcgcc gggacgcgag gcggagcggg     180

ggtccgagct cggcgtgtca ccctccgaga gcccggcggc cgagcgcggc gcggagctgg     240

gtgccgacga ggagcagcgc gtcccgtacc cggccttggc ggccacggtc ttcttctgcc     300

tcggtcagac cacgcggccg cgcagctggt gcctccggct ggtctgcaac ccatggttcg     360

agcacgtgag catgctggta atcatgctca actgcgtgac cctgggcatg ttccggccct     420

gtgaggacgt tgagtgcggc tccgagcgct gcaacatcct ggaggccttt gacgccttca     480

ttttcgcctt ttttgcggtg gagatggtca tcaagatggt ggccttgggg ctgttcgggc     540

agaagtgtta cctgggtgac acgtggaaca ggctggattt cttcatcgtc gtggcgggca     600

tgatggagta ctcgttggac ggacacaacg tgagcctctc ggctatcagg accgtgcggg     660

tgctgcggcc cctccgcgcc atcaaccgcg tgcctagcat gcggatcctg gtcactctgc     720

tgctggatac gctgcccatg ctcgggaacg tccttctgct gtgcttcttc gtcttcttca     780

ttttcggcat cgttggcgtc cagctctggg ctggcctcct gcggaaccgc tgcttcctgg     840

acagtgcctt tgtcaggaac aacaacctga ccttcctgcg gccgtactac cagacggagg     900

agggcgagga gaacccgttc atctgctcct cacgccgaga caacggcatg cagaagtgct     960

cgcacatccc cggccgccgc gagctgcgca tgccctgcac cctgggctgg gaggcctaca    1020

cgcagccgca ggccgagggg gtgggcgctg cacgcaacgc ctgcatcaac tggaaccagt    1080

actacaacgt gtgccgctcg ggtgactcca acccccacaa cggtgccatc aacttcgaca    1140

acatcggcta cgcctggatc gccatcttcc aggtgatcac gctggaaggc tgggtggaca    1200

tcatgtacta cgtcatggac gcccactcat tctacaactt catctatttc atcctgctca    1260

tcatcgtggg ctccttcttc atgatcaacc tgtgcctggt ggtgattgcc acgcagttct    1320

cggagacgaa gcagcgggag agtcagctga tgcgggagca gcgggcacgc cacctgtcca    1380

acgacagcac gctggccagc ttctccgagc ctggcagctg ctacgaagag ctgctgaagt    1440

acgtgggcca catattccgc aaggtcaagc ggcgcagctt gcgcctctac gcccgctggc    1500

agagccgctg gcgcaagaag gtggaccccca gtgctgtgca aggccagggt cccgggcacc    1560

gccagcgccg ggcaggcagg cacacagcct cggtgcacca cctggtct                 1608


<210> SEQ ID NO 33
<211> LENGTH: 518
<212> TYPE: PRT
```

<213> ORGANISM: Homo sapiens

<400> SEQUENCE: 33

```
Met Thr Glu Gly Ala Arg Ala Ala Asp Glu Val Arg Val Pro Leu Gly
 1               5                  10                  15

Ala Pro Pro Pro Gly Pro Ala Ala Leu Val Gly Ala Ser Pro Glu Ser
            20                  25                  30

Pro Gly Ala Pro Gly Arg Glu Ala Glu Arg Gly Ser Glu Leu Gly Val
        35                  40                  45

Ser Pro Ser Glu Ser Pro Ala Ala Glu Arg Gly Ala Glu Leu Gly Ala
    50                  55                  60

Asp Glu Glu Gln Arg Val Pro Tyr Pro Ala Leu Ala Ala Thr Val Phe
65                  70                  75                  80

Phe Cys Leu Gly Gln Thr Thr Arg Pro Arg Ser Trp Cys Leu Arg Leu
                85                  90                  95

Val Cys Asn Pro Trp Phe Glu His Val Ser Met Leu Val Ile Met Leu
            100                 105                 110

Asn Cys Val Thr Leu Gly Met Phe Arg Pro Cys Glu Asp Val Glu Cys
        115                 120                 125

Gly Ser Glu Arg Cys Asn Ile Leu Glu Ala Phe Asp Ala Phe Ile Phe
    130                 135                 140

Ala Phe Phe Ala Val Glu Met Val Ile Lys Met Val Ala Leu Gly Leu
145                 150                 155                 160

Phe Gly Gln Lys Cys Tyr Leu Gly Asp Thr Trp Asn Arg Leu Asp Phe
                165                 170                 175

Phe Ile Val Val Ala Gly Met Met Glu Tyr Ser Leu Asp Gly His Asn
            180                 185                 190

Val Ser Leu Ser Ala Ile Arg Thr Val Arg Val Leu Arg Pro Leu Arg
        195                 200                 205

Ala Ile Asn Arg Val Pro Ser Met Arg Ile Leu Val Thr Leu Leu Leu
    210                 215                 220

Asp Thr Leu Pro Met Leu Gly Asn Val Leu Leu Leu Cys Phe Phe Val
225                 230                 235                 240

Phe Phe Ile Phe Gly Ile Val Gly Val Gln Leu Trp Ala Gly Leu Leu
                245                 250                 255

Arg Asn Arg Cys Phe Leu Asp Ser Ala Phe Val Arg Asn Asn Asn Leu
            260                 265                 270

Thr Phe Leu Arg Pro Tyr Tyr Gln Thr Glu Glu Gly Glu Glu Asn Pro
        275                 280                 285

Phe Ile Cys Ser Ser Arg Arg Asp Asn Gly Met Gln Lys Cys Ser His
    290                 295                 300

Ile Pro Gly Arg Arg Glu Leu Arg Met Pro Cys Thr Leu Gly Trp Glu
305                 310                 315                 320

Ala Tyr Thr Gln Pro Gln Ala Glu Gly Val Gly Ala Ala Arg Asn Ala
                325                 330                 335

Cys Ile Asn Trp Asn Gln Tyr Tyr Asn Val Cys Arg Ser Gly Asp Ser
            340                 345                 350

Asn Pro His Asn Gly Ala Ile Asn Phe Asp Asn Ile Gly Tyr Ala Trp
        355                 360                 365

Ile Ala Ile Phe Gln Val Ile Thr Leu Glu Gly Trp Val Asp Ile Met
    370                 375                 380

Tyr Tyr Val Met Asp Ala His Ser Phe Tyr Asn Phe Ile Tyr Phe Ile
385                 390                 395                 400
```

-continued

```
Leu Leu Ile Ile Val Gly Ser Phe Phe Met Ile Asn Leu Cys Leu Val
                405                 410                 415

Val Ile Ala Thr Gln Phe Ser Glu Thr Lys Gln Arg Glu Ser Gln Leu
            420                 425                 430

Met Arg Glu Gln Arg Ala Arg His Leu Ser Asn Asp Ser Thr Leu Ala
        435                 440                 445

Ser Phe Ser Glu Pro Gly Ser Cys Tyr Glu Glu Leu Leu Lys Tyr Val
    450                 455                 460

Gly His Ile Phe Arg Lys Val Lys Arg Arg Ser Leu Arg Leu Tyr Ala
465                 470                 475                 480

Arg Trp Gln Ser Arg Trp Arg Lys Lys Val Asp Pro Ser Ala Val Gln
                485                 490                 495

Gly Gln Gly Pro Gly His Arg Gln Arg Arg Ala Gly Arg His Thr Ala
            500                 505                 510

Ser Val His His Leu Val
        515
```

<210> SEQ ID NO 34
<211> LENGTH: 1080
<212> TYPE: DNA
<213> ORGANISM: Homo sapiens

<400> SEQUENCE: 34

```
gcagtgtcat gtctctaggg aggatgagct atgaccagcg ctccctgtcc agctcccgga     60

gctcctacta cgggccatgg ggccgcagcg cggcctgggc cagccgtcgc tccagctgga    120

acagcctcaa gcacaagccg ccgtcggcgg agcatgagtc cctgctctct gcggagcgcg    180

gcggcggcgc ccgggtctgc gaggttgccg cggacgaggg gccgccgcgg gccgcacccc    240

tgcacacccc acacgcccac cacattcatc acgggcccca tctggcgcac cgccaccgcc    300

accaccgccg gacgctgtcc ctcgacaaca gggactcggt ggacctggcc gagctggtgc    360

ccgcggtggg cgcccacccc cgggccgcct ggagggcggc aggcccggcc cccgggcatg    420

aggactgcaa tggcaggatg cccagcatcg ccaaagacgt cttcaccaag atgggcgacc    480

gcggggatcg cggggaggat gaggaggaaa tcgactacac cctgtgcttc cgcgtccgca    540

agatgatcga cgtctataag cccgactggt gcgaggtccg cgaagactgg tctgtctacc    600

tcttctctcc cgagaacagg ttccgggtcc tgtgtcagac cattattgcc cacaaactct    660

tcgactacgt cgtcctggcc ttcatctttc tcaactgcat caccatcgcc ctggagcggc    720

ctcagatcga ggccggcagc accgaacgca tctttctcac cgtgtccaac tacatcttca    780

cggccatctt cgtgggcgag atgacattga aggtagtctc gctgggcctg tacttcggcg    840

agcaggcgta cctacgcagc agctggaacg tgctggatgg ctttcttgtc ttcgtgtcca    900

tcatcgacat cgtggtgtcc ctggcctcag ccgggggagc caagatcttg gggtcctcc    960

gagtcttgcg gctcctgcgc accctacgcc ccctgcgtgt catcagccgg gcgccgggcc   1020

tgaagctggt ggtggagaca ctcatctcct ccctcaagcc catcggcaac atcgtgctca   1080
```

<210> SEQ ID NO 35
<211> LENGTH: 359
<212> TYPE: PRT
<213> ORGANISM: Homo sapiens

<400> SEQUENCE: 35

```
Ser Val Met Ser Leu Gly Arg Met Ser Tyr Asp Gln Arg Ser Leu Ser
 1               5                  10                  15
```

-continued

```
Ser Ser Arg Ser Ser Tyr Tyr Gly Pro Trp Gly Arg Ser Ala Ala Trp
            20                  25                  30

Ala Ser Arg Arg Ser Ser Trp Asn Ser Leu Lys His Lys Pro Pro Ser
        35                  40                  45

Ala Glu His Glu Ser Leu Leu Ser Ala Glu Arg Gly Gly Gly Ala Arg
    50                  55                  60

Val Cys Glu Val Ala Ala Asp Glu Gly Pro Pro Arg Ala Ala Pro Leu
65                  70                  75                  80

His Thr Pro His Ala His His Ile His His Gly Pro His Leu Ala His
                85                  90                  95

Arg His Arg His His Arg Arg Thr Leu Ser Leu Asp Asn Arg Asp Ser
            100                 105                 110

Val Asp Leu Ala Glu Leu Val Pro Ala Val Gly Ala His Pro Arg Ala
        115                 120                 125

Ala Trp Arg Ala Ala Gly Pro Ala Pro Gly His Glu Asp Cys Asn Gly
    130                 135                 140

Arg Met Pro Ser Ile Ala Lys Asp Val Phe Thr Lys Met Gly Asp Arg
145                 150                 155                 160

Gly Asp Arg Gly Glu Asp Glu Glu Glu Ile Asp Tyr Thr Leu Cys Phe
                165                 170                 175

Arg Val Arg Lys Met Ile Asp Val Tyr Lys Pro Asp Trp Cys Glu Val
            180                 185                 190

Arg Glu Asp Trp Ser Val Tyr Leu Phe Ser Pro Glu Asn Arg Phe Arg
        195                 200                 205

Val Leu Cys Gln Thr Ile Ile Ala His Lys Leu Phe Asp Tyr Val Val
    210                 215                 220

Leu Ala Phe Ile Phe Leu Asn Cys Ile Thr Ile Ala Leu Glu Arg Pro
225                 230                 235                 240

Gln Ile Glu Ala Gly Ser Thr Glu Arg Ile Phe Leu Thr Val Ser Asn
                245                 250                 255

Tyr Ile Phe Thr Ala Ile Phe Val Gly Glu Met Thr Leu Lys Val Val
            260                 265                 270

Ser Leu Gly Leu Tyr Phe Gly Glu Gln Ala Tyr Leu Arg Ser Ser Trp
        275                 280                 285

Asn Val Leu Asp Gly Phe Leu Val Phe Val Ser Ile Ile Asp Ile Val
    290                 295                 300

Val Ser Leu Ala Ser Ala Gly Gly Ala Lys Ile Leu Gly Val Leu Arg
305                 310                 315                 320

Val Leu Arg Leu Leu Arg Thr Leu Arg Pro Leu Arg Val Ile Ser Arg
                325                 330                 335

Ala Pro Gly Leu Lys Leu Val Val Glu Thr Leu Ile Ser Ser Leu Lys
            340                 345                 350

Pro Ile Gly Asn Ile Val Leu
        355
```

<210> SEQ ID NO 36
<211> LENGTH: 6892
<212> TYPE: DNA
<213> ORGANISM: Homo sapiens

<400> SEQUENCE: 36

```
aagcttgctt gcccctctcc ggatcgcccg gggccccggc tggccagagg atggacgagg     60

aggaggatgg agcgggcgcc gaggagtcgg gacagccccg gagcttcatg cggctcaacg    120

acctgtcggg ggccgggggc cggccggggc cggggtcagc agaaaaggac ccgggcagcg    180
```

-continued

```
cggactccga ggcggagggg ctgccgtacc cggcgctggc cccggtggtt ttcttctact    240
tgagccagga cagccgcccg cggagctggt gtctccgcac ggtctgtaac ccctggtttg    300
agcgcatcag catgttggtc atccttctca actgcgtgac cctgggcatg ttccggccat    360
gcgaggacat cgcctgtgac tcccagcgct gccggatcct gcaggccttt gatgacttca    420
tctttgcctt ctttgccgtg gagatggtgg tgaagatggt ggccttgggc atctttggga    480
aaaagtgtta cctgggagac acttggaacc ggcttgactt tttcatcgtc atcgcaggga    540
tgctggagta ctcgctggac ctgcagaacg tcagcttctc agctgtcagg acagtccgtg    600
tgctgcgacc gctcagggcc attaaccggg tgcccagcat gcgcatcctt gtcacgttgc    660
tgctggatac gctgcccatg ctgggcaacg tcctgctgct ctgcttcttc gtcttcttca    720
tcttcggcat cgtcggcgtc cagctgtggg cagggctgct tcggaaccga tgcttcctac    780
ctgagaattt cagcctcccc ctgagcgtgg acctggagcg ctattaccag acagagaacg    840
aggatgagag ccccttcatc tgctcccagc cacgcgagaa cggcatgcgg tcctgcagaa    900
gcgtgcccac gctgcgcggg gacgggggcg gtggcccacc ttgcggtctg gactatgagg    960
cctacaacag ctccagcaac accacctgtg tcaactggaa ccagtactac accaactgct   1020
cagcggggga gcacaacccc ttcaagggcg ccatcaactt tgacaacatt ggctatgcct   1080
ggatcgccat cttccaggtc atcacgctgg agggctgggt cgacatcatg tactttgtga   1140
tggatgctca ttccttctac aatttcatct acttcatcct cctcatcatc gtgggctcct   1200
tcttcatgat caacctgtgc ctggtggtga ttgccacgca gttctcagag accaagcagc   1260
gggaaagcca gctgatgcgg gagcagcgtg tgcggttcct gtccaacgcc agcaccctgg   1320
ctagcttctc tgagcccggc agctgctatg aggagctgct caagtacctg gtgtacatcc   1380
ttcgtaaggc agcccgcagg ctggctcagg tctctcgggc agcaggtgtg cgggttgggc   1440
tgctcagcag cccagcaccc ctcgggggcc aggagaccca gcccagcagc agctgctctc   1500
gctcccaccg ccgcctatcc gtccaccacc tggtgcacca ccaccaccac catcaccacc   1560
actaccacct gggcaatggg acgctcaggg ccccccgggc cagcccggag atccaggaca   1620
gggatgccaa tgggtcccgc aggctcatgc tgccaccacc ctcgacgcct gccctctccg   1680
gggccccccc tggtggcgca gagtctgtgc acagcttcta ccatgccgac tgccacttag   1740
agccagtccg ctgccaggcg ccccctccca ggtccccatc tgaggcatcc ggcaggactg   1800
tgggcagcgg gaaggtgtat cccaccgtgc acaccagccc tccaccggag acgctgaagg   1860
agaaggcact agtagaggtg gctgccagct ctgggccccc aaccctcacc agcctcaaca   1920
tcccacccgg gccctacagc tccatgcaca agctgctgga gacacagagt acaggtgcct   1980
gccaaagctc ttgcaagatc tccagccctt gcttgaaagc agacagtgga gcctgtggtc   2040
cagacagctg cccctactgt gcccgggccg gggcagggga ggtggagctc gccgaccgtg   2100
aaatgcctga ctcagacagc gaggcagttt atgagttcac acaggatgcc cagcacagcg   2160
acctccggga cccccacagc cggcggcaac ggagcctggg cccagatgca gagcccagct   2220
ctgtgctggc cttctggagg ctaatctgtg acaccttccg aaagattgtg gacagcaagt   2280
actttggccg gggaatcatg atcgccatcc tggtcaacac actcagcatg ggcatcgaat   2340
accacgagca gcccgaggag cttaccaacg ccctagaaat cagcaacatc gtcttcacca   2400
gcctctttgc cctggagatg ctgctgaagc tgcttgtgta tggtcccttt ggctacatca   2460
agaatcccta caacatcttc gatggtgtca ttgtggtcat cagcgtgtgg gagatcgtgg   2520
```

-continued

```
gccagcaggg gggcggcctg tcggtgctgc ggaccttccg cctgatgcgt gtgctgaagc   2580
tggtgcgctt cctgccggcg ctgcagcggc agctggtggt gctcatgaag accatggaca   2640
acgtggccac cttctgcatg ctgcttatgc tcttcatctt catcttcagc atcctgggca   2700
tgcatctctt cggctgcaag tttgcctctg agcgggatgg ggacaccctg ccagaccgga   2760
agaattttga ctccttgctc tgggccatcg tcactgtctt tcagatcctg acccaggagg   2820
actggaacaa agtcctctac aatggtatgg cctccacgtc gtcctgggcg gccctttatt   2880
tcattgccct catgaccttc ggcaactacg tgctcttcaa tttgctggtc gccattctgg   2940
tggagggctt ccaggcggag gaaatcagca aacgggaaga tgcgagtgga cagttaagct   3000
gtattcagct gcctgtcgac tcccaggggg gagatgccaa caagtccgaa tcagagcccg   3060
atttcttctc acccagcctg gatggtgatg gggacaggaa gaagtgcttg gccttggtgt   3120
ccctgggaga gcacccggag ctgcggaaga gcctgctgcc gcctctcatc atccacacgg   3180
ccgccacacc catgtcgctg cccaagagca ccagcacggg cctgggcgag gcgctgggcc   3240
ctgcgtcgcg ccgcaccagc agcagcgggt cggcagagcc tggggcggcc cacgagatga   3300
agtcaccgcc cagcgcccgc agctctccgc acagcccctg gagcgctgca agcagctgga   3360
ccagcaggcg ctccagccgg aacagcctcg gccgtgcacc cagcctgaag cggagaagcc   3420
caagtggaga gcggcggtcc ctgttgtcgg gagaaggcca ggagagccag gatgaagagg   3480
agagctcaga agaggagcgg gccagccctg cgggcagtga ccatcgccac agggggtccc   3540
tggagcggga ggccaagagt tcctttgacc tgccagacac actgcaggtg ccagggctgc   3600
atcgcactgc cagtggccga gggtctgctt ctgagcacca ggactgcaat ggcaagtcgg   3660
cttcagggcg cctggcccgg gccctgcggc ctgatgaccc ccactggat ggggatgacg    3720
ccgatgacga gggcaacctg agcaaagggg aacgggtccg cgcgtggatc cgagcccgac   3780
tccctgcctg ctacctcgag cgagactcct ggtcagccta catcttccct cctcagtcca   3840
ggttccgcct cctgtgtcac cggatcatca cccacaagat gttcgaccac gtggtccttg   3900
tcatcatctt ccttaactgc atcaccatcg ccatggagcg ccccaaaatt gacccccaca   3960
gcgctgaacg catcttcctg accctctcca attacatctt caccgcagtc tttctggctg   4020
aaatgacagt gaaggtggtg gcactgggct ggtgcttcgg ggagcaggcg tacctgcgga   4080
gcagttggaa cgtgctggac gggctgttgg tgctcatctc cgtcatcgac attctggtgt   4140
ccatggtctc tgacagcggc accaagatcc tgggcatgct gagggtgctg cggctgctgc   4200
ggaccctgcg cccgctcagg gtgatcagcc gggcgcaggg gctgaagctg gtggtggaga   4260
cgctgatgtc ctcactgaaa cccatcggca acattgtagt catctgctgt gccttcttca   4320
tcattttcgg catcttgggg gtgcagctct tcaaagggaa gtttttcgtg tgccagggcg   4380
aggataccag gaacatcacc aataaatcgg actgtgccga ggccagttac cggtgggtcc   4440
ggcacaagta caactttgac aaccttggcc aggccctgat gtccctgttc gttttggcct   4500
ccaaggatgg ttgggtggac atcatgtacg atgggctgga tgctgtgggc gtggaccagc   4560
agcccatcat gaaccacaac ccctggatgc tgctgtactt catctcgttc ctgctcattg   4620
tggccttctt tgtcctgaac atgtttgtgg gtgtggtggt ggagaacttc cacaagtgta   4680
ggcagcacca ggaggaagag gaggcccggc ggcgggagga gaagcgccta cgaagactgg   4740
agaaaaagag aaggaaagcc cagtgcaaac cttactactc cgactactcc cgcttccggc   4800
tcctcgtcca ccacttgtgc accagccact acctggacct cttcatcaca ggtgtcatcg   4860
ggctgaacgt ggtcaccatg gccatggagc actaccagca gccccagatt ctggatgagg   4920
```

-continued

```
ctctgaagat ctgcaactac atcttcactg tcatctttgt cttggagtca gttttcaaac   4980

ttgtggcctt tggtttccgt cggttcttcc aggacaggtg gaaccagctg gacctggcca   5040

ttgtgctgct gtccatcatg ggcatcacgc tggaggaaat cgaggtcaac gcctcgctgc   5100

ccatcaaccc caccatcatc cgcatcatga gggtgctgcg cattgcccga gtgctgaagc   5160

tgctgaagat ggctgtgggc atgcgggcgc tgctggacac ggtgatgcag gccctgcccc   5220

aggtggggaa cctgggactt ctcttcatgt tgttgttttt catctttgca gctctgggcg   5280

tggagctctt tggagacctg gagtgtgacg agacacaccc ctgtgagggc ctgggccgtc   5340

atgccacctt tcggaacttt ggcatggcct tcctaaccct cttccgagtc tccacaggtg   5400

acaattggaa tggcattatg aaggacaccc tccgggactg tgaccaggag tccacctgct   5460

acaacacggt catctcgcct atctactttg tgtccttcgt gctgacggcc cagttcgtgc   5520

tagtcaacgt ggtgatcgcc gtgctgatga agcacctgga ggagagcaac aaggaggcca   5580

aggaggaggc cgagctagag gctgagctgg agctggagat gaagaccctc agcccccagc   5640

cccactcgcc actgggcagc cccttcctct ggcctggggt cgagggcccc gacagccccg   5700

acagccccaa gcctggggct ctgcacccag cggcccacgc gagatcagcc tcccactttt   5760

ccctggagca ccccacgatg cagccccacc ccacggagct gccaggacca gacttactga   5820

ctgtgcggaa gtctggggtc agccgaacgc actctctgcc caatgacagc tacatgtgtc   5880

ggcatgggag cactgccgag gggcccctgg gacacagggg ctgggggctc cccaaagctc   5940

agtcaggctc cgtcttgtcc gttcactccc agccagcaga taccagctac atcctgcagc   6000

ttcccaaaga tgcacctcat ctgctccagc cccacagcgc ccccaacctgg ggcaccatcc   6060

ccaaactgcc cccaccagga cgctcccctt tggctcagag gccactcagg cgccaggcag   6120

caataaggac tgactccttg gacgttcagg gtctgggcag ccgggaagac ctgctggcag   6180

aggtgagtgg gccctccccg cccctggccc gggcctactc tttctggggc cagtcaagta   6240

cccaggcaca gcagcactcc cgcagccaca gcaagatctc caagcacatg accccgccag   6300

ccccttgccc aggcccagaa cccaactggg gcaagggccc tccagagacc agaagcagct   6360

tagagttgga cacggagctg agctggattt caggagacct cctgcccccct ggcggccagg   6420

aggagccccc atccccacgg gacctgaaga agtgctacag cgtggaggcc cagagctgcc   6480

agcgccggcc tacgtcctgg ctggatgagc agaggagaca ctctatcgcc gtcagctgcc   6540

tggacagcgg ctcccaaccc cacctgggca cagacccctc taaccttggg ggccagcctc   6600

ttggggggcc tgggagccgg cccaagaaaa aactcagccc gcctagtatc accatagacc   6660

cccccgagag ccaaggtcct cggaccccgc ccagccctgg tatctgcctc cggaggaggg   6720

ctccgtccag cgactccaag gatcccttgg cctctggccc ccctgacagc atggctgcct   6780

cgccctcccc aaagaaagat gtgctgagtc tctccggttt atcctctgac ccagcagacc   6840

tggacccctg agtcctgccc cactttccca ctcacctttc tccactgggt gc           6892
```

<210> SEQ ID NO 37
<211> LENGTH: 2266
<212> TYPE: PRT
<213> ORGANISM: Homo sapiens

<400> SEQUENCE: 37

```
Met Asp Glu Glu Glu Asp Gly Ala Gly Ala Glu Glu Ser Gly Gln Pro
 1               5                  10                  15

Arg Ser Phe Met Arg Leu Asn Asp Leu Ser Gly Ala Gly Gly Arg Pro
```

-continued

```
                20                  25                  30

Gly Pro Gly Ser Ala Glu Lys Asp Pro Gly Ser Ala Asp Ser Glu Ala
            35                  40                  45

Glu Gly Leu Pro Tyr Pro Ala Leu Ala Pro Val Val Phe Phe Tyr Leu
    50                  55                  60

Ser Gln Asp Ser Arg Pro Arg Ser Trp Cys Leu Arg Thr Val Cys Asn
65                  70                  75                  80

Pro Trp Phe Glu Arg Ile Ser Met Leu Val Ile Leu Leu Asn Cys Val
                85                  90                  95

Thr Leu Gly Met Phe Arg Pro Cys Glu Asp Ile Ala Cys Asp Ser Gln
            100                 105                 110

Arg Cys Arg Ile Leu Gln Ala Phe Asp Asp Phe Ile Phe Ala Phe Phe
        115                 120                 125

Ala Val Glu Met Val Val Lys Met Val Ala Leu Gly Ile Phe Gly Lys
    130                 135                 140

Lys Cys Tyr Leu Gly Asp Thr Trp Asn Arg Leu Asp Phe Phe Ile Val
145                 150                 155                 160

Ile Ala Gly Met Leu Glu Tyr Ser Leu Asp Leu Gln Asn Val Ser Phe
                165                 170                 175

Ser Ala Val Arg Thr Val Arg Val Leu Arg Pro Leu Arg Ala Ile Asn
            180                 185                 190

Arg Val Pro Ser Met Arg Ile Leu Val Thr Leu Leu Leu Asp Thr Leu
        195                 200                 205

Pro Met Leu Gly Asn Val Leu Leu Leu Cys Phe Phe Val Phe Phe Ile
    210                 215                 220

Phe Gly Ile Val Gly Val Gln Leu Trp Ala Gly Leu Leu Arg Asn Arg
225                 230                 235                 240

Cys Phe Leu Pro Glu Asn Phe Ser Leu Pro Leu Ser Val Asp Leu Glu
                245                 250                 255

Arg Tyr Tyr Gln Thr Glu Asn Glu Asp Glu Ser Pro Phe Ile Cys Ser
            260                 265                 270

Gln Pro Arg Glu Asn Gly Met Arg Ser Cys Arg Ser Val Pro Thr Leu
        275                 280                 285

Arg Gly Asp Gly Gly Gly Gly Pro Pro Cys Gly Leu Asp Tyr Glu Ala
    290                 295                 300

Tyr Asn Ser Ser Ser Asn Thr Thr Cys Val Asn Trp Asn Gln Tyr Tyr
305                 310                 315                 320

Thr Asn Cys Ser Ala Gly Glu His Asn Pro Phe Lys Gly Ala Ile Asn
                325                 330                 335

Phe Asp Asn Ile Gly Tyr Ala Trp Ile Ala Ile Phe Gln Val Ile Thr
            340                 345                 350

Leu Glu Gly Trp Val Asp Ile Met Tyr Phe Val Met Asp Ala His Ser
        355                 360                 365

Phe Tyr Asn Phe Ile Tyr Phe Ile Leu Leu Ile Ile Val Gly Ser Phe
    370                 375                 380

Phe Met Ile Asn Leu Cys Leu Val Val Ile Ala Thr Gln Phe Ser Glu
385                 390                 395                 400

Thr Lys Gln Arg Glu Ser Gln Leu Met Arg Glu Gln Arg Val Arg Phe
                405                 410                 415

Leu Ser Asn Ala Ser Thr Leu Ala Ser Phe Ser Glu Pro Gly Ser Cys
            420                 425                 430

Tyr Glu Glu Leu Leu Lys Tyr Leu Val Tyr Ile Leu Arg Lys Ala Ala
        435                 440                 445
```

-continued

```
Arg Arg Leu Ala Gln Val Ser Arg Ala Ala Gly Val Arg Val Gly Leu
    450                 455                 460

Leu Ser Ser Pro Ala Pro Leu Gly Gly Gln Glu Thr Gln Pro Ser Ser
465                 470                 475                 480

Ser Cys Ser Arg Ser His Arg Arg Leu Ser Val His His Leu Val His
                485                 490                 495

His His His His His His His His Tyr His Leu Gly Asn Gly Thr Leu
            500                 505                 510

Arg Ala Pro Arg Ala Ser Pro Glu Ile Gln Asp Arg Asp Ala Asn Gly
        515                 520                 525

Ser Arg Arg Leu Met Leu Pro Pro Pro Ser Thr Pro Ala Leu Ser Gly
    530                 535                 540

Ala Pro Pro Gly Gly Ala Glu Ser Val His Ser Phe Tyr His Ala Asp
545                 550                 555                 560

Cys His Leu Glu Pro Val Arg Cys Gln Ala Pro Pro Pro Arg Ser Pro
                565                 570                 575

Ser Glu Ala Ser Gly Arg Thr Val Gly Ser Gly Lys Val Tyr Pro Thr
            580                 585                 590

Val His Thr Ser Pro Pro Pro Glu Thr Leu Lys Glu Lys Ala Leu Val
        595                 600                 605

Glu Val Ala Ala Ser Ser Gly Pro Pro Thr Leu Thr Ser Leu Asn Ile
    610                 615                 620

Pro Pro Gly Pro Tyr Ser Ser Met His Lys Leu Leu Glu Thr Gln Ser
625                 630                 635                 640

Thr Gly Ala Cys Gln Ser Ser Cys Lys Ile Ser Ser Pro Cys Leu Lys
                645                 650                 655

Ala Asp Ser Gly Ala Cys Gly Pro Asp Ser Cys Pro Tyr Cys Ala Arg
            660                 665                 670

Ala Gly Ala Gly Glu Val Glu Leu Ala Asp Arg Glu Met Pro Asp Ser
        675                 680                 685

Asp Ser Glu Ala Val Tyr Glu Phe Thr Gln Asp Ala Gln His Ser Asp
    690                 695                 700

Leu Arg Asp Pro His Ser Arg Arg Gln Arg Ser Leu Gly Pro Asp Ala
705                 710                 715                 720

Glu Pro Ser Ser Val Leu Ala Phe Trp Arg Leu Ile Cys Asp Thr Phe
                725                 730                 735

Arg Lys Ile Val Asp Ser Lys Tyr Phe Gly Arg Gly Ile Met Ile Ala
            740                 745                 750

Ile Leu Val Asn Thr Leu Ser Met Gly Ile Glu Tyr His Glu Gln Pro
        755                 760                 765

Glu Glu Leu Thr Asn Ala Leu Glu Ile Ser Asn Ile Val Phe Thr Ser
    770                 775                 780

Leu Phe Ala Leu Glu Met Leu Leu Lys Leu Leu Val Tyr Gly Pro Phe
785                 790                 795                 800

Gly Tyr Ile Lys Asn Pro Tyr Asn Ile Phe Asp Gly Val Ile Val Val
                805                 810                 815

Ile Ser Val Trp Glu Ile Val Gly Gln Gln Gly Gly Gly Leu Ser Val
            820                 825                 830

Leu Arg Thr Phe Arg Leu Met Arg Val Leu Lys Leu Val Arg Phe Leu
        835                 840                 845

Pro Ala Leu Gln Arg Gln Leu Val Val Leu Met Lys Thr Met Asp Asn
    850                 855                 860
```

-continued

Val Ala Thr Phe Cys Met Leu Leu Met Leu Phe Ile Phe Ile Phe Ser
865 870 875 880

Ile Leu Gly Met His Leu Phe Gly Cys Lys Phe Ala Ser Glu Arg Asp
885 890 895

Gly Asp Thr Leu Pro Asp Arg Lys Asn Phe Asp Ser Leu Leu Trp Ala
900 905 910

Ile Val Thr Val Phe Gln Ile Leu Thr Gln Glu Asp Trp Asn Lys Val
915 920 925

Leu Tyr Asn Gly Met Ala Ser Thr Ser Ser Trp Ala Ala Leu Tyr Phe
930 935 940

Ile Ala Leu Met Thr Phe Gly Asn Tyr Val Leu Phe Asn Leu Leu Val
945 950 955 960

Ala Ile Leu Val Glu Gly Phe Gln Ala Glu Glu Ile Ser Lys Arg Glu
965 970 975

Asp Ala Ser Gly Gln Leu Ser Cys Ile Gln Leu Pro Val Asp Ser Gln
980 985 990

Gly Gly Asp Ala Asn Lys Ser Glu Ser Glu Pro Asp Phe Phe Ser Pro
995 1000 1005

Ser Leu Asp Gly Asp Gly Asp Arg Lys Lys Cys Leu Ala Leu Val Ser
1010 1015 1020

Leu Gly Glu His Pro Glu Leu Arg Lys Ser Leu Leu Pro Pro Leu Ile
1025 1030 1035 1040

Ile His Thr Ala Ala Thr Pro Met Ser Leu Pro Lys Ser Thr Ser Thr
1045 1050 1055

Gly Leu Gly Glu Ala Leu Gly Pro Ala Ser Arg Arg Thr Ser Ser Ser
1060 1065 1070

Gly Ser Ala Glu Pro Gly Ala Ala His Glu Met Lys Ser Pro Pro Ser
1075 1080 1085

Ala Arg Ser Ser Pro His Ser Pro Trp Ser Ala Ala Ser Ser Trp Thr
1090 1095 1100

Ser Arg Arg Ser Ser Arg Asn Ser Leu Gly Arg Ala Pro Ser Leu Lys
1105 1110 1115 1120

Arg Arg Ser Pro Ser Gly Glu Arg Arg Ser Leu Leu Ser Gly Glu Gly
1125 1130 1135

Gln Glu Ser Gln Asp Glu Glu Glu Ser Ser Glu Glu Glu Arg Ala Ser
1140 1145 1150

Pro Ala Gly Ser Asp His Arg His Arg Gly Ser Leu Glu Arg Glu Ala
1155 1160 1165

Lys Ser Ser Phe Asp Leu Pro Asp Thr Leu Gln Val Pro Gly Leu His
1170 1175 1180

Arg Thr Ala Ser Gly Arg Gly Ser Ala Ser Glu His Gln Asp Cys Asn
1185 1190 1195 1200

Gly Lys Ser Ala Ser Gly Arg Leu Ala Arg Ala Leu Arg Pro Asp Asp
1205 1210 1215

Pro Pro Leu Asp Gly Asp Asp Ala Asp Asp Glu Gly Asn Leu Ser Lys
1220 1225 1230

Gly Glu Arg Val Arg Ala Trp Ile Arg Ala Arg Leu Pro Ala Cys Tyr
1235 1240 1245

Leu Glu Arg Asp Ser Trp Ser Ala Tyr Ile Phe Pro Pro Gln Ser Arg
1250 1255 1260

Phe Arg Leu Leu Cys His Arg Ile Ile Thr His Lys Met Phe Asp His
1265 1270 1275 1280

Val Val Leu Val Ile Ile Phe Leu Asn Cys Ile Thr Ile Ala Met Glu

-continued

```
            1285                1290                1295

Arg Pro Lys Ile Asp Pro His Ser Ala Glu Arg Ile Phe Leu Thr Leu
        1300                1305                1310

Ser Asn Tyr Ile Phe Thr Ala Val Phe Leu Ala Glu Met Thr Val Lys
    1315                1320                1325

Val Val Ala Leu Gly Trp Cys Phe Gly Glu Gln Ala Tyr Leu Arg Ser
1330                1335                1340

Ser Trp Asn Val Leu Asp Gly Leu Leu Val Leu Ile Ser Val Ile Asp
1345                1350                1355                1360

Ile Leu Val Ser Met Val Ser Asp Ser Gly Thr Lys Ile Leu Gly Met
            1365                1370                1375

Leu Arg Val Leu Arg Leu Leu Arg Thr Leu Arg Pro Leu Arg Val Ile
        1380                1385                1390

Ser Arg Ala Gln Gly Leu Lys Leu Val Val Glu Thr Leu Met Ser Ser
    1395                1400                1405

Leu Lys Pro Ile Gly Asn Ile Val Val Ile Cys Cys Ala Phe Phe Ile
1410                1415                1420

Ile Phe Gly Ile Leu Gly Val Gln Leu Phe Lys Gly Lys Phe Phe Val
1425                1430                1435                1440

Cys Gln Gly Glu Asp Thr Arg Asn Ile Thr Asn Lys Ser Asp Cys Ala
            1445                1450                1455

Glu Ala Ser Tyr Arg Trp Val Arg His Lys Tyr Asn Phe Asp Asn Leu
        1460                1465                1470

Gly Gln Ala Leu Met Ser Leu Phe Val Leu Ala Ser Lys Asp Gly Trp
    1475                1480                1485

Val Asp Ile Met Tyr Asp Gly Leu Asp Ala Val Gly Val Asp Gln Gln
1490                1495                1500

Pro Ile Met Asn His Asn Pro Trp Met Leu Leu Tyr Phe Ile Ser Phe
1505                1510                1515                1520

Leu Leu Ile Val Ala Phe Phe Val Leu Asn Met Phe Val Gly Val Val
            1525                1530                1535

Val Glu Asn Phe His Lys Cys Arg Gln His Gln Glu Glu Glu Glu Ala
        1540                1545                1550

Arg Arg Arg Glu Glu Lys Arg Leu Arg Arg Leu Glu Lys Lys Arg Arg
    1555                1560                1565

Lys Ala Gln Cys Lys Pro Tyr Tyr Ser Asp Tyr Ser Arg Phe Arg Leu
1570                1575                1580

Leu Val His His Leu Cys Thr Ser His Tyr Leu Asp Leu Phe Ile Thr
1585                1590                1595                1600

Gly Val Ile Gly Leu Asn Val Val Thr Met Ala Met Glu His Tyr Gln
            1605                1610                1615

Gln Pro Gln Ile Leu Asp Glu Ala Leu Lys Ile Cys Asn Tyr Ile Phe
        1620                1625                1630

Thr Val Ile Phe Val Leu Glu Ser Val Phe Lys Leu Val Ala Phe Gly
    1635                1640                1645

Phe Arg Arg Phe Phe Gln Asp Arg Trp Asn Gln Leu Asp Leu Ala Ile
1650                1655                1660

Val Leu Leu Ser Ile Met Gly Ile Thr Leu Glu Glu Ile Glu Val Asn
1665                1670                1675                1680

Ala Ser Leu Pro Ile Asn Pro Thr Ile Ile Arg Ile Met Arg Val Leu
            1685                1690                1695

Arg Ile Ala Arg Val Leu Lys Leu Leu Lys Met Ala Val Gly Met Arg
        1700                1705                1710
```

-continued

```
Ala Leu Leu Asp Thr Val Met Gln Ala Leu Pro Gln Val Gly Asn Leu
        1715                1720                1725

Gly Leu Leu Phe Met Leu Leu Phe Phe Ile Phe Ala Ala Leu Gly Val
    1730                1735                1740

Glu Leu Phe Gly Asp Leu Glu Cys Asp Glu Thr His Pro Cys Glu Gly
1745                1750                1755                1760

Leu Gly Arg His Ala Thr Phe Arg Asn Phe Gly Met Ala Phe Leu Thr
                1765                1770                1775

Leu Phe Arg Val Ser Thr Gly Asp Asn Trp Asn Gly Ile Met Lys Asp
            1780                1785                1790

Thr Leu Arg Asp Cys Asp Gln Glu Ser Thr Cys Tyr Asn Thr Val Ile
        1795                1800                1805

Ser Pro Ile Tyr Phe Val Ser Phe Val Leu Thr Ala Gln Phe Val Leu
    1810                1815                1820

Val Asn Val Val Ile Ala Val Leu Met Lys His Leu Glu Glu Ser Asn
1825                1830                1835                1840

Lys Glu Ala Lys Glu Glu Ala Glu Leu Glu Ala Glu Leu Glu Leu Glu
                1845                1850                1855

Met Lys Thr Leu Ser Pro Gln Pro His Ser Pro Leu Gly Ser Pro Phe
            1860                1865                1870

Leu Trp Pro Gly Val Glu Gly Pro Asp Ser Pro Asp Ser Pro Lys Pro
        1875                1880                1885

Gly Ala Leu His Pro Ala Ala His Ala Arg Ser Ala Ser His Phe Ser
    1890                1895                1900

Leu Glu His Pro Thr Met Gln Pro His Pro Thr Glu Leu Pro Gly Pro
1905                1910                1915                1920

Asp Leu Leu Thr Val Arg Lys Ser Gly Val Ser Arg Thr His Ser Leu
                1925                1930                1935

Pro Asn Asp Ser Tyr Met Cys Arg His Gly Ser Thr Ala Glu Gly Pro
            1940                1945                1950

Leu Gly His Arg Gly Trp Gly Leu Pro Lys Ala Gln Ser Gly Ser Val
        1955                1960                1965

Leu Ser Val His Ser Gln Pro Ala Asp Thr Ser Tyr Ile Leu Gln Leu
    1970                1975                1980

Pro Lys Asp Ala Pro His Leu Leu Gln Pro His Ser Ala Pro Thr Trp
1985                1990                1995                2000

Gly Thr Ile Pro Lys Leu Pro Pro Pro Gly Arg Ser Pro Leu Ala Gln
                2005                2010                2015

Arg Pro Leu Arg Arg Gln Ala Ala Ile Arg Thr Asp Ser Leu Asp Val
            2020                2025                2030

Gln Gly Leu Gly Ser Arg Glu Asp Leu Leu Ala Glu Val Ser Gly Pro
        2035                2040                2045

Ser Pro Pro Leu Ala Arg Ala Tyr Ser Phe Trp Gly Gln Ser Ser Thr
    2050                2055                2060

Gln Ala Gln Gln His Ser Arg Ser His Ser Lys Ile Ser Lys His Met
2065                2070                2075                2080

Thr Pro Pro Ala Pro Cys Pro Gly Pro Glu Pro Asn Trp Gly Lys Gly
                2085                2090                2095

Pro Pro Glu Thr Arg Ser Ser Leu Glu Leu Asp Thr Glu Leu Ser Trp
            2100                2105                2110

Ile Ser Gly Asp Leu Leu Pro Pro Gly Gly Gln Glu Glu Pro Pro Ser
        2115                2120                2125
```

-continued

```
Pro Arg Asp Leu Lys Lys Cys Tyr Ser Val Glu Ala Gln Ser Cys Gln
    2130                2135                2140

Arg Arg Pro Thr Ser Trp Leu Asp Glu Gln Arg Arg His Ser Ile Ala
2145                2150                2155                2160

Val Ser Cys Leu Asp Ser Gly Ser Gln Pro His Leu Gly Thr Asp Pro
                2165                2170                2175

Ser Asn Leu Gly Gly Gln Pro Leu Gly Gly Pro Gly Ser Arg Pro Lys
            2180                2185                2190

Lys Lys Leu Ser Pro Pro Ser Ile Thr Ile Asp Pro Pro Glu Ser Gln
        2195                2200                2205

Gly Pro Arg Thr Pro Pro Ser Pro Gly Ile Cys Leu Arg Arg Arg Ala
    2210                2215                2220

Pro Ser Ser Asp Ser Lys Asp Pro Leu Ala Ser Gly Pro Pro Asp Ser
2225                2230                2235                2240

Met Ala Ala Ser Pro Ser Pro Lys Lys Asp Val Leu Ser Leu Ser Gly
                2245                2250                2255

Leu Ser Ser Asp Pro Ala Asp Leu Asp Pro
            2260                2265


<210> SEQ ID NO 38
<211> LENGTH: 44
<212> TYPE: PRT
<213> ORGANISM: C. elegans

<400> SEQUENCE: 38

Leu Ala Ala Ser Glu Glu Gly Trp Val Tyr Val Gln Ile Ile Thr Gln
 1               5                  10                  15

Glu Gly Trp Thr Asp Phe Glu Thr Leu Ser Phe Lys Gly Trp Asn Val
            20                  25                  30

Ile Arg Cys Leu Thr Gly Glu Asp Trp Asn Asp Ile
        35                  40


<210> SEQ ID NO 39
<211> LENGTH: 44
<212> TYPE: PRT
<213> ORGANISM: C. elegans

<400> SEQUENCE: 39

Leu Ala Ala Ser Gln Glu Gly Trp Val Tyr Val Gln Ile Ile Thr Gln
 1               5                  10                  15

Glu Gly Trp Thr Asp Val Glu Thr Leu Ser Tyr Lys Gly Trp Asn Val
            20                  25                  30

Val Arg Ser Val Thr Gly Glu Asp Trp Asn Asp Ile
        35                  40


<210> SEQ ID NO 40
<211> LENGTH: 44
<212> TYPE: PRT
<213> ORGANISM: Rattus

<400> SEQUENCE: 40

Glu Ala Ser Ser Gln Glu Gly Trp Val Phe Leu Gln Ile Leu Thr Gln
 1               5                  10                  15

Glu Gly Trp Val Asp Val Glu Val Leu Ser Leu Lys Gly Trp Val Glu
            20                  25                  30

Val Arg Ile Val Thr Gly Glu Asp Trp Asn Lys Ile
        35                  40
```

-continued

<210> SEQ ID NO 41
<211> LENGTH: 44
<212> TYPE: PRT
<213> ORGANISM: Unknown
<220> FEATURE:
<223> OTHER INFORMATION: Mammalian L-Type Ca Channel

<400> SEQUENCE: 41

```
Gln Cys Ile Thr Met Glu Gly Trp Thr Asp Val Gln Ile Leu Thr Gly
 1               5                  10                  15

Glu Asp Trp Asn Ser Val Thr Val Ser Thr Phe Glu Gly Trp Pro Glu
            20                  25                  30

Leu Arg Cys Ala Thr Gly Glu Ala Trp Gln Asp Ile
        35                  40
```

<210> SEQ ID NO 42
<211> LENGTH: 44
<212> TYPE: PRT
<213> ORGANISM: Unknown
<220> FEATURE:
<223> OTHER INFORMATION: Mammalian T-Type Ca Channel

<400> SEQUENCE: 42

```
Gln Val Ile Thr Leu Glu Gly Trp Val Asp Ile Gln Ile Leu Thr Gln
 1               5                  10                  15

Glu Asp Trp Asn Lys Val Val Leu Ala Ser Lys Asp Gly Trp Val Asp
            20                  25                  30

Ile Arg Val Ser Thr Gly Asp Asn Trp Asn Gly Ile
        35                  40
```

<210> SEQ ID NO 43
<211> LENGTH: 44
<212> TYPE: PRT
<213> ORGANISM: Unknown
<220> FEATURE:
<223> OTHER INFORMATION: Mammalian Na Channels

<400> SEQUENCE: 43

```
Arg Leu Met Thr Gln Asp Phe Trp Glu Asn Leu Arg Val Leu Cys Gly
 1               5                  10                  15

Glu Trp Ile Glu Thr Met Gln Val Ala Thr Phe Lys Gly Trp Met Asp
            20                  25                  30

Ile Gln Ile Thr Thr Ser Ala Gly Trp Asp Gly Leu
        35                  40
```

<210> SEQ ID NO 44
<211> LENGTH: 9
<212> TYPE: PRT
<213> ORGANISM: Unknown
<220> FEATURE:
<223> OTHER INFORMATION: Consensus motif

<400> SEQUENCE: 44

```
Gln Gln Glu Leu Gly Tyr Trp Ile Glu
 1               5
```

<210> SEQ ID NO 45
<211> LENGTH: 4
<212> TYPE: PRT
<213> ORGANISM: Unknown
<220> FEATURE:
<223> OTHER INFORMATION: T-type channels in P-regions of domains I-IV

<400> SEQUENCE: 45

-continued

```
Glu Glu Asp Asp
 1


<210> SEQ ID NO 46
<211> LENGTH: 4
<212> TYPE: PRT
<213> ORGANISM: Unknown
<220> FEATURE:
<223> OTHER INFORMATION: Na channels in the P-region of domains I-IV

<400> SEQUENCE: 46

Asp Glu Lys Ala
 1


<210> SEQ ID NO 47
<211> LENGTH: 4
<212> TYPE: PRT
<213> ORGANISM: Unknown
<220> FEATURE:
<223> OTHER INFORMATION: L-type calcium channels in P-regions of domains
      I-IV

<400> SEQUENCE: 47

Glu Glu Glu Glu
 1


<210> SEQ ID NO 48
<211> LENGTH: 18
<212> TYPE: DNA
<213> ORGANISM: Artificial Sequence
<220> FEATURE:
<223> OTHER INFORMATION: primer

<400> SEQUENCE: 48

gcgtggagct ctttggag                                                    18


<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49

gcacccagtg gagaaaggtg                                                  20
```